(12) United States Patent
Lang

(10) Patent No.: US 9,308,091 B2
(45) Date of Patent: Apr. 12, 2016

(54) DEVICES AND METHODS FOR TREATMENT OF FACET AND OTHER JOINTS

(75) Inventor: Phlipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 0 days.

(21) Appl. No.: 12/464,763

(22) Filed: May 12, 2009

(65) Prior Publication Data

US 2009/0276045 A1  Nov. 5, 2009

Related U.S. Application Data

(63) Continuation-in-part of application No. 11/602,713, filed on Nov. 21, 2006, which is a continuation-in-part of application No. 10/997,407, filed on Nov. 24, 2004, which is a continuation-in-part of application No. 10/752,438, filed on Jan. 5, 2004, which is a continuation-in-part of application No. 10/724,010, filed on Nov. 25, 2003, now Pat. No. 7,618,451, which (Continued)

(51) Int. Cl.
*A61F 2/44* (2006.01)
*A61F 2/30* (2006.01)
(Continued)

(52) U.S. Cl.
CPC ........... *A61F 2/30756* (2013.01); *A61F 2/4657* (2013.01); *A61F 2/38* (2013.01); *A61F 2/389* (2013.01); *A61F 2/441* (2013.01); *A61F 2/4405* (2013.01); *A61F 2002/30062* (2013.01); *A61F 2002/3092* (2013.01); *A61F 2002/30112* (2013.01); *A61F 2002/30125* (2013.01); *A61F 2002/30179* (2013.01); *A61F 2002/30383* (2013.01); *A61F 2002/30878* (2013.01); *A61F 2002/30884* (2013.01); *A61F 2002/30952* (2013.01); *A61F 2002/30962* (2013.01); *A61F 2002/30971* (2013.01); *A61F 2210/0004* (2013.01); *A61F 2220/0025* (2013.01); *A61F 2230/0004* (2013.01); *A61F 2230/0008* (2013.01); *A61F 2230/0058* (2013.01);
(Continued)

(58) Field of Classification Search
CPC ...................................................... A61F 2/4405
See application file for complete search history.

(56) References Cited

U.S. PATENT DOCUMENTS

| | | | |
|---|---|---|---|
| 3,314,420 A | 4/1967 | Smith et al. | 128/92 |
| 3,605,123 A | 9/1971 | Hahn | 3/1 |
| 3,694,820 A | 10/1972 | Scales et al. | 3/1 |

(Continued)

FOREIGN PATENT DOCUMENTS

| | | | | |
|---|---|---|---|---|
| CN | 86209787 | 11/1987 | | A61F 2/38 |
| CN | 2305966 | 2/1999 | | A61F 2/28 |

(Continued)

OTHER PUBLICATIONS

Andersson et al., "Macintosh Arthroplasty in Rheumatoid Arthritis," Acta. Orthrop. Scand. 45(2):245-259 (1974).

(Continued)

*Primary Examiner* — Samuel Hanna
(74) *Attorney, Agent, or Firm* — Sunstein Kann Murphy & Timbers LLP

(57) ABSTRACT

Embodiments of the present invention describe methods, devices and instruments for resurfacing or replacing facet joints, uncovertebral joints and costovertebral joints. The joints can be prepared by smoothing the articular surface on one side, by distracting the joint and by implant insertion. Implants can be stabilized against a first articular surface by creating a high level of conformance with said first articular surface, while smoothing the second articular surface with a surgical instrument with a smooth mating implant surface.

9 Claims, 23 Drawing Sheets

Related U.S. Application Data is a continuation-in-part of application No. 10/305,652, filed on Nov. 27, 2002, now Pat. No. 7,468,075, which is a continuation-in-part of application No. 10/160,667, filed on May 28, 2002, said application No. 12/464,763 is a continuation-in-part of application No. 10/681,750, filed on Oct. 7, 2003, and a continuation-in-part of application No. 10/681,749, filed on Oct. 7, 2003, now Pat. No. 7,799,077, and a continuation-in-part of application No. 10/704,208.

(60) Provisional application No. 61/052,468, filed on May 12, 2008, provisional application No. 60/740,323, filed on Nov. 21, 2005, provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002, provisional application No. 60/467,686, filed on May 2, 2003, provisional application No. 60/416,601, filed on Oct. 7, 2002, provisional application No. 60/424,964, filed on Nov. 7, 2002.

(51) Int. Cl.
 *A61F 2/46* (2006.01)
 *A61F 2/38* (2006.01)

(52) U.S. Cl.
 CPC .............. *A61F2310/00017* (2013.01); *A61F 2310/00179* (2013.01); *A61F 2310/00365* (2013.01)

(56) References Cited

U.S. PATENT DOCUMENTS

| | | | | |
|---|---|---|---|---|
| 3,798,679 | A | 3/1974 | Ewald | 3/1 |
| 3,808,606 | A | 5/1974 | Tronzo | 3/1 |
| 3,816,855 | A | 6/1974 | Saleh | 3/1 |
| 3,843,975 | A | 10/1974 | Tronzo | 3/1 |
| 3,852,830 | A | 12/1974 | Marmor | 3/1 |
| 3,855,638 | A | 12/1974 | Pilliar | 3/1 |
| 3,938,198 | A | 2/1976 | Kahn et al. | 3/1.912 |
| 3,982,281 | A | 9/1976 | Giliberty | 3/1.913 |
| 3,987,499 | A | 10/1976 | Scharbach et al. | 3/1.91 |
| 3,991,425 | A | 11/1976 | Martin et al. | 3/1.91 |
| 4,000,525 | A | 1/1977 | Klawitter et al. | 3/1.911 |
| 4,052,753 | A | 10/1977 | Dedo | 3/1 |
| 4,055,862 | A | 11/1977 | Farling | 3/1.91 |
| 4,085,466 | A | 4/1978 | Goodfellow et al. | 3/1.91 |
| 4,098,626 | A | 7/1978 | Graham et al. | 149/19.4 |
| 4,164,793 | A | 8/1979 | Swanson | 3/1.91 |
| 4,178,641 | A | 12/1979 | Grundei et al. | 3/1.911 |
| 4,203,444 | A | 5/1980 | Bonnell et al. | 128/276 |
| 4,207,627 | A | 6/1980 | Cloutier | 3/1.911 |
| 4,211,228 | A | 7/1980 | Cloutier | 128/303 |
| 4,213,816 | A | 7/1980 | Morris | 156/245 |
| 4,219,893 | A | 9/1980 | Noiles | 3/1.911 |
| 4,280,231 | A | 7/1981 | Swanson | 3/1.91 |
| 4,309,778 | A | 1/1982 | Buechel et al. | 3/1.911 |
| 4,340,978 | A | 7/1982 | Buechel et al. | 3/1.911 |
| 4,344,193 | A | 8/1982 | Kenny | 3/1.911 |
| 4,368,040 | A | 1/1983 | Weissman | 433/36 |
| 4,436,684 | A | 3/1984 | White | 264/138 |
| 4,459,985 | A | 7/1984 | McKay et al. | 128/303 R |
| 4,502,161 | A | 3/1985 | Wall | 3/1.91 |
| 4,575,805 | A | 3/1986 | Moermann et al. | 364/474 |
| 4,586,496 | A | 5/1986 | Keller | 128/92 E |
| 4,594,380 | A | 6/1986 | Chapin et al. | 524/144 |
| 4,601,290 | A | 7/1986 | Effron et al. | 128/305 |
| 4,609,551 | A | 9/1986 | Caplan et al. | 424/95 |
| 4,627,853 | A | 12/1986 | Campbell et al. | 623/16 |
| 4,655,227 | A | 4/1987 | Gracovetsky | 128/781 |
| 4,662,889 | A | 5/1987 | Zichner et al. | 623/20 |
| 4,699,156 | A | 10/1987 | Gracovetsky | 128/781 |
| 4,714,472 | A | 12/1987 | Averill et al. | 623/20 |
| 4,714,474 | A | 12/1987 | Brooks, Jr. et al. | 623/20 |
| 4,769,040 | A | 9/1988 | Wevers | 623/20 |
| 4,813,436 | A | 3/1989 | Au | 128/779 |
| 4,822,365 | A | 4/1989 | Walker et al. | 623/20 |
| 4,823,807 | A | 4/1989 | Russell et al. | 128/773 |
| 4,846,835 | A | 7/1989 | Grande | 623/11 |
| 4,865,607 | A | 9/1989 | Witzel et al. | 623/20 |
| 4,872,452 | A | 10/1989 | Alexson | 128/92 VJ |
| 4,880,429 | A | 11/1989 | Stone | 623/18 |
| 4,883,488 | A | 11/1989 | Bloebaum et al. | 3/20 |
| 4,888,021 | A | 12/1989 | Forte et al. | 623/20 |
| 4,936,853 | A | 6/1990 | Fabian et al. | 623/20 |
| 4,936,862 | A | 6/1990 | Walker et al. | 623/23 |
| 4,944,757 | A | 7/1990 | Martinez et al. | 623/20 |
| 4,979,949 | A | 12/1990 | Matsen, III et al. | 606/53 |
| 5,019,103 | A | 5/1991 | Van Zile et al. | 623/20 |
| 5,021,061 | A | 6/1991 | Wevers et al. | 623/20 |
| 5,041,138 | A | 8/1991 | Vacanti et al. | 623/16 |
| 5,047,057 | A | 9/1991 | Lawes | 623/20 |
| 5,059,216 | A | 10/1991 | Winters | 623/20 |
| 5,067,964 | A | 11/1991 | Richmond et al. | 623/18 |
| 5,099,859 | A | 3/1992 | Bell | 128/781 |
| 5,108,452 | A | 4/1992 | Fallin | 623/23 |
| 5,123,927 | A | 6/1992 | Duncan et al. | 623/20 |
| 5,129,908 | A | 7/1992 | Petersen | 606/88 |
| 5,133,759 | A | 7/1992 | Turner | 623/20 |
| 5,150,304 | A | 9/1992 | Berchem et al. | 364/474.24 |
| 5,152,797 | A | 10/1992 | Luckman et al. | 623/20 |
| 5,154,178 | A | 10/1992 | Shah | 128/653.2 |
| 5,162,430 | A | 11/1992 | Rhee et al. | 525/54.1 |
| 5,171,244 | A | 12/1992 | Caspari et al. | 606/88 |
| 5,171,322 | A | 12/1992 | Kenny | 623/18 |
| 5,197,985 | A | 3/1993 | Caplan et al. | 623/16 |
| 5,206,023 | A | 4/1993 | Hunziker | 424/423 |
| 5,226,914 | A | 7/1993 | Caplan et al. | 623/16 |
| 5,234,433 | A | 8/1993 | Bert et al. | 606/88 |
| 5,236,461 | A | 8/1993 | Forte | 623/20 |
| 5,245,282 | A | 9/1993 | Mugler, III et al. | 324/309 |
| 5,246,013 | A | 9/1993 | Frank et al. | 128/774 |
| 5,246,530 | A | 9/1993 | Bugle et al. | 156/643 |
| 5,258,032 | A | 11/1993 | Bertin | 623/20 |
| 5,270,300 | A | 12/1993 | Hunziker | 514/12 |
| 5,274,565 | A | 12/1993 | Reuben | 364/474.24 |
| 5,282,868 | A | 2/1994 | Bahler | 623/20 |
| 5,288,797 | A | 2/1994 | Khalil et al. | 524/872 |
| 5,299,288 | A | 3/1994 | Glassman et al. | 395/80 |
| 5,303,148 | A | 4/1994 | Mattson et al. | 364/413.01 |
| 5,306,307 | A | 4/1994 | Senter et al. | 623/17 |
| 5,306,311 | A | 4/1994 | Stone et al. | 623/18 |
| 5,314,478 | A | 5/1994 | Oka et al. | 623/18 |
| 5,314,482 | A | 5/1994 | Goodfellow et al. | 623/20 |
| 5,320,102 | A | 6/1994 | Paul et al. | 128/653.2 |
| 5,326,363 | A | 7/1994 | Aikins | 623/20 |
| 5,326,365 | A | 7/1994 | Alvine | 623/21 |
| 5,344,459 | A | 9/1994 | Swartz | 623/18 |
| 5,360,446 | A | 11/1994 | Kennedy | 623/16 |
| 5,365,996 | A | 11/1994 | Crook | 164/45 |
| 5,368,858 | A | 11/1994 | Hunziker | 424/423 |
| 5,403,319 | A | 4/1995 | Matsen, III et al. | 606/88 |
| 5,405,395 | A | 4/1995 | Coates | 623/20 |
| 5,413,116 | A | 5/1995 | Radke et al. | 128/777 |
| 5,423,828 | A | 6/1995 | Benson | 606/102 |
| 5,433,215 | A | 7/1995 | Athanasiou et al. | 128/774 |
| 5,445,152 | A | 8/1995 | Bell et al. | 128/653.5 |
| 5,448,489 | A | 9/1995 | Reuben | 364/474.05 |
| 5,452,407 | A | 9/1995 | Crook | 395/121 |
| 5,468,787 | A | 11/1995 | Braden et al. | 523/113 |
| 5,478,739 | A | 12/1995 | Slivka et al. | 435/240.23 |
| 5,489,309 | A | 2/1996 | Lackey et al. | 623/19 |
| 5,501,687 | A | 3/1996 | Willert et al. | 606/94 |
| 5,503,162 | A | 4/1996 | Athanasiou et al. | 128/774 |
| 5,507,820 | A | 4/1996 | Pappas | 623/20 |
| 5,510,121 | A | 4/1996 | Rhee et al. | 424/520 |
| 5,522,900 | A | 6/1996 | Hollister | 623/18 |
| 5,523,843 | A | 6/1996 | Yamane et al. | 356/363 |
| 5,541,515 | A | 7/1996 | Tsujita | 324/318 |

(56) References Cited

U.S. PATENT DOCUMENTS

| | | | |
|---|---|---|---|
| 5,549,690 A | 8/1996 | Hollister et al. | 623/21 |
| 5,554,190 A | 9/1996 | Draenert | 623/16 |
| 5,556,432 A | 9/1996 | Kubein-Meesenburg et al. | 623/20 |
| 5,560,096 A | 10/1996 | Stephens | 29/558 |
| 5,564,437 A | 10/1996 | Bainville et al. | 128/774 |
| 5,571,191 A * | 11/1996 | Fitz | 623/17.11 |
| 5,571,205 A | 11/1996 | James | 623/24 |
| 5,609,640 A | 3/1997 | Johnson | 623/20 |
| 5,611,802 A | 3/1997 | Samuelson et al. | 606/86 |
| 5,616,146 A | 4/1997 | Murray | 606/80 |
| 5,632,745 A | 5/1997 | Schwartz | 606/75 |
| 5,671,741 A | 9/1997 | Lang et al. | 128/653.2 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,741,215 A | 4/1998 | D'Urso | 600/407 |
| 5,743,918 A | 4/1998 | Calandruccio et al. | 623/21 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/88 |
| 5,759,205 A | 6/1998 | Valentini | 623/16 |
| 5,762,125 A | 6/1998 | Mastrorio | 164/4.1 |
| 5,768,134 A | 6/1998 | Swaelens et al. | 364/468.28 |
| 5,769,092 A | 6/1998 | Williamson, Jr. | 128/898 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A | 10/1998 | Sahay et al. | 623/16 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,643 A | 5/1999 | Walker | 623/20 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,968,099 A | 10/1999 | Badorf et al. | 623/20 |
| 5,972,385 A | 10/1999 | Liu et al. | 424/486 |
| 5,995,738 A | 11/1999 | DiGioia, III et al. | 395/500.32 |
| 5,997,577 A | 12/1999 | Herrington et al. | 623/20 |
| 6,002,859 A | 12/1999 | DiGioia, III et al. | 395/500.32 |
| 6,013,103 A | 1/2000 | Kaufman et al. | 623/20 |
| 6,046,379 A | 4/2000 | Stone et al. | 623/11 |
| 6,057,927 A | 5/2000 | Lévesque et al. | 356/432 T |
| 6,078,680 A | 6/2000 | Yoshida et al. | 382/128 |
| 6,081,577 A | 6/2000 | Webber | 378/23 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,102,955 A | 8/2000 | Mendes et al. | 623/20 |
| 6,110,209 A | 8/2000 | Stone | 623/16.11 |
| 6,112,109 A | 8/2000 | D'Urso | 600/407 |
| 6,120,541 A | 9/2000 | Johnson | 623/14.12 |
| 6,120,543 A | 9/2000 | Kubein-Meesenburg et al. | 623/20 |
| 6,126,690 A | 10/2000 | Ateshian et al. | 623/18 |
| 6,132,468 A | 10/2000 | Mansmann | 623/20.16 |
| 6,139,578 A | 10/2000 | Lee et al. | 623/16.11 |
| 6,146,422 A | 11/2000 | Lawson | 623/17.16 |
| 6,151,521 A | 11/2000 | Guo et al. | 600/407 |
| 6,152,960 A | 11/2000 | Pappas | 623/20.31 |
| 6,156,069 A | 12/2000 | Amstutz | 623/22.11 |
| 6,161,080 A | 12/2000 | Aouni-Ateshian et al. | 703/11 |
| 6,162,208 A | 12/2000 | Hipps | 606/1 |
| 6,165,221 A | 12/2000 | Schmotzer | 623/20.11 |
| 6,171,340 B1 | 1/2001 | McDowell | 623/18.11 |
| 6,175,655 B1 | 1/2001 | George, III et al. | 382/257 |
| 6,178,225 B1 | 1/2001 | Zur et al. | 378/98.2 |
| 6,187,010 B1 | 2/2001 | Masini | 606/86 |
| 6,197,064 B1 | 3/2001 | Haines et al. | 623/20.31 |
| 6,197,325 B1 | 3/2001 | MacPhee et al. | 424/426 |
| 6,200,606 B1 | 3/2001 | Peterson et al. | 424/574 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,249,692 B1 | 6/2001 | Cowin | 600/407 |
| 6,251,143 B1 | 6/2001 | Schwartz et al. | 623/23.72 |
| 6,254,639 B1 | 7/2001 | Peckitt | 623/11.11 |
| 6,261,296 B1 | 7/2001 | Aebi et al. | 606/90 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,325,828 B1 | 12/2001 | Dennis et al. | 623/20.14 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |
| 6,342,075 B1 | 1/2002 | MacArthur | 623/20.14 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,379,388 B1 | 4/2002 | Ensign et al. | 623/20.34 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,402,786 B1 | 6/2002 | Insall et al. | 623/20.35 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,450,978 B1 | 9/2002 | Brosseau et al. | 600/595 |
| 6,459,948 B1 | 10/2002 | Ateshian et al. | 700/117 |

(56) References Cited

U.S. PATENT DOCUMENTS

| | | | |
|---|---|---|---|
| 6,468,314 B2 | 10/2002 | Schwartz et al. | 623/23.72 |
| 6,479,996 B1 | 11/2002 | Hoogeveen et al. | 324/309 |
| 6,482,209 B1 | 11/2002 | Engh et al. | 606/79 |
| 6,510,334 B1 | 1/2003 | Schuster et al. | 600/407 |
| 6,514,514 B1 | 2/2003 | Atkinson et al. | 424/423 |
| 6,520,964 B2 | 2/2003 | Tallarida et al. | 396/567 |
| 6,533,737 B1 | 3/2003 | Brosseau et al. | 600/595 |
| 6,556,855 B2 | 4/2003 | Thesen | 600/419 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,591,581 B2 | 7/2003 | Schmieding | 53/396 |
| 6,592,624 B1 | 7/2003 | Fraser et al. | 623/17.16 |
| 6,623,526 B1 | 9/2003 | Lloyd | 623/20.28 |
| 6,626,945 B2 | 9/2003 | Simon et al. | 623/17.19 |
| 6,632,235 B2 | 10/2003 | Weikel et al. | 606/192 |
| 6,652,587 B1 | 11/2003 | Felt et al. | 623/20.16 |
| 6,679,917 B2 | 1/2004 | Ek | 623/20.14 |
| 6,690,816 B2 | 2/2004 | Aylward et al. | 382/128 |
| 6,692,448 B2 | 2/2004 | Tanaka et al. | 600/587 |
| 6,702,821 B2 | 3/2004 | Bonutti | 606/88 |
| 6,712,856 B1 * | 3/2004 | Carignan et al. | 623/20.35 |
| 6,719,794 B2 | 4/2004 | Gerber et al. | 623/17.11 |
| 6,770,078 B2 | 8/2004 | Bonutti | 606/88 |
| 6,772,026 B2 | 8/2004 | Bradbury et al. | 700/98 |
| 6,799,066 B2 | 9/2004 | Steines et al. | 600/407 |
| 6,816,607 B2 | 11/2004 | O'Donnell et al. | 382/131 |
| 6,835,377 B2 | 12/2004 | Goldberg et al. | 424/93.7 |
| 6,855,165 B2 | 2/2005 | Fell et al. | 623/14.12 |
| 6,873,741 B2 | 3/2005 | Li | 382/266 |
| 6,893,463 B2 | 5/2005 | Fell et al. | 623/14.12 |
| 6,893,467 B1 | 5/2005 | Bercovy | 623/20.14 |
| 6,902,582 B2 | 6/2005 | Kubein-Meesenburg et al. | 623/20.31 |
| 6,905,514 B2 | 6/2005 | Carignan et al. | 623/20.35 |
| 6,911,044 B2 | 6/2005 | Fell et al. | 623/14.12 |
| 6,916,341 B2 | 7/2005 | Rolston | 623/20.3 |
| 6,923,817 B2 | 8/2005 | Carson et al. | 606/130 |
| 6,923,831 B2 | 8/2005 | Fell et al. | 623/14.12 |
| 6,932,842 B1 | 8/2005 | Litschko et al. | 623/16.11 |
| 6,964,687 B1 | 11/2005 | Bernard et al. | 623/17.16 |
| 6,966,928 B2 | 11/2005 | Fell et al. | 623/14.12 |
| 6,978,188 B1 | 12/2005 | Christensen | 700/118 |
| 6,984,981 B2 | 1/2006 | Tamez-Peña et al. | 324/309 |
| 6,998,841 B1 | 2/2006 | Tamez-Peña et al. | 324/302 |
| 7,020,314 B1 | 3/2006 | Suri et al. | 382/130 |
| 7,048,741 B2 | 5/2006 | Swanson | 606/888 |
| 7,050,534 B2 | 5/2006 | Lang | 378/54 |
| 7,058,159 B2 | 6/2006 | Lang et al. | 378/54 |
| 7,058,209 B2 | 6/2006 | Chen et al. | 382/117 |
| 7,060,101 B2 | 6/2006 | O'Connor et al. | 623/20.32 |
| 7,105,026 B2 | 9/2006 | Johnson et al. | 623/20.14 |
| 7,115,131 B2 | 10/2006 | Engh et al. | 606/79 |
| 7,172,596 B2 | 2/2007 | Coon et al. | 606/87 |
| 7,174,282 B2 | 2/2007 | Hollister et al. | 703/2 |
| 7,184,814 B2 | 2/2007 | Lang et al. | 600/416 |
| 7,204,807 B2 | 4/2007 | Tsoref | 600/438 |
| 7,238,203 B2 | 7/2007 | Bagga et al. | 623/17.11 |
| 7,239,908 B1 | 7/2007 | Alexander et al. | 600/427 |
| 7,244,273 B2 | 7/2007 | Pedersen et al. | 623/14.12 |
| 7,245,697 B2 | 7/2007 | Lang | 378/54 |
| 7,292,674 B2 | 11/2007 | Lang | 378/54 |
| 7,326,252 B2 | 2/2008 | Otto et al. | 623/20.15 |
| 7,379,529 B2 | 5/2008 | Lang | 378/54 |
| 7,438,685 B2 | 10/2008 | Burdette et al. | 600/439 |
| 7,467,892 B2 | 12/2008 | Lang et al. | 378/207 |
| 7,468,075 B2 | 12/2008 | Lang et al. | 623/16.11 |
| 7,517,358 B2 | 4/2009 | Petersen | 606/247 |
| 7,520,901 B2 | 4/2009 | Engh et al. | 623/20.21 |
| 7,534,263 B2 | 5/2009 | Burdulis, Jr. et al. | 623/14.12 |
| 7,572,293 B2 | 8/2009 | Rhodes et al. | 623/20.32 |
| 7,603,192 B2 | 10/2009 | Martin et al. | 700/98 |
| 7,611,519 B2 | 11/2009 | Lefevre et al. | 606/102 |
| 7,611,653 B1 | 11/2009 | Elsner et al. | 264/255 |
| 7,615,054 B1 | 11/2009 | Bonutti | 606/88 |
| 7,618,451 B2 | 11/2009 | Berez et al. | 623/14.12 |
| 7,634,119 B2 | 12/2009 | Tsougarakis et al. | 382/128 |
| 7,718,109 B2 | 5/2010 | Robb et al. | 264/308 |
| 7,796,791 B2 | 9/2010 | Tsougarakis et al. | 382/128 |
| 7,799,077 B2 | 9/2010 | Lang et al. | 623/14.12 |
| 7,806,896 B1 | 10/2010 | Bonutti | 606/86 R |
| 7,842,092 B2 | 11/2010 | Otto et al. | 623/18.11 |
| 7,846,183 B2 | 12/2010 | Blain | 606/247 |
| 7,881,768 B2 | 2/2011 | Lang et al. | 600/407 |
| 7,914,582 B2 | 3/2011 | Felt et al. | 623/20.16 |
| 7,935,151 B2 | 5/2011 | Haines | 623/20.35 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,070,821 B2 | 12/2011 | Roger | 623/20.17 |
| 8,077,950 B2 | 12/2011 | Tsougarakis et al. | 382/128 |
| 8,083,745 B2 | 12/2011 | Lang et al. | 606/87 |
| 8,086,336 B2 | 12/2011 | Christensen | 700/98 |
| 8,094,900 B2 | 1/2012 | Steines et al. | 382/128 |
| 8,105,330 B2 | 1/2012 | Fitz et al. | 606/88 |
| 8,112,142 B2 | 2/2012 | Alexander et al. | 600/407 |
| RE43,282 E | 3/2012 | Alexander et al. | 600/427 |
| 8,192,498 B2 | 6/2012 | Wagner et al. | 623/20.21 |
| 8,211,181 B2 | 7/2012 | Walker | 623/20.21 |
| 8,234,097 B2 | 7/2012 | Steines et al. | 703/1 |
| 8,236,061 B2 | 8/2012 | Heldreth et al. | 623/20.31 |
| 8,265,730 B2 | 9/2012 | Alexander et al. | 600/410 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | 606/86 R |
| 8,337,507 B2 | 12/2012 | Lang et al. | 606/102 |
| 8,337,508 B2 | 12/2012 | Lavallee et al. | 606/105 |
| 8,343,218 B2 | 1/2013 | Lang et al. | 623/16.11 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,073 B2 | 2/2013 | Wasielewski | 606/102 |
| 8,377,129 B2 | 2/2013 | Fitz et al. | 623/14.12 |
| 8,380,471 B2 | 2/2013 | Iannotti et al. | 703/6 |
| 8,407,067 B2 | 3/2013 | Uthgenannt et al. | 705/2 |
| 8,439,926 B2 | 5/2013 | Bojarski et al. | 606/88 |
| 8,457,930 B2 | 6/2013 | Schroeder | 703/1 |
| 8,460,304 B2 | 6/2013 | Fitz et al. | 606/88 |
| 8,473,305 B2 | 6/2013 | Belcher et al. | 705/2 |
| 8,480,754 B2 | 7/2013 | Bojarski et al. | 623/20.35 |
| 8,486,150 B2 | 7/2013 | White et al. | 623/20.21 |
| 8,500,740 B2 | 8/2013 | Bojarski et al. | 606/86 R |
| 8,521,492 B2 | 8/2013 | Otto et al. | 703/6 |
| 8,529,568 B2 | 9/2013 | Bouadi | 606/84 |
| 8,529,630 B2 | 9/2013 | Bojarski et al. | 623/20.14 |
| 8,532,807 B2 | 9/2013 | Metzger | 700/98 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,617,172 B2 | 12/2013 | Fitz et al. | 606/88 |
| 8,617,242 B2 | 12/2013 | Philipp | 623/16.11 |
| 8,623,026 B2 | 1/2014 | Wong et al. | 606/96 |
| 8,634,617 B2 | 1/2014 | Tsougarakis et al. | 382/128 |
| 8,638,998 B2 | 1/2014 | Steines et al. | 382/128 |
| 8,641,716 B2 | 2/2014 | Fitz et al. | 606/80 |
| 8,657,827 B2 | 2/2014 | Fitz et al. | 606/87 |
| 8,682,052 B2 | 3/2014 | Fitz et al. | 382/131 |
| 8,690,945 B2 | 4/2014 | Fitz et al. | 623/16.11 |
| 8,709,089 B2 | 4/2014 | Lang et al. | 623/18.11 |
| 8,735,773 B2 | 5/2014 | Lang | 219/121.72 |
| 8,771,365 B2 | 7/2014 | Bojarski et al. | 623/20.32 |

(56) References Cited

U.S. PATENT DOCUMENTS

| | | | |
|---|---|---|---|
| 8,882,847 B2 | 11/2014 | Burdulis, Jr. et al. | 623/20.32 |
| 8,906,107 B2 | 12/2014 | Bojarski et al. | 623/20.35 |
| 8,926,706 B2 | 1/2015 | Bojarski et al. | 623/20.14 |
| 8,932,363 B2 | 1/2015 | Tsougarakis et al. | 623/20.14 |
| 8,945,230 B2 | 2/2015 | Lang et al. | 623/20.31 |
| 8,965,088 B2 | 2/2015 | Tsougarakis et al. | 382/128 |
| 8,974,539 B2 | 3/2015 | Bojarski et al. | 623/20.14 |
| 9,055,953 B2 | 6/2015 | Lang et al. | 606/102 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0016543 A1 | 2/2002 | Tyler | 600/410 |
| 2002/0022884 A1 | 2/2002 | Mansmann | 623/14.12 |
| 2002/0045940 A1 | 4/2002 | Giannetti et al. | 623/11.11 |
| 2002/0052606 A1 | 5/2002 | Bonutti | 606/88 |
| 2002/0059049 A1 | 5/2002 | Bradbury et al. | 703/11 |
| 2002/0067798 A1 | 6/2002 | Lang et al. | 378/54 |
| 2002/0068979 A1 | 6/2002 | Brown et al. | 623/20.3 |
| 2002/0072821 A1 | 6/2002 | Baker | 700/98 |
| 2002/0082703 A1 | 6/2002 | Repicci | 623/20.29 |
| 2002/0082741 A1 | 6/2002 | Mazumder et al. | 700/123 |
| 2002/0087274 A1 | 7/2002 | Alexander et al. | 702/19 |
| 2002/0106625 A1 | 8/2002 | Hung et al. | 435/1.1 |
| 2002/0111694 A1 | 8/2002 | Ellingsen et al. | 623/23.57 |
| 2002/0114425 A1 | 8/2002 | Lang | 378/56 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0147392 A1 | 10/2002 | Steines et al. | 600/407 |
| 2002/0151986 A1 | 10/2002 | Asculai et al. | 424/484 |
| 2002/0173852 A1 | 11/2002 | Felt et al. | 623/20.32 |
| 2002/0177770 A1 | 11/2002 | Lang et al. | 600/410 |
| 2002/0183850 A1 | 12/2002 | Felt et al. | 623/20.16 |
| 2003/0014122 A1 | 1/2003 | Whiteside | 623/20.32 |
| 2003/0015208 A1 | 1/2003 | Lang et al. | 128/922 |
| 2003/0031292 A1 | 2/2003 | Lang | 378/54 |
| 2003/0035773 A1 | 2/2003 | Totterman et al. | 424/9.1 |
| 2003/0045935 A1 | 3/2003 | Angelucci et al. | 623/17.11 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0063704 A1 | 4/2003 | Lang | 378/54 |
| 2003/0069591 A1 | 4/2003 | Carson et al. | 606/130 |
| 2003/0100953 A1 | 5/2003 | Rosa et al. | 623/20.3 |
| 2003/0158606 A1 | 8/2003 | Coon et al. | 623/20.15 |
| 2003/0216669 A1 | 11/2003 | Lang et al. | 600/587 |
| 2003/0225457 A1 | 12/2003 | Justin et al. | 623/20.14 |
| 2003/0236473 A1 | 12/2003 | Dore et al. | 600/587 |
| 2004/0006393 A1 | 1/2004 | Burkinshaw | 623/20.3 |
| 2004/0062358 A1 | 4/2004 | Lang et al. | 378/207 |
| 2004/0081287 A1 | 4/2004 | Lang et al. | 378/210 |
| 2004/0098132 A1 | 5/2004 | Andriacchi et al. | 623/20.35 |
| 2004/0098133 A1 | 5/2004 | Carignan et al. | 623/20.35 |
| 2004/0102851 A1 | 5/2004 | Saladino | 623/20.15 |
| 2004/0102852 A1 | 5/2004 | Johnson et al. | 623/20.15 |
| 2004/0102866 A1* | 5/2004 | Harris et al. | 700/117 |
| 2004/0117015 A1 | 6/2004 | Biscup | 623/16.11 |
| 2004/0117023 A1 | 6/2004 | Gerbec et al. | 623/18.11 |
| 2004/0122521 A1 | 6/2004 | Lee et al. | 623/20.15 |
| 2004/0133276 A1 | 7/2004 | Lang et al. | 623/14.12 |
| 2004/0136583 A1 | 7/2004 | Harada et al. | 382/131 |
| 2004/0138754 A1 | 7/2004 | Lang et al. | 623/20.14 |
| 2004/0138755 A1 | 7/2004 | O'Connor et al. | 623/20.32 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0199249 A1 | 10/2004 | Fell | 623/14.12 |
| 2004/0199258 A1 | 10/2004 | Macara | 623/22.32 |
| 2004/0204644 A1 | 10/2004 | Tsougarakis et al. | 600/410 |
| 2004/0204760 A1 | 10/2004 | Fitz et al. | 623/14.12 |
| 2004/0204766 A1 | 10/2004 | Siebel | 623/20.31 |
| 2004/0236424 A1 | 11/2004 | Berez et al. | 623/14.12 |
| 2005/0010106 A1 | 1/2005 | Lang et al. | 600/425 |
| 2005/0015153 A1 | 1/2005 | Goble et al. | 623/23.46 |
| 2005/0021042 A1 | 1/2005 | Marnay et al. | 606/99 |
| 2005/0033424 A1 | 2/2005 | Fell | 623/14.12 |
| 2005/0043807 A1 | 2/2005 | Wood | 623/20.14 |
| 2005/0055028 A1 | 3/2005 | Haines | 606/79 |
| 2005/0078802 A1 | 4/2005 | Lang et al. | 387/207 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0125029 A1 | 6/2005 | Bernard et al. | 606/205 |
| 2005/0148843 A1 | 7/2005 | Roose | 700/117 |
| 2005/0154471 A1 | 7/2005 | Aram et al. | 623/20.15 |
| 2005/0171612 A1 | 8/2005 | Rolston | 623/20.19 |
| 2005/0197814 A1 | 9/2005 | Aram et al. | 703/11 |
| 2005/0203384 A1 | 9/2005 | Sati et al. | 600/426 |
| 2005/0216305 A1 | 9/2005 | Funderud | 705/2 |
| 2005/0226374 A1 | 10/2005 | Lang et al. | 378/54 |
| 2005/0234461 A1 | 10/2005 | Burdulis, Jr. et al. | 606/79 |
| 2005/0244239 A1 | 11/2005 | Shimp | 409/132 |
| 2005/0267584 A1 | 12/2005 | Burdulis et al. | 623/20.19 |
| 2005/0278034 A1 | 12/2005 | Johnson et al. | 623/20.15 |
| 2006/0009853 A1 | 1/2006 | Justin et al. | 623/20.3 |
| 2006/0058884 A1 | 3/2006 | Aram et al. | 623/20.15 |
| 2006/0069318 A1 | 3/2006 | Keaveny et al. | 600/300 |
| 2006/0111722 A1 | 5/2006 | Bouadi | 606/79 |
| 2006/0111726 A1 | 5/2006 | Felt et al. | 606/86 |
| 2006/0111781 A1* | 5/2006 | Petersen | 623/17.11 |
| 2006/0129246 A1 | 6/2006 | Steffensmeier | 623/20.29 |
| 2006/0136058 A1 | 6/2006 | Pietrzak | 623/13.14 |
| 2006/0149374 A1 | 7/2006 | Winslow et al. | 623/17.11 |
| 2006/0190086 A1 | 8/2006 | Clemow et al. | 623/20.15 |
| 2006/0210017 A1 | 9/2006 | Lang | 378/54 |
| 2006/0210018 A1 | 9/2006 | Lang | 378/54 |
| 2006/0265078 A1 | 11/2006 | McMinn | 623/20.14 |
| 2007/0005143 A1 | 1/2007 | Ek et al. | 623/20.32 |
| 2007/0015995 A1 | 1/2007 | Lang | 600/407 |
| 2007/0047794 A1 | 3/2007 | Lang et al. | 378/132 |
| 2007/0067032 A1 | 3/2007 | Felt et al. | 623/14.12 |
| 2007/0083266 A1 | 4/2007 | Lang | 623/17.11 |
| 2007/0100462 A1 | 5/2007 | Lang et al. | 623/20.29 |
| 2007/0112428 A1* | 5/2007 | Lancial | A61F 2/4405 623/17.12 |
| 2007/0118055 A1 | 5/2007 | McCombs | 600/587 |
| 2007/0118222 A1 | 5/2007 | Lang | 623/17.12 |
| 2007/0118243 A1 | 5/2007 | Schroeder et al. | 700/118 |
| 2007/0156171 A1 | 7/2007 | Lang et al. | 606/205 |
| 2007/0190108 A1 | 8/2007 | Datta et al. | 424/423 |
| 2007/0198022 A1 | 8/2007 | Lang et al. | 606/88 |
| 2007/0203430 A1 | 8/2007 | Lang et al. | 600/587 |
| 2007/0233156 A1 | 10/2007 | Metzger | 606/130 |
| 2007/0233269 A1 | 10/2007 | Steines et al. | 623/20.21 |
| 2007/0239165 A1 | 10/2007 | Amirouche | 606/86 |
| 2007/0250169 A1 | 10/2007 | Lang | 623/17.12 |
| 2007/0255288 A1 | 11/2007 | Mahfouz et al. | 606/102 |
| 2007/0274444 A1 | 11/2007 | Lang | 378/54 |
| 2007/0276224 A1 | 11/2007 | Lang et al. | 600/410 |
| 2007/0276501 A1 | 11/2007 | Betz et al. | 623/17.16 |
| 2007/0282451 A1 | 12/2007 | Metzger et al. | 623/20.28 |
| 2008/0009950 A1 | 1/2008 | Richardson | 623/20.29 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0119938 A1 | 5/2008 | Oh | 623/20.14 |
| 2008/0119940 A1 | 5/2008 | Otto et al. | 623/20.31 |
| 2008/0140212 A1 | 6/2008 | Metzger et al. | 623/20.31 |
| 2008/0147072 A1 | 6/2008 | Park et al. | 606/87 |
| 2008/0170659 A1 | 7/2008 | Lang et al. | 378/56 |

(56) References Cited

U.S. PATENT DOCUMENTS

| | | | |
|---|---|---|---|
| 2008/0172125 A1 | 7/2008 | Ek | 623/14.12 |
| 2008/0195108 A1 | 8/2008 | Bhatnagar et al. | 606/87 |
| 2008/0195216 A1 | 8/2008 | Lang | 623/18.11 |
| 2008/0208348 A1 | 8/2008 | Fitz | 623/19.14 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0255445 A1 | 10/2008 | Neubauer et al. | 600/416 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2008/0319448 A1 | 12/2008 | Lavallee et al. | 606/102 |
| 2009/0062925 A1 | 3/2009 | Samuelson | 623/23.12 |
| 2009/0076371 A1 | 3/2009 | Lang et al. | 600/407 |
| 2009/0076508 A1 | 3/2009 | Weinans et al. | 606/62 |
| 2009/0088865 A1 | 4/2009 | Brehm | 623/22.21 |
| 2009/0118830 A1 | 5/2009 | Fell | 623/14.12 |
| 2009/0131941 A1 | 5/2009 | Park et al. | 606/87 |
| 2009/0149977 A1 | 6/2009 | Schendel | 700/98 |
| 2009/0151736 A1 | 6/2009 | Belcher et al. | 128/898 |
| 2009/0222103 A1 | 9/2009 | Fitz et al. | 623/18.11 |
| 2009/0226068 A1 | 9/2009 | Fitz et al. | 382/131 |
| 2009/0228111 A1 | 9/2009 | Otto | 623/20.19 |
| 2009/0228113 A1 | 9/2009 | Lang et al. | 623/20.32 |
| 2009/0270868 A1 | 10/2009 | Park et al. | 606/87 |
| 2009/0276045 A1 | 11/2009 | Lang | 623/14.12 |
| 2009/0306676 A1 | 12/2009 | Lang et al. | 606/102 |
| 2009/0312805 A1 | 12/2009 | Lang et al. | 606/86 R |
| 2009/0326666 A1 | 12/2009 | Wyss et al. | 623/20.29 |
| 2009/0326670 A1 | 12/2009 | Keefer et al. | 623/22.22 |
| 2010/0042105 A1 | 2/2010 | Park et al. | 606/87 |
| 2010/0054572 A1 | 3/2010 | Tsougarakis et al. | 382/131 |
| 2010/0191244 A1 | 7/2010 | White et al. | 606/88 |
| 2010/0217270 A1 | 8/2010 | Polinski et al. | 606/87 |
| 2010/0274534 A1 | 10/2010 | Steines et al. | 703/1 |
| 2010/0303313 A1 | 12/2010 | Lang et al. | 382/128 |
| 2010/0303317 A1 | 12/2010 | Tsougarakis et al. | 382/128 |
| 2010/0303324 A1 | 12/2010 | Lang et al. | 382/131 |
| 2010/0305708 A1 | 12/2010 | Lang et al. | 623/20.18 |
| 2010/0305907 A1 | 12/2010 | Fitz et al. | 703/1 |
| 2010/0329530 A1 | 12/2010 | Lang et al. | 382/128 |
| 2010/0331991 A1 | 12/2010 | Wilkinson et al. | 623/20.32 |
| 2010/0332194 A1 | 12/2010 | McGuan et al. | 703/1 |
| 2011/0022179 A1 | 1/2011 | Andriacchi et al. | 623/20.18 |
| 2011/0029091 A1 | 2/2011 | Bojarski et al. | 623/20.32 |
| 2011/0029093 A1 | 2/2011 | Bojarski et al. | 623/20.35 |
| 2011/0046735 A1 | 2/2011 | Metzger et al. | 623/14.12 |
| 2011/0066245 A1 | 3/2011 | Lang et al. | 623/18.11 |
| 2011/0071645 A1 | 3/2011 | Bojarski et al. | 623/20.35 |
| 2011/0071802 A1 | 3/2011 | Bojarski et al. | 703/1 |
| 2011/0087332 A1 | 4/2011 | Bojarski et al. | 623/20.32 |
| 2011/0087465 A1 | 4/2011 | Mahfouz | 703/1 |
| 2011/0092804 A1 | 4/2011 | Schoenefeld et al. | 600/416 |
| 2011/0093108 A1 | 4/2011 | Ashby et al. | 700/103 |
| 2011/0125009 A1 | 5/2011 | Lang et al. | 600/425 |
| 2011/0144760 A1 | 6/2011 | Wong et al. | 623/20.14 |
| 2011/0184526 A1 | 7/2011 | White et al. | 623/20.32 |
| 2011/0218635 A1 | 9/2011 | Amis et al. | 623/20.18 |
| 2011/0264097 A1 | 10/2011 | Hodorek et al. | 606/88 |
| 2011/0266265 A1 | 11/2011 | Lang | 219/121.72 |
| 2011/0288669 A1 | 11/2011 | Sanford et al. | 700/103 |
| 2011/0295378 A1 | 12/2011 | Bojarski et al. | 623/20.35 |
| 2011/0305379 A1 | 12/2011 | Mahfouz | 382/131 |
| 2012/0022659 A1 | 1/2012 | Wentorf | 623/20.32 |
| 2012/0093377 A1 | 4/2012 | Tsougarakis et al. | 382/128 |
| 2012/0116203 A1 | 5/2012 | Vancraen et al. | 600/407 |
| 2012/0191205 A1 | 7/2012 | Bojarski et al. | 623/20.32 |
| 2012/0191420 A1 | 7/2012 | Bojarski et al. | 703/1 |
| 2012/0197408 A1 | 8/2012 | Lang et al. | 623/18.11 |
| 2012/0201440 A1 | 8/2012 | Steines et al. | 382/131 |
| 2012/0209394 A1 | 8/2012 | Bojarski et al. | 623/20.32 |
| 2012/0232669 A1 | 9/2012 | Bojarski et al. | 623/20.3 |
| 2012/0232670 A1 | 9/2012 | Bojarski et al. | 623/20.35 |
| 2012/0232671 A1 | 9/2012 | Bojarski et al. | 623/20.35 |
| 2012/0265496 A1 | 10/2012 | Mahfouz | 703/1 |
| 2013/0006598 A1 | 1/2013 | Alexander et al. | 703/11 |
| 2013/0035766 A1 | 2/2013 | Meridew | 623/22.21 |
| 2013/0071828 A1 | 3/2013 | Lang et al. | 434/274 |
| 2013/0103363 A1 | 4/2013 | Lang et al. | 703/1 |
| 2013/0110471 A1 | 5/2013 | Lang et al. | 703/1 |
| 2013/0144570 A1 | 6/2013 | Axelson, Jr. et al. | 703/1 |
| 2013/0158671 A1 | 6/2013 | Uthgenannt et al. | 623/20.35 |
| 2013/0165939 A1 | 6/2013 | Ries et al. | 606/88 |
| 2013/0197870 A1 | 8/2013 | Steines et al. | 703/1 |
| 2013/0199259 A1 | 8/2013 | Smith | 72/362 |
| 2013/0203031 A1 | 8/2013 | Mckinnon et al. | 434/262 |
| 2013/0211531 A1 | 8/2013 | Steines et al. | 623/20.35 |
| 2013/0245803 A1 | 9/2013 | Lang | 700/98 |
| 2013/0297031 A1 | 11/2013 | Hafez | 623/20.14 |
| 2014/0005792 A1 | 1/2014 | Lang et al. | 623/20.32 |
| 2014/0029814 A1 | 1/2014 | Fitz et al. | 382/128 |
| 2014/0039631 A1 | 2/2014 | Bojarski et al. | 623/18.11 |
| 2014/0086780 A1 | 3/2014 | Miller et al. | 419/1 |
| 2014/0109384 A1 | 4/2014 | Lang | 29/557 |
| 2014/0115872 A1 | 5/2014 | Steines et al. | 29/592 |
| 2014/0136154 A1 | 5/2014 | Bojarski et al. | 703/1 |
| 2014/0153798 A1 | 6/2014 | Tsougarakis et al. | 382/128 |
| 2014/0194996 A1 | 7/2014 | Bojarski et al. | 623/20.35 |
| 2014/0207243 A1 | 7/2014 | Fitz et al. | 623/20.16 |
| 2014/0250676 A1 | 9/2014 | Lang et al. | 29/592 |
| 2014/0250677 A1 | 9/2014 | Lang | 29/592 |
| 2014/0303629 A1 | 10/2014 | Lang et al. | 606/87 |
| 2014/0336774 A1 | 11/2014 | Fitz et al. | 623/20.35 |
| 2015/0032217 A1 | 1/2015 | Bojarski et al. | 623/20.32 |
| 2015/0157461 A1 | 6/2015 | Burdulis, Jr. et al. | |
| 2015/0216615 A1 | 8/2015 | Tsougarakis et al. | |

FOREIGN PATENT DOCUMENTS

| | | | |
|---|---|---|---|
| CN | 1480111 A | 3/2004 | A61F 2/30 |
| CN | 1586432 | 3/2005 | A61F 2/28 |
| CN | 101278866 | 10/2008 | A61F 2/38 |
| CN | 101288597 | 10/2008 | A61B 17/56 |
| DE | 2306552 | 8/1974 | A61F 1/00 |
| DE | 3516743 | 11/1986 | A61F 2/36 |
| DE | 8909091 | 9/1987 | A61F 2/35 |
| DE | 44 34 539 | 4/1996 | A61F 2/38 |
| DE | 44 34 5239 | 4/1996 | A61F 2/38 |
| DE | 19803673 | 8/1999 | A61L 27/54 |
| DE | 19926083 | 12/2000 | A61L 27/54 |
| DE | 10135771 | 2/2003 | A61B 17/70 |
| EP | 0528080 | 2/1993 | A61F 2/30 |
| EP | 0600806 | 6/1994 | A61L 25/00 |
| EP | 0672397 | 9/1995 | A61F 2/38 |
| EP | 0681817 | 11/1995 | A61F 2/38 |
| EP | 0 704 193 | 4/1996 | A61F 2/30 |
| EP | 0626156 | 7/1997 | A61F 2/38 |
| EP | 0613380 | 12/1999 | A61L 27/00 |
| EP | 1074229 | 2/2001 | A61F 2/38 |
| EP | 1077253 | 2/2001 | C12N 5/00 |
| EP | 1120087 | 8/2001 | A61B 17/06 |
| EP | 1129675 | 9/2001 | A61F 2/30 |
| EP | 0732091 | 12/2001 | A61F 2/38 |
| EP | 0896825 | 7/2002 | A61L 27/00 |
| EP | 0814731 | 8/2002 | A61F 2/30 |
| EP | 1234552 | 8/2002 | A61F 2/00 |
| EP | 1234555 | 8/2002 | A61F 2/30 |
| EP | 0809987 | 10/2002 | A61F 2/38 |
| EP | 0833620 | 10/2002 | A61K 9/22 |
| EP | 1327423 | 7/2003 | A61F 2/38 |
| EP | 1329205 | 7/2003 | A61F 2/38 |
| EP | 0530804 | 6/2004 | A61L 25/00 |
| EP | 1437101 | 7/2004 | A61F 2/08 |
| EP | 1070487 | 9/2005 | A61F 2/08 |
| EP | 1886640 | 2/2008 | A61B 19/00 |
| EP | 2324799 | 5/2011 | A61F 2/38 |
| EP | 2173260 | 1/2012 | A61B 17/15 |
| FR | 2589720 | 11/1985 | A61F 2/38 |
| FR | 2740326 | 4/1997 | A61F 2/38 |
| GB | 1451283 | 9/1976 | A61F 1/24 |
| GB | 2291355 | 1/1996 | A61F 2/38 |
| GB | 2304051 | 3/1997 | A61F 2/38 |

(56) References Cited

FOREIGN PATENT DOCUMENTS

| | | | |
|---|---|---|---|
| GB | 2348373 | 10/2000 | ............... A61F 2/38 |
| JP | 56-083343 | 7/1981 | ............... A61F 1/03 |
| JP | 61-247448 | 11/1986 | ............... A61F 2/30 |
| JP | 1-249049 | 10/1989 | ............... A61F 2/38 |
| JP | 05-184612 | 7/1993 | ............... A61F 2/30 |
| JP | 7-236648 | 9/1995 | ............... A61F 2/28 |
| JP | 8-173465 | 7/1996 | ............... A61F 2/38 |
| JP | 8-506042 | 7/1996 | ............... A61F 2/38 |
| JP | 9-108249 | 4/1997 | ............... A61F 2/38 |
| JP | 9-206322 | 8/1997 | ............... A61F 2/36 |
| JP | 11-19104 | 1/1999 | ............... A61F 2/28 |
| JP | 11-276510 | 10/1999 | ............... A61F 2/28 |
| JP | 2007-521881 | 8/2007 | ............... A61F 2/44 |
| WO | WO 87/02882 | 5/1987 | ............... A61F 2/38 |
| WO | WO 90/09769 | 9/1990 | ............... A61F 2/28 |
| WO | WO 92/03108 | 3/1992 | ............... A61F 2/38 |
| WO | WO 93/04710 | 3/1993 | ............... A61L 25/00 |
| WO | WO 93/09819 | 5/1993 | ............... A61L 27/00 |
| WO | WO 93/25157 | 12/1993 | ............... A61B 17/56 |
| WO | WO 95/27450 | 10/1995 | ............... A61F 2/38 |
| WO | WO 95/28688 | 10/1995 | ............... G06T 15/00 |
| WO | WO 95/30390 | 11/1995 | ............... A61F 2/38 |
| WO | WO 95/32623 | 12/1995 | ............... A01N 1/02 |
| WO | WO 96/24302 | 8/1996 | ............... A61B 17/90 |
| WO | WO 97/25942 | 7/1997 | ............... A61F 2/32 |
| WO | WO 97/27885 | 8/1997 | ............... A61L 27/00 |
| WO | WO 97/29703 | 8/1997 | ............... A61B 17/56 |
| WO | WO 97/38676 | 10/1997 | ............... A61K 9/10 |
| WO | WO 97/46665 | 12/1997 | ............... C12N 5/06 |
| WO | WO 98/08469 | 3/1998 | ............... A61F 2/30 |
| WO | WO 98/12994 | 4/1998 | ............... A61F 2/28 |
| WO | WO 98/20816 | 5/1998 | ............... A61F 2/38 |
| WO | WO 98/30617 | 7/1998 | ............... C08G 63/12 |
| WO | WO 98/52498 | 11/1998 | ............... A61F 2/28 |
| WO | WO 99/02654 | 1/1999 | ............... C12N 5/00 |
| WO | WO 99/08598 | 2/1999 | ............... A61B 8/00 |
| WO | WO 99/08728 | 2/1999 | ............... A61L 27/00 |
| WO | WO 99/42061 | 8/1999 | ............... A61F 2/38 |
| WO | WO 99/47186 | 9/1999 | ............... A61L 27/00 |
| WO | WO 99/51719 | 10/1999 | ............... C12M 3/00 |
| WO | WO 00/09179 | 2/2000 | ............... A61L 25/00 |
| WO | WO 00/13616 | 3/2000 | ............... A61F 2/38 |
| WO | WO 00/15153 | 3/2000 | ............... A61F 2/38 |
| WO | WO 00/19911 | 4/2000 | ............... A61B 17/02 |
| WO | WO 00/35346 | 6/2000 | ............... A61B 5/11 |
| WO | WO 00/48550 | 8/2000 | |
| WO | WO 00/59411 | 10/2000 | ............... A61F 2/38 |
| WO | WO 00/68749 | 11/2000 | ......... G05B 19/4099 |
| WO | WO 00/74554 | 12/2000 | |
| WO | WO 00/74741 | 12/2000 | ............... A61L 27/00 |
| WO | WO 00/76428 | 12/2000 | ............... A61F 2/38 |
| WO | WO 01/10356 | 2/2001 | ............... A16F 2/46 |
| WO | WO 01/17463 | 3/2001 | ............... A61F 2/30 |
| WO | WO 01/19254 | 3/2001 | ............... A61B 17/00 |
| WO | WO 01/35968 | 5/2001 | ............... A61K 35/00 |
| WO | WO 01/45764 | 6/2001 | ............... A61L 27/36 |
| WO | WO 01/68800 | 9/2001 | ............... C12M 3/00 |
| WO | WO 01/70142 | 9/2001 | ............... A61F 2/38 |
| WO | WO 01/77988 | 10/2001 | ............... G60F 19/00 |
| WO | WO 01/82677 | 11/2001 | |
| WO | WO 01/91672 | 12/2001 | ............... A61F 2/36 |
| WO | WO 02/02021 | 1/2002 | ............... A61B 17/56 |
| WO | WO 02/09623 | 2/2002 | ............... A61F 2/38 |
| WO | WO 02/22013 | 3/2002 | ............... A61B 5/55 |
| WO | WO 02/22014 | 3/2002 | ............... A61B 5/55 |
| WO | WO 02/23483 | 3/2002 | ............... A61B 5/55 |
| WO | WO 02/34310 | 5/2002 | ............... A61L 31/04 |
| WO | WO 02/36147 | 5/2002 | ............... A61K 31/04 |
| WO | WO 02/37423 | 5/2002 | ............... G06T 17/00 |
| WO | WO 02/061688 | 8/2002 | ............... G06T 17/00 |
| WO | WO 02/096268 | 12/2002 | |
| WO | WO 03/007788 | 1/2003 | |
| WO | WO 03/013373 | 2/2003 | ............... A61B 17/17 |
| WO | WO 03/037192 | 5/2003 | ............... A61B 17/15 |
| WO | WO 03/039377 | 5/2003 | ............... A61B 17/15 |
| WO | WO 03/047470 | 6/2003 | ............... A61F 2/34 |
| WO | WO 03/051210 | 6/2003 | ............... A61B 17/58 |
| WO | WO 03/061522 | 7/2003 | |
| WO | WO 03/099106 | 12/2003 | |
| WO | WO 2004/006811 | 1/2004 | ............... A61F 2/46 |
| WO | WO 2004/032806 | 4/2004 | ............... A61F 2/30 |
| WO | WO 2004/043305 | 5/2004 | ............... A61F 2/30 |
| WO | WO 2004/049981 | 6/2004 | ............... A61F 2/46 |
| WO | WO 2004/051301 | 6/2004 | ............... G01R 33/56 |
| WO | WO 2004/073550 | 9/2004 | |
| WO | WO 2005/002473 | 1/2005 | ............... A61F 2/38 |
| WO | WO 2005/016175 | 2/2005 | |
| WO | WO 2005/020850 | 3/2005 | |
| WO | WO 2005/051239 | 6/2005 | ............... A61F 2/08 |
| WO | WO 2005/051240 | 6/2005 | ............... A61F 2/08 |
| WO | WO 2005/067521 | 7/2005 | |
| WO | WO 2005/076974 | 8/2005 | |
| WO | WO 2006/012370 | 2/2006 | ............... B65D 45/04 |
| WO | WO 2006/058057 | 6/2006 | ............... A61F 2/38 |
| WO | WO 2006/060795 | 6/2006 | ............... A61B 17/17 |
| WO | WO 2006/065774 | 6/2006 | ............... A61F 2/44 |
| WO | WO 2006/092600 | 9/2006 | ............... A61B 19/00 |
| WO | WO 2007/041375 | 4/2007 | ............... A61F 2/38 |
| WO | WO 2007/062079 | 5/2007 | ............... A61F 2/30 |
| WO | WO 2007/092841 | 8/2007 | ............... A61B 17/15 |
| WO | WO 2007/106172 | 9/2007 | ............... A61F 2/38 |
| WO | WO 2007/109641 | 9/2007 | ............... A61F 2/30 |
| WO | WO 2008/021494 | 2/2008 | ............... G06F 19/00 |
| WO | WO 2008/055161 | 5/2008 | ............... A61F 2/44 |
| WO | WO 2008/101090 | 8/2008 | ............... A61F 2/38 |
| WO | WO 2008/117028 | 10/2008 | ............... A61B 17/15 |
| WO | WO 2008/157412 | 12/2008 | ............... A61B 17/17 |
| WO | WO 2009/068892 | 6/2009 | ............... A61C 9/00 |
| WO | WO 2009/105495 | 8/2009 | ............... A61F 2/38 |
| WO | WO 2009/140294 | 11/2009 | ............... A61F 2/30 |
| WO | WO 2010/099231 | 9/2010 | ............... A61B 2/38 |
| WO | WO 2010/099353 | 9/2010 | ............... A61F 2/30 |
| WO | WO 2010/099359 | 9/2010 | ............... A61F 2/00 |
| WO | WO 2010/140036 | 12/2010 | ............... A61F 2/38 |
| WO | WO 2010/151564 | 12/2010 | ............... A61F 2/38 |
| WO | WO 2011/028624 | 3/2011 | ............... A61F 2/38 |
| WO | WO 2011/056995 | 5/2011 | ............... A61F 2/38 |
| WO | WO 2011/072235 | 6/2011 | ............... A61F 2/38 |
| WO | WO 2011/075697 | 6/2011 | ............... A61F 2/38 |
| WO | WO 2011/101474 | 8/2011 | ............... G06F 19/00 |
| WO | WO 2012/027150 | 3/2012 | ............... G06F 19/00 |
| WO | WO 2012/027185 | 3/2012 | ............... G06T 17/00 |
| WO | WO 2012/112694 | 8/2012 | ............... A61B 6/00 |
| WO | WO 2012/112698 | 8/2012 | ............... A61F 2/30 |
| WO | WO 2012/112701 | 8/2012 | ............... A61F 2/30 |
| WO | WO 2012/112702 | 8/2012 | ............... A61F 2/30 |
| WO | WO 2013/020026 | 2/2013 | ............... A61F 2/30 |
| WO | WO 2013/025814 | 2/2013 | ............... A61F 2/38 |
| WO | WO 2013/056036 | 4/2013 | ............... A61F 2/38 |
| WO | WO 2013/131066 | 9/2013 | ............... A61F 2/38 |
| WO | WO 2013/152341 | 10/2013 | ............... A61F 2/38 |
| WO | WO 2014/035991 | 3/2014 | ............... A61B 17/56 |

OTHER PUBLICATIONS

Aragenson et al., "Is There a Place for Patellofemoral Arthroplasty?," Clinical Orthopaedics and Related Research No. 321, pp. 162-167 (1995).

Blum et al., "Knee Arthroplasty in Patients with Rheumatoid Arthritis," ANN. Rheum. Dis. 33 (1): 1-11 (1974).

Bogoch, et al., "Supracondylar Fractures of the Femur Adjacent to Resurfacing and Macintosh Arthroplasties of the Knee in Patients with Rheumatoid Arthritis," Clin. Orthop. (229):213-220 (Apr. 1988).

Brown, Ph.D., et al., "MRI Basic Principles and Applications", Second Ed., Mark A. Brown and Richard C. Semelka, 1999, Wiley-Liss Inc., Title Page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

Carr et al., "Surface Interpolation with Radial Basis Functions for Medical Imaging," IEEE Transactions on Medical Imaging, IEEE, Inc. New York, vol. 16, pp. 96-107 (Feb. 1997).

(56) References Cited

OTHER PUBLICATIONS

Clary et al., "Experience with the MacIntosh Knee Prosthesis," South Med. J. 65(3):265-272 (1972).
Conaty, et al., "Surgery of the Hip and Knee in Patients with Rheumatoid Arthritis," J. Bone Joint Surg. Am. 55(2):301-314 (1973).
DeWinter et al., "The Richards Type II Patellofemoral Arthroplasty", Acta Orthop Scand 2001; 72 (5): 487-490.
Ghelman et al., "Kinematics of the Knee After Prosthetic Replacements", Clin. Orthop. May 1975: (108): 149-157.
Hastings et al., "Double Hemiarthroplasty of the Knee in Rheumatoid Arthritis," A Survey of Fifty Consecutive Cases, J. Bone Joint Surg. Br. 55(1):112-118 (1973).
Henderson et al., "Experience with the Use of the Macintosh Prosthesis in Knees of Patients with Pheumatoid Arthritis," South. Med. J. 62(11):1311-1315 (1969).
Jessop et al., "Follow-up of the Macintosh Arthroplasty of the Knee Joint," Rheumatol Phys. Med. 11(5):217-224 (1972).
Kates, et al., "Experiences of Arthroplasty of the Rheumatoid Knee Using Macintosh Prostheses," Ann. Rheum. Dis. 28(3):328 (1969).
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Lam et al., "X-Ray Diagnosis: A Physician's Approach", Editor Lam, 1998, Springer-Verlag publishers, Title page and Table of Contents pgs. Only (ISBN 9813083247).
Leenslag et al., "A Porous Composite for Reconstruction of Meniscus Lesions," Biological and Biomechanical Perform. of Biomaterials, Elsevier Science Publishers Amsterdam pp. 147-152 (1986).
MacIntosh, "Arthroplasty of the Knee in Rheumatoid Arthritis," Proceedings and Reports of Councils and Assotions, J. Bone & Joint Surg., vol. 48B No. (1): 179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
McCollum et al., "Tibial Plateau Prosthesis in Arthroplasty of the Knee," J. Bone Joint Surg. Am. 1970 52(4):827-8 (Feb. 1996).
McKeever "The Classic Tibial Plateau Prosthesis," Clin. Orthop. Relat. Res. (192):3-12 (1985).
Nelson et al., "Arthroplasty and Arthrodesis of the Knee Joint," Orthop. Clin. North Am. 2 (1): 245-64 (1971).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "Macintosh Arthroplasty: A Long-Term Review," J. R. Coll. Surg. Edin. (192):199-201 (1988).
Potter, "Arthroplasty of the Knee With Tibial Metallic Implants of the McKeever and Macintosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and Macintosh Prostheses," J. Bone Joint Surg. Am. 54(1):1-24 (1972).
Ranawat et al., "Macintosh Hemiarthroplasty in Rheumatoid Knee," Acta Orthop Belg., 39 (1): 1-11 (1973).
Schorn et al., "Macintosh Arthroplasty in Rheumatoid Arthritis," Rheumatol Rehabil. Aug. 1978:17(3):155-163.
Slone et al., "Body Ct: A Practical Approach", Editor Slone, 1999 McGraw-Hill publishers, Title page and Table of Contents pgs. Only (ISBN 007058219).
Stauffer et al., "The MacIntosh Prosthesis. Prospective Clinical and Gait Evaluation," Arch. Surg. 110(6):717-720 (1975).
Stout et al., "X-Ray Structure Determination: A Practical Guide", $2^{nd}$ Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE—OMT. vol. 4322, pp. 87-97, 2001.
Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Wordsworth et al., "MacIntosh Arthroplasty for the Rheumatoid Knee: A 10-year Follow Up," Ann. Rheum. Dis. 44(11):738-741 (1985).
International Searching Authority, International Search Report—International Application No. PCT/US03/38158, dated Feb. 23, 2005, 7 pages.
International Searching Authority, International Search Report—International Application No. PCT/US04/39714, dated May 13, 2005, together with the Written Opinion of the International Searching Authority, 8 pages.
European Patent Office, Supplementary European Search Report—Application No. 04812273.3, dated Oct. 8, 2007, 5 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.
Adam et al., "MR Imaging of the Knee: Three-Dimensional Volume Imaging Combined with Fast Processing,"J. Compt. Asst. Tomogr., 13(6): 984-988 (1989).
Adams et al., "Quantitative Imaging of Osteoarthritis," Semin Arthritis Rheum, 20(6) Suppl. 2: 26-39 (Jun. 1991).
Ahmad et al., "Biomechanical and Topographic Considerations for Autologous Osteochondral Grafting in the Knee," Am J Sports Med, 29(2): 201-206 (Mar.-Apr. 2001).
Alexander, "Estimating the motion of bones from markers on the skin," University of Illinois at Chicago (Doctoral Dissertation) (1998).
Alexander et al., "Correcting for deformation in skin-based marker systems," Proceedings of the 3rd Annual Gait and Clinical Movement Analysis Meeting, San Diego, CA (1998).
Alexander et al., "Internal to external correspondence in the analysis of lower limb bone motion," Proceedings of the 1999 ASME Summer Bioengineering Conference, Big Sky, Montana (1999).
Alexander et al., "State estimation theory in human movement analysis," Proceedings of the ASME International Mechanical Engineering Congress (1998).
Alexander et al., "Optimization techniques for skin deformation correction," International Symposium on 3-D Human Movement Conference, Chattanooga, TN, (1998).
Alexander et al. "Dynamic Functional Imaging of the Musculoskeletal System," ASME Winter International Congress and Exposition, Nashville, TN (1999).

(56) References Cited

OTHER PUBLICATIONS

Allen et al., "Late degenerative changes after meniscectomy 5 factors affecting the knee after operations," J Bone Joint Surg 66B: 666-671 (1984).
Alley et al., "Ultrafast contrast-enhanced three dimensional MR Aagiography: State of the art," Radiographics 18: 273-285 (1998).
Andriacchi, "Dynamics of knee Malalignment," Orthop Clin North Am 25: 395-403 (1994).
Andriacchi, et al., "A point cluster method for in vivo motion analysis: Applied to a study of knee kinematics," J. Biomech Eng 120(12): 743-749 (1998).
Andriacchi, et al., "Methods for evaluating the progression of Osterarthiritis," Journal of Rehabilitation Research and Development 37(2): 163-170 (2000).
Andriacchi et al., "Gait analysis as a tool to assess joint kinetics biomechanics of normal and pathological human articulating joints," Nijhoff, Series E 93: 83-102 (1985).
Andriacchi et al., "In vivo measurement of six-degrees-of-freedom knee movement during functional testing," Transactions of the Orthopedic Research Society 698 (1995).
Aro et al., "Clinical Use of Bone Allografts," Ann Med 25:403-412 (1993).
Bashir, "Validation of Gadolinium-Enhanced MRI of FAF Measurement in Human Cartilage," Intl. Soc. Mag. Resonance Med. (1998).
Beaulieu et al., "Glenohumeral relationships during physiological shoulder motion and stress testing: Initial experience with open MRI and active Scan-25 plane registration," Radiology (1999).
Beaulieu et al., "Dynamic imaging of glenohumeral instability with open MRI," Int. Society for Magnetic Resonance in Medicine Sydney, Australia (1998).
Beckmann et al., "Noninvasive 3D MR Microscopy as Tool in Pharmacological Research: Application to a Model of Rheumatoid Arthritis," Magn Reson Imaging 13(7): 1013-1017 (1995).
Billet, Philippe, French Version—"Gliding Knee Prostheses—Analysis of Mechanical Failures", Thesis, Medical School of Marseilles, 1982, 64 pages.
Billet, Philippe, Translated Version—"Gliding Knee Prostheses—Analysis of Mechanical Failures", Thesis, Medical School of Marseilles, 1982, 93 pages.
Blazina et al., "Patellofemoral replacement: Utilizing a customized femoral groove replacement," 5(1)53-55 (1990).
Bobic, "Arthroscopic osteochondral autogaft transplantation in anterior cruciate ligament reconstruction: a preliminary clinical study," Knee Surg Sports Traumatol Arthrosc 3(4): 262-264 (1996).
Boe et al., "Arthroscopic partial meniscectomy in patients aged over 50," J. Bone Joint Surg 68B: 707 (1986).
Borthakur et al., "In Vivo Triple Quantum Filtered Sodium MRI of Human Articular Cartilage," Proc. Intl. Soc. Mag. Resonance Med., 7:549 (1999).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chrondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).

Butts et al., "Real-Time MR imaging of joint motion on an open MR imaging scanner," Radiological Society of North America, 83rd Scientific Assembly and Annual Meeting, Chicago, IL (1997).
Carano et al., "Estimation of Erosive Changes in Rheumatoid Arthritis by Temporal Multispectral Analysis," Proc. Intl. Soc. Mag. Resonance Med., 7:408 (1999).
Castriota-Scanderbeg et al., "Precision of Sonographic Measurement of Articular Cartilage: Inter-and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).
Clarke et al., "Human Hip Joint Geometry and Hemiarthroplasty Selection," The Hip. C.V. Mosby, St. Louis 63-89 (1975).
Cohen et al., "Knee cartilage topography, thickness, and contact areas from MRI: in-vitro calibration and in-vivo measurements," Osteoarthritis and Cartilage 7: 95-109 (1999).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "Entropy Mapping of Articular Cartilage", ISMRM Seventh Scientific Meeting, Philadelphia, PA (1999) T. 41, V. II.
Dardzinski et al., "T1-T2 Comparison in Adult Articular Cartilage," ISMRM Seventh Scientific Meeting, Philadelphia, PA (May 22-28, 1999).
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Theumatology, Oxford University Press 959-983 (1993).
Dougados et al., "Longitudinal radiologic evaluation of osteoarthritis of the knee," J Theumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).
Eckstein et al., "In Vivo Reproducibility of Three-Dimensional Cartilage Volume and Thickness Measurements With MR Imaging", AJR 170(3): 593-597 (1998).

(56) References Cited

OTHER PUBLICATIONS

Eckstein et al., "New Quantitative Approaches With 3-D MRI: Cartilage Morphology, Function and Degeneration", Medical Imaging International, Nov.-Dec. 1998.
Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).
Eckstein et al., Accuracy of Cartilage Volume and Thickness Measurements with Magnetic Resonance Imaging, Clin. Orthop. 1998; 352: 137-148 T. 60 V. II.
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—A Finite Element Analysis," Anat Embryol, 189: 545-552 (1994).
Eckstein et al., "The Morphology of Articular Cartilage Assessed by Magnetic Resonance Imaging: Reproducibility and Anatomical Correlation," Sur. Radiol Anat 16: 429-438 (1994).
Elting et al., "Unilateral frame distraction: proximal tibial valgus osteotomy for medial gonarthritis," Contemp Orthrop 27(6): 522-524 (1993).
Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms: Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).
Gandy et al., "One-Year Longitudinal Study of Femoral Cartilage Lesions in Knee Arthritis," Proc. Intl. Soc. Mag. Resonance Med., 7:1032 (1999).
Garrett, "Osteochondral allografts for reconstruction of articular defects of the knee," Instr Course Lect 47:517-522 (1998).
Gerscovich, "A Radiologist's Guide to the Imaging in the Diagnosis and Treatment of Developmental Dysplasia of the Hip," Skeletal Radiol 26: 447-456 (1997).
Ghosh et al., "Watershed Segmentation of High Resolution Articular Cartilage Images for Assessment of Osteoarthritis," International Society for Magnetic Resonance in Medicine, Philadelphia, (1999).
Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).
Graichen et al., "Three-Dimensional Analysis of the Width of the Subacromial Space in Healthy Subjects and Patients With Impingement Syndrome," American Journal of Roentgenology 172: 1081-1086 (1999).
Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).
Hardy et al., "Measuring the Thickness of Articular Cartilage From MR Images," J. Magnetic Resonance Imaging 13: 120-126 (2001).
Hardy et al., "The Influence of the Resolution and Contrast on Measuring the Articular Cartilage Volume in Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Hayes et al., "Evaluation of Articular Cartilage: Radiographic and Cross-Sectional Imaging Techniques," Radiographics 12: 409-428 (1992).
Henkelman, "Anisotropy of NMR Properties of Tissues", Magn Res Med. 32: 592-601 (1994).
Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold, "In Situ Measurement of Articular Cartilage Deformation in Intact Femorapatellar Joints Under Static Loading", Journal of biomechanics 32: 1287-1295 (1999).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe, "Surface Size, Curvature Analysis, and Assessment of Knee Joint Incongruity With MR Imaging In Vivo", Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radiol; 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket Location in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Johnson et al., "The distribution of load across the knee. A comparison of static and dynamic measurements," J. Bone Joint Surg 62B: 346-349 (1980).
Johnson, "In vivo contact kinematics of the knee joint: Advancing the point cluster technique," Ph.D. Thesis, University of Minnesota (1999).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).

(56) References Cited

OTHER PUBLICATIONS

Karvonen et al., "Articular Cartilage Defects of the Knee: Correlation Between Magnetic Resonance Imaging and Gross Pathology," Aim Rheum Dis. 49: 672-675 (1990).
Kass et al., "Snakes: Active contour models.," Int J Comput Vision 1: 321-331 (1988).
Kaufman et al., "Articular Cartilage Sodium content as a function of compression" Seventh Scientific Meeting of ISMRM, p. 1022, 1999 T. 105, V. III.
Klosterman et al., "T2 Measurements in Adult Patellar Cartilage at 1.5 and 3.0 Tesla," ISMRM Seventh Scientific Meeting, Philadelphia, PA, (May 22-28, 1999).
Knauss et al., "Self-Diffusion of Water in Cartilage and Cartilage Components as Studied by Pulsed Field Gradient NMR," Magnetic Resonance in Medicine 41:285-292 (1999).
Koh et al. "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance of the Superficial Tissue Layer for the Indentation Stiffness of Articular Cartilage," Med. Eng. Phys; 24(2): 99-103 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).
LaFortune et al., "Three dimensional kinematics of the human knee during walking," J. Biomechanics 25: 347-357 (1992).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).
Ledingham et al. "Factors affecting radiographic progression of knee osteoarthritis," Ann Rheum Dis 54: 53-58 (1995).
Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker coordinates using globals optimization with joint constraints," J Biomechanics 32: 129-134 (1999).
Lu et al., "In vitro degradation of porous poly(L-lactic acid) foams", Biomaterials, 21(15):1595-1605, Aug. 2000.
Lucchetti et al., "Skin movement artifact assessment and compensation in the estimation of knee-joint kinematics," J Biomechanics 31: 977-984 (1998).

Lusse et al., "Measurement of Distribution of Water Content of Human Articular Cartilage Based on Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).
Maki et al., "SNR improvement in NMR microscopy using DEFT," J Mag Res; pp. 482-492 (1988).
Marler et al., "Soft-Tissue Augmentation with Injectable Alginate and Syngeneic Fibroblasts", Plastic & Reconstructive Surgery, 105(6):2049-2058, May, 2000.
Marshall et al., "Quantitation of Articular Cartilage Using Magnetic Resonance Imaging and Three-Dimensional Reconstruction," J. Orthop. Res.; 13: 814-823 (1995).
Matsen, III et al., "Robotic Assistance in Orthopaedic Surgery: A Proof of Principle Using Distal Femoral Arthroplasty", Clinical Ortho. and Related Research, 296:178-186 (1993).
Mattila et al., "Massive Osteoarticular Knee Allografts: Structural Changes Evaluated with CT," Radiology; 196: 657-660 (1995).
Merkle et al., "A Transceiver Coil Assembly for Hetero-Nuclear Investigations of Human Breast at 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the carpophalangeal joints of the hand: accuracy and precision of three-dimensional MR imaging," AJR 165: 371-375 (1995).

(56) References Cited

OTHER PUBLICATIONS

Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment of Cartilage Volume in the Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Recht et al., "Accuracy of fat-suppressed three-dimensional spoiled gradient-echo FLASH MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an—dimensional digitized picture with applications," Pattern Recognition 27(11): 1551-1565 (1994).
Schipplein et al., "Interaction between active and passive knee stabilizers during level walking," J Orthop Res 9: 113-119 (1991).
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: an Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method for Quantifying Time Dependent Changes in MR Signal Intensity of Articular Cartilage as a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).

(56) References Cited

OTHER PUBLICATIONS

Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Tebben et al., "Three-Dimensional Computerized Reconstruction. Illustration of Incremental Articular Cartilage Thinning," Invest. Radiol. 32(8): 475-484 (1997).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000) 8:2127.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US2005/042421, dated May 18, 2006, together with the Written Opinion of the International Searching Authority, 7 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
International Searching Authority, International Search Report—International Application No. PCT/US06/38212, dated Apr. 22, 2008, together with the Written Opinion of the International Searching Authority, 7 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.

(56) References Cited

OTHER PUBLICATIONS

Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated Jun. 28, 2010, pertaining to U.S. Appl. No. 10/752,438, 9 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
CAOS, "MIS meets CAOS Spring 2005 Symposium Schedule", *CAOS Spring 2005 Symposium*, pp. 1-9, May 19, 2005.
Chelute et al., "Patient-Specific Template to Preserve Bone Stock in Total Knee Replacement: Preliminary Results", *15$^{th}$ Annual ISTA Symposium*, Sep. 2002, 1 page.
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
European Patent Office, Extended European Search Report European Application No. 06815884.9-2310, dated Sep. 14, 2010, 7 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.

(56) References Cited

OTHER PUBLICATIONS

United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10,764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.
United States Patent and Trademark Office, Notice of Allowance dated Aug. 5, 2011, pertaining to U.S. Appl. No. 10/764,010, 14 pages.
Sunstein Kann Murphy & Timbers LLP, Preliminary Amendment dated Aug. 12, 2011, pertaining to U.S. Appl. No. 13/017,886, 13 pages.
International Searching Authority, International Search Report—International Application No. PCT/US2010/055483, dated Jul. 28, 2011, together with the Written Opinion of the International Searching Authority, 9 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.

Sunstein Kann Murphy & Timbers LLP, Amendment dated Feb. 2, 2011 pertaining to U.S. Appl. No. 11/769,434, 44 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US12/59936 dated Jan. 9, 2013, together with the Written Opinion of the International Searching Authority, 11 pages.
European Patent Office, European Search Report—Application No. 10192339.9-1257, dated Jan. 23, 2013, 5 pages.
European Patent Office, Extended European Search Report—Application No. 10792589.3-2310, dated Feb. 7, 2013, 9 pages.
European Patent Office, Extended European Search Report—Application No. 10746859.7-1654 dated Mar. 4, 2013, 7 pages.
European Patent Office, Extended European Search Report—Application No. 12192903.8-1654 dated Apr. 17, 2013, 8 pages.
International Searching Authority, International Search Report—International Application No. PCT/US2009/036165, dated May 7, 2009, together with the Written Opinion of the International Searching Authority, 9 pages.
International Searching Authority, International Search Report—International Application No. PCT/US2012/025280 dated Oct. 25, 2012, together with the Written Opinion of the International Searching Authority, 11 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
European Patent Office, European Search Report—Application No. 12170854.9-1526, dated Oct. 9, 2012, 6 pages.
European Patent Office, Extended European Search Report—Application No. 10836760.8-1654 dated Apr. 11, 2014, 6 pages.
International Searching Authority, International Search Report—International Application No. PCT/US2013/035536 dated Jul. 18, 2013, 3 pages.
International Searching Authority, International Search Report—International Application No. PCT/US2013/028762 dated Jun. 21, 2013, 9 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US13/56841 dated Feb. 12, 2014, together with the Written Opinion of the International Searching Authority, 9 pages.
International Searching Authority, International Search Report—International Application No. PCT/US2010/061141, dated Aug. 31, 2011, together with the Written Opinion of the International Searching Authority, 8 pages.
Cohen et al., "Computer-Aided Planning of Patellofemoral Joint OA Surgery: Developing Physical Models from Patient MRI", MICCAI, Oct. 11-13, 1998, 13 pages.
Delp et al., "A Graphics-Based Software System to Develop and Analyze Models of Musculoskeletal Structures," Comput. Biol. Med., vol. 25, No. 1, pp. 21-34, 1995.
Harryson et al., "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.

(56) References Cited

OTHER PUBLICATIONS

Lombardi, Jr. et al., "Patient-Specific Approach in Total Knee Arthroplasty", Orthopedics, vol. 31, Issue 9, Sep. 2008, 8 pages.
Overhoff et al., "Total Knee Arthroplasty: Coordinate System Definition and Planning Based on 3-D Ultrasound Image Volumes", CARS 2001, pp. 283-288.
Robinson et al., "The Early Innovators of Today's Resurfacing Condylar Knees", The Journal of Arthroplasty, vol. 20, No. 1, Suppl. 1, 2005.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
International Searching Authority, Great Britain Search and Examination Report—Application No. GB1201112.8 dated Feb. 3, 2014, 4 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2012/025277, dated Oct. 25, 2012, together with the Written Opinion of the International Searching Authority, 12 pages.
United States Patent and Trademark Office, Office Action dated Jul. 13, 2006, pertaining to U.S. Appl. No. 10/681,749, 6 pages.
Sunstein Kann Murphy & Timbers LLP, Response to Office Action dated Jul. 13, 2006, pertaining to U.S. Appl. No. 10/681,749, 21 pages.
United States Patent and Trademark Office, Office Action dated Jan. 9, 2007, pertaining to U.S. Appl. No. 10/681,749, 7 pages.
Sunstein Kann Murphy & Timbers LLP, Amendment to Office Action dated Jan. 9, 2007, pertaining to U.S. Appl. No. 10/681,749, 21 pages.
United States Patent and Trademark Office, Office Action dated Mar. 28, 2007, pertaining to U.S. Appl. No. 10/681,749, 6 pages.
Sunstein Kann Murphy & Timbers LLP, Response to Office Action dated Mar. 28, 2007, pertaining to U.S. Appl. No. 10/681,749, 25 pages.
United States Patent and Trademark Office, Office Action dated Dec. 14, 2007, pertaining to U.S. Appl. No. 10/681,749, 8 pages.
United States Patent and Trademark Office, Interview Summary dated Feb. 11, 2008, pertaining to U.S. Appl. No. 10/681,749, 2 pages.
Sunstein Kann Murphy & Timbers LLP, Request for Continued Examination and Response dated Feb. 29, 2008, pertaining to U.S. Appl. No. 10/681,749, 21 pages.
United States Patent and Trademark Office, Office Action dated May 20, 2008, pertaining to U.S. Appl. No. 10/681,749, 7 pages.
Sunstein Kann Murphy & Timbers LLP, Response to Office Action dated May 20, 2008, pertaining to U.S. Appl. No. 10/681,749, 18 pages.
United States Patent and Trademark Office, Office Action dated Nov. 13, 2008, pertaining to U.S. Appl. No. 10/681,749, 9 pages.
Sunstein Kann Murphy & Timbers LLP, Request for Continued Examination and Response dated May 13, 2009, pertaining to U.S. Appl. No. 10/681,749, 24 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Notice of Allowance and Fee(s) Due dated Feb. 25, 2010, pertaining to U.S. Appl. No. 10/681,749, 7 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Mar. 4, 2010, pertaining to U.S. Appl. No. 11/688,340, 22 pages.
United States Patent and Trademark Office, Office Action dated Dec. 6, 2010, pertaining to U.S. Appl. No. 11/688,340, 16 pages.
United States Patent and Trademark Office, Interview Summary dated May 23, 2011, pertaining to U.S. Appl. No. 11/688,340, 3 pages.
Sunstein Kann Murphy & Timbers LLP, Request for Continued Examination and Response dated Jun. 6, 2011, pertaining to U.S. Appl. No. 11/688,340, 23 pages.
United States Patent and Trademark Office, Office Action dated Jun. 17, 2014, pertaining to U.S. Appl. No. 11/688,340, 15 pages.
Sunstein Kann Murphy & Timbers LLP, Response to Office Action dated Jun. 17, 2014, pertaining to U.S. Appl. No. 11/688,340, 20 pages.
United States Patent and Trademark Office, Office Action dated Apr. 6, 2015, pertaining to U.S. Appl. No. 11/688,340, 15 pages.
Sunstein Kann Murphy & Timbers LLP, Request for Continued Examination and Response dated Oct. 6, 2015, pertaining to U.S. Appl. No. 11/688,340, 21 pages.
United States Patent and Trademark Office, Office Action dated Oct. 15, 2008, pertaining to U.S. Appl. No. 11/602,713, 10 pages.
Sunstein Kann Murphy & Timbers LLP, Response to Office Action dated Oct. 15, 2008, pertaining to U.S. Appl. No. 11/602,713, 17 pages.
United States Patent and Trademark Office, Office Action dated Jun. 9, 2009, pertaining to U.S. Appl. No. 11/602,713, 12 pages.
Sunstein Kann Murphy & Timbers LLP, Request for Continued Examination and Response dated Dec. 9, 2009, pertaining to U.S. Appl. No. 11/602,713, 15 pages.
United States Patent and Trademark Office, Office Action dated May 26, 2010, pertaining to U.S. Appl. No. 11/602,713, 10 pages.
Sunstein Kann Murphy & Timbers LLP, Response to Office Action dated May 26, 2010, pertaining to U.S. Appl. No. 11/602,713, 18 pages.
United States Patent and Trademark Office, Office Action dated Feb. 22, 2011, pertaining to U.S. Appl. No. 11/602,713, 10 pages.
Sunstein Kann Murphy & Timbers LLP, Request for Continued Examination and Response dated Aug. 22, 2011, pertaining to U.S. Appl. No. 11/602,713, 16 pages.
United States Patent and Trademark Office, Office Action dated Apr. 23, 2012, pertaining to U.S. Appl. No. 11/602,713, 13 pages.
Sunstein Kann Murphy & Timbers LLP, Response to Office Action dated Apr. 23, 2012, pertaining to U.S. Appl. No. 11/602,713, 15 pages.
United States Patent and Trademark Office, Office Action dated Oct. 26, 2012, pertaining to U.S. Appl. No. 11/602,713, 11 pages.
Sunstein Kann Murphy & Timbers LLP, Request for Continued Examination and Response dated Apr. 26, 2013, pertaining to U.S. Appl. No. 11/602,713, 18 pages.
United States Patent and Trademark Office, Office Action dated Oct. 29, 2013 pertaining to U.S. Appl. No. 11/602,713, 8 pages.
Sunstein Kann Murphy & Timbers LLP, Response to Office Action dated Oct. 29, 2013 pertaining to U.S. Appl. No. 11/602,713, 11 pages.
United States Patent and Trademark Office, Office Action dated Jun. 2. 2014, pertaining to U.S. Appl. No. 11/602,713, 8 pages.
Sunstein Kann Murphy & Timbers LLP, Request for Continued Examination and Response dated Dec. 2, 2014, pertaining to U.S. Appl. No. 11/602,713, 14 pages.
United States Patent and Trademark Office, Office Action dated Feb. 12, 2015, pertaining to U.S. Appl. No. 11/602,713, 8 pages.
Sunstein Kann Murphy & Timbers LLP, Request for Continued Examination and Response dated Aug. 12, 2015, pertaining to U.S. Appl. No. 11/602,713, 13 pages.
Buechel et al., "Meniscal-Bearing Total Knee Arthroplasty", Chapter 10 of Surgical Techniques in Total Knee Arthroplasty, pp. 81-89, 2002.

(56) References Cited

OTHER PUBLICATIONS

Delp et al., "Computer Assisted Knee Replacement", Clinical Orthopaedics, pp. 49-56, Sep. 1998.

Intergraph Corp. and Surgicad Corp., "Surgicad Design Combines 3-D Visualization with CAD Tools", Intergraph Corp. and Surgicad Corp. News Brief, 2 pages, Sep. 1993.

Mahaisavariya et al., "Morphological Study of the Proximal Femur: A New Method of Geometrical Assessment Using 3 Dimensional Reverse Engineering", Med. Eng. and Phys., vol. 24, pp. 617-622, 2002.

Müller-Wittig et al., "A Computer-Assisted Planning System for Total Knee Replacement", CG Topics, pp. 17-19, Jun. 2000.

Udupa et al., "3D Imaging in Medicine", Second Edition, pp. 84-86, 2000.

European Patent Office, European Search Report—European Application No. 12000991.5 dated May 23, 2014, 6 pages.

European Patent Office, Extended European Search Report—Application No. 12820490.6-1654, dated Jun. 26, 2015, 6 pages.

International Searching Authority, International Search Report—International Application No. PCT/US14/27446, dated Aug. 11, 2014, together with the Written Opinion of the International Searching Authority, 14 pages.

International Searching Authority, International Search Report—International Application No. PCT/US2014/023235 dated Sep. 24, 2014, together with the Written Opinion of the International Searching Authority, 15 pages.

International Searching Authority, International Search Report—International Application No. PCT/US2014/030015 dated Aug. 27, 2014, together with the Written Opinion of the International Searching Authority, 9 pages.

International Searching Authority, International Search Report—International Application No. PCT/US2014/031487 dated Sep. 2, 2014, together with the Written Opinion of the International Searching Authority, 17 pages.

Intellectual Property Office of Singapore, Search Report and Written Opinion dated Jun. 10, 2015, pertaining to Singapore Application No. 11201405753X, 33 pages.

Intellectual Property Office of Singapore, Search Report and Written Opinion dated Jun. 9, 2015, pertaining to Singapore Application No. 10201400158U, 15 pages.

\* cited by examiner

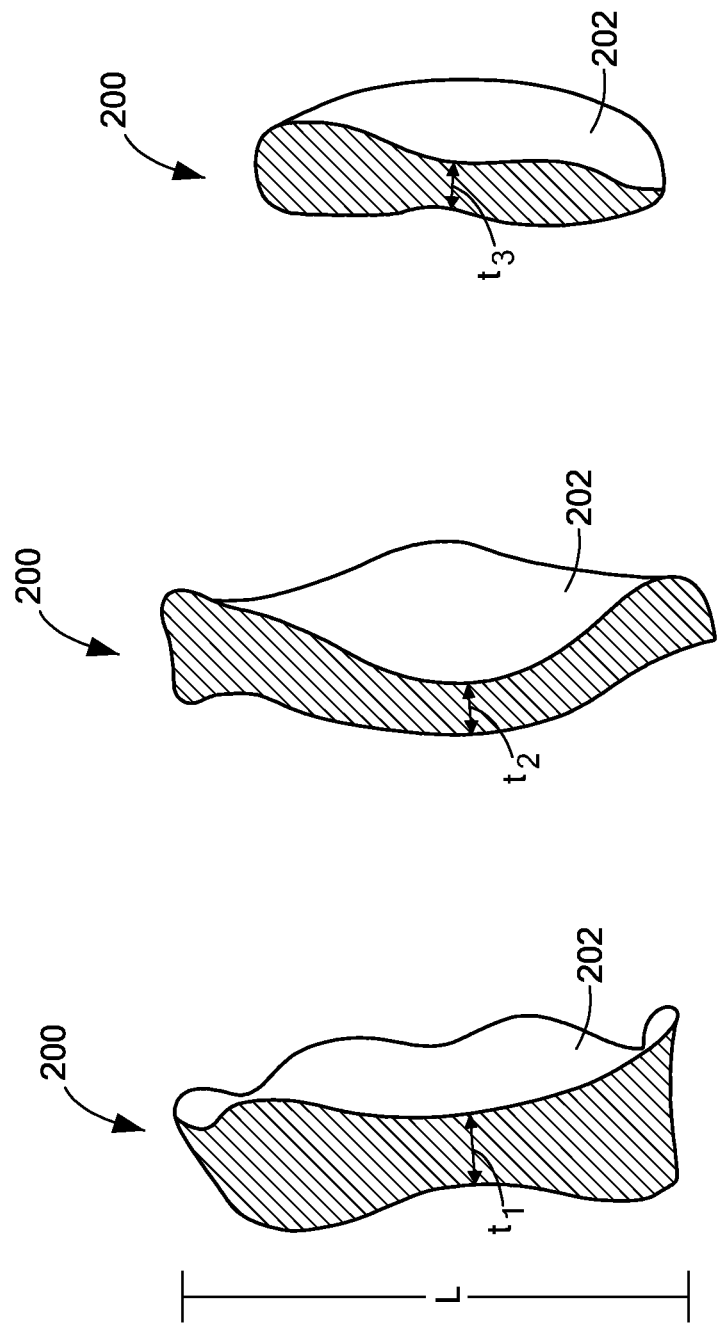
*FIG. 2C*  *FIG. 2D*  *FIG. 2E*

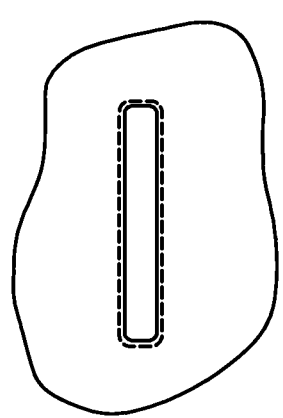
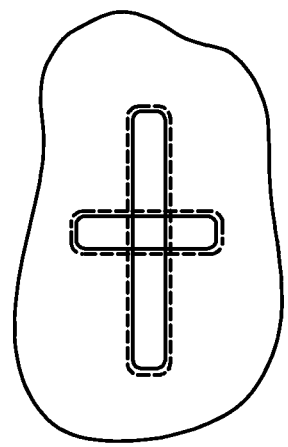
*FIG. 2N 2*     *FIG. 2O 2*
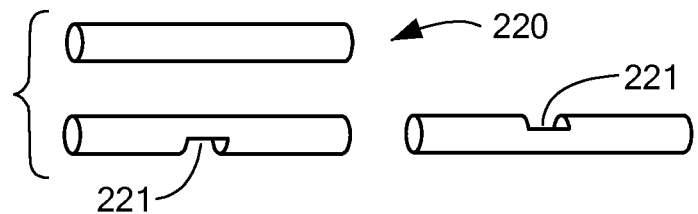
*FIG. 2P*
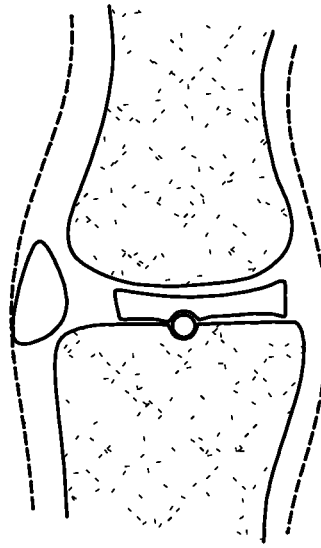
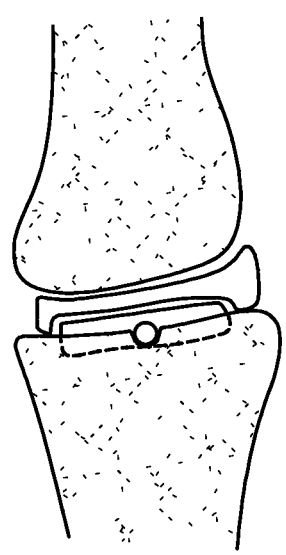
*FIG. 2Q*     *FIG. 2R*

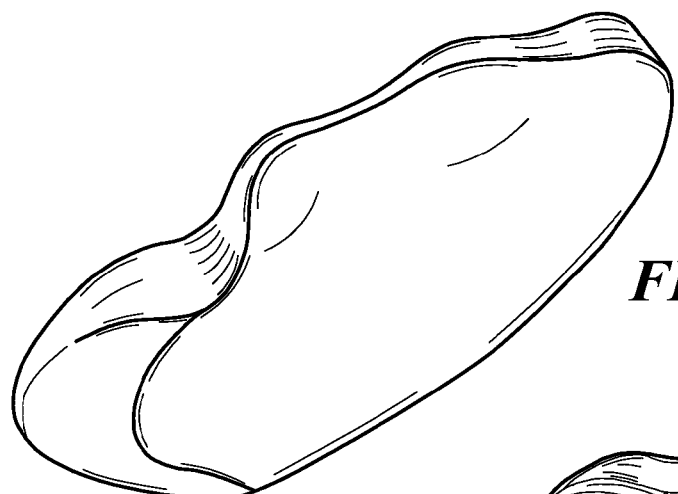
FIG. 2s-7
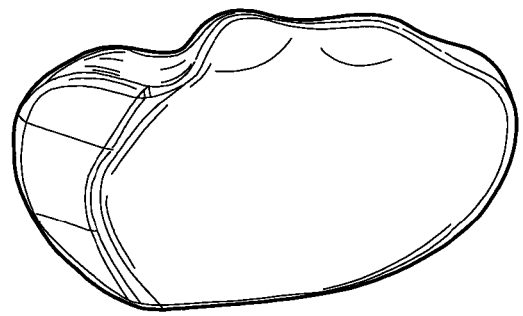
FIG. 2s-8
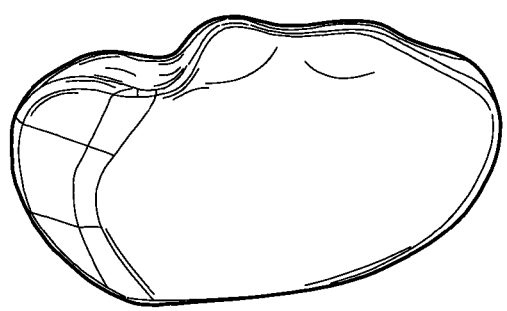
FIG. 2s-9
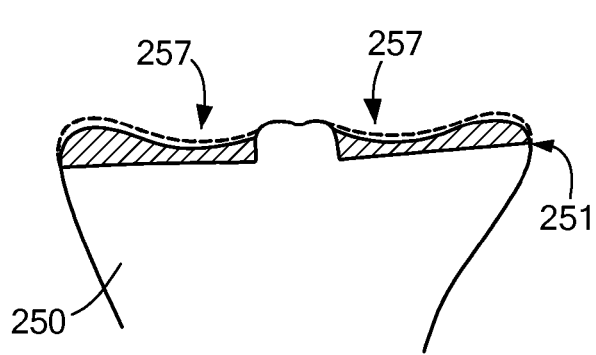
FIG. 2T(1)
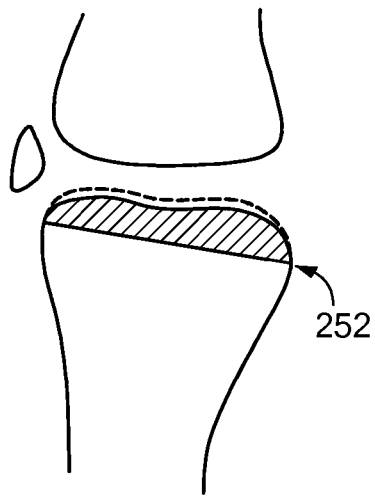
FIG. 2T(2)

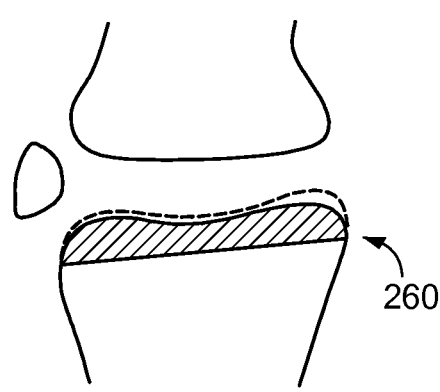
*FIG. 2T(3)*
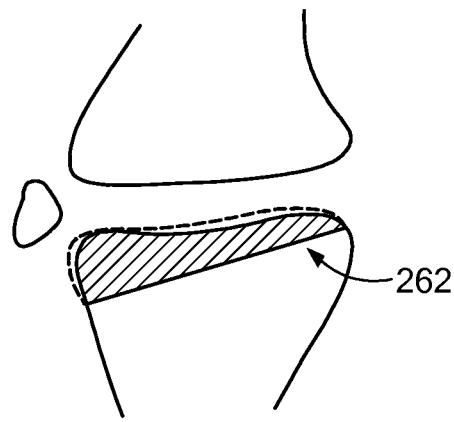
*FIG. 2T(4)*
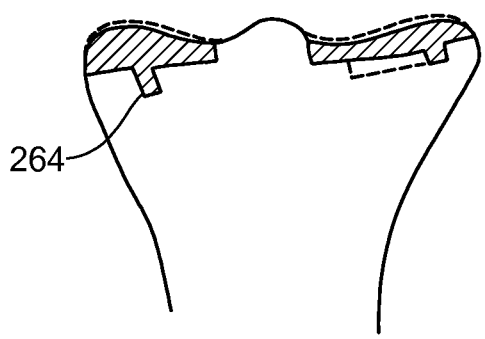
*FIG. 2T(5)*
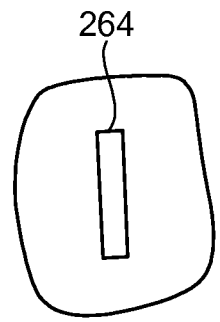
*FIG. 2T(6)*
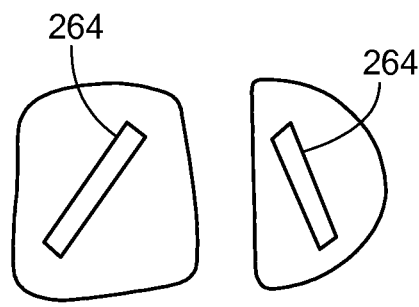
*FIG. 2T(7)*
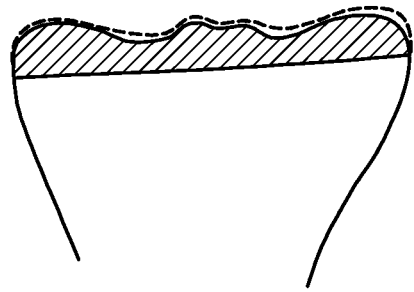
*FIG. 2T(8)*

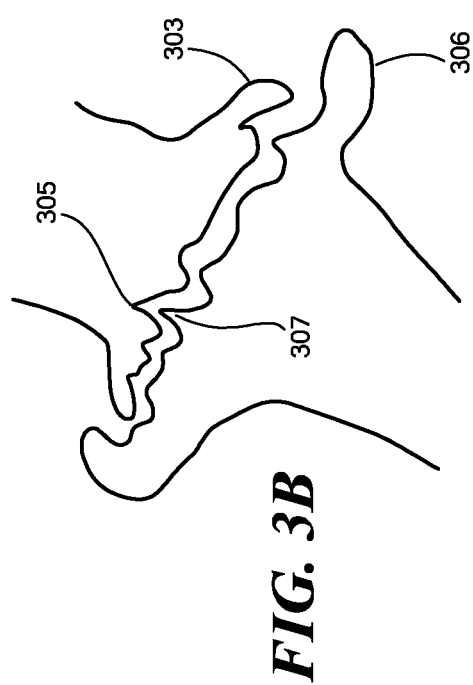
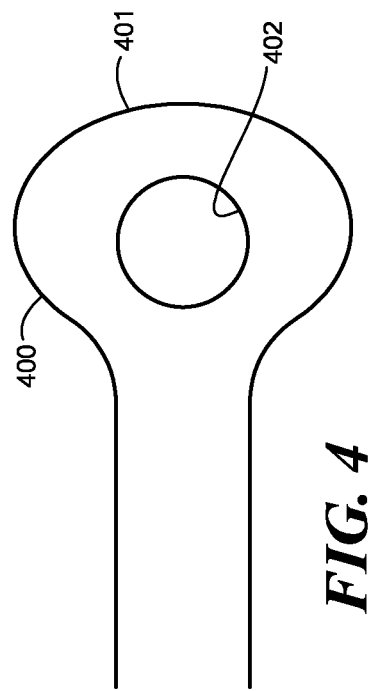
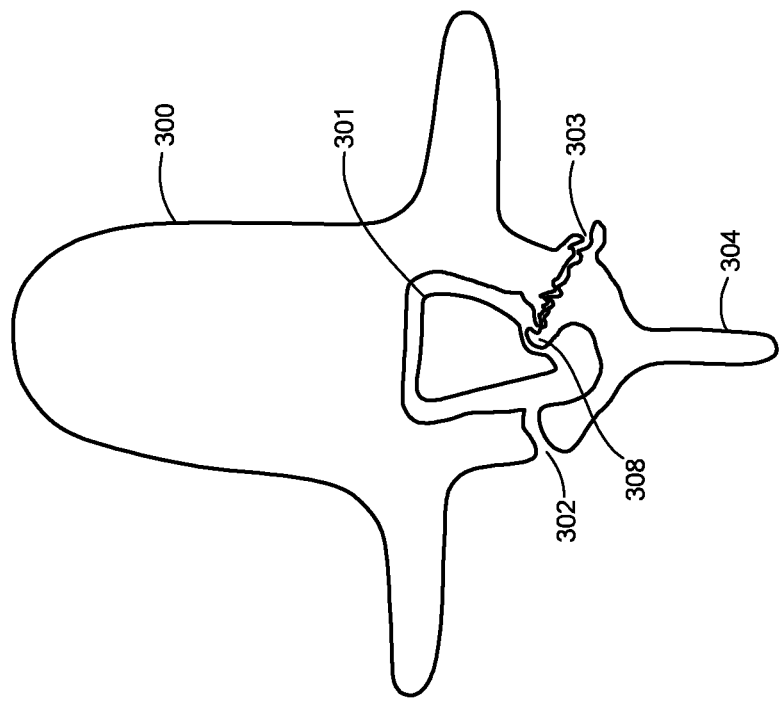
FIG. 3B
FIG. 4
FIG. 3A

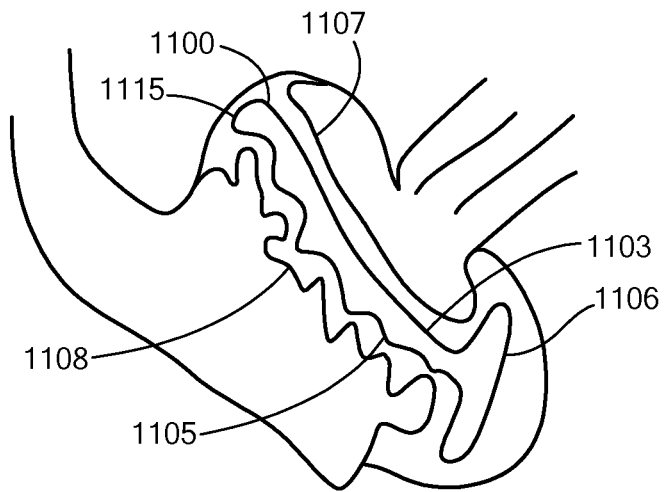
FIG. 11
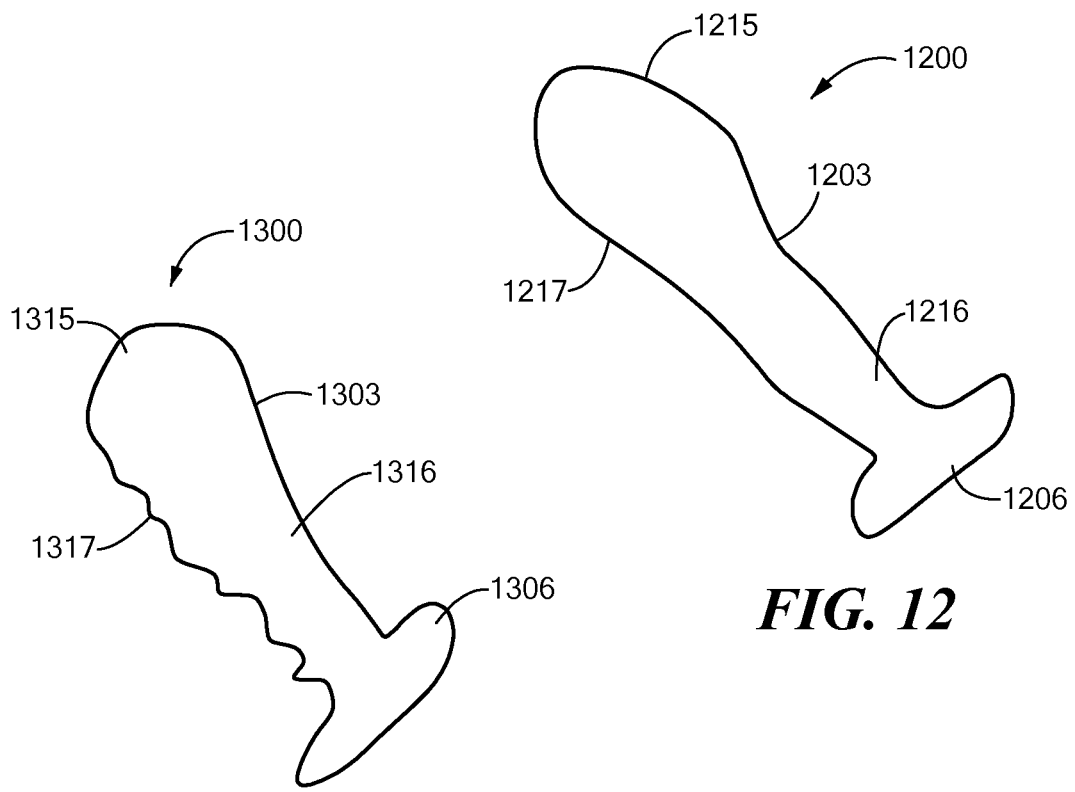
FIG. 12
FIG. 13

DEVICES AND METHODS FOR TREATMENT OF FACET AND OTHER JOINTS

CROSS-REFERENCE TO RELATED APPLICATIONS

The current application claims the benefit of U.S. provisional patent application 61/052,468 filed on May 12, 2008, entitled "Treatment of Facet Joint Disease", which is incorporated herein by reference in its entirety.

The current application is also a continuation-in-part of U.S. patent application Ser. No. 11/602,713 filed Nov. 21, 2006 and entitled "Devices and Methods for Treating Facet Joints, Uncovertebral Joints, Costovertebral Joints and Other Joints," which claims priority to U.S. provisional patent application 60/740,323 filed Nov. 21, 2005, entitled "Devices and Methods for Treating Facet Joints, Uncovertebral Joints, Costovertebral Joints and Other Joints." U.S. Ser. No. 11/602,713 is also a continuation-in-part of U.S. Ser. No. 10/997,407, filed Nov. 24, 2004 entitled "PATIENT SELECTABLE KNEE JOINT ARTHROPLASTY DEVICES," which is a continuation-in-part of U.S. Ser. No. 10/752,438, filed Jan. 5, 2004 which is a continuation-in-part of U.S. application Ser. No. 10/724,010 filed Nov. 25, 2003 entitled "PATIENT SELECTABLE JOINT ARTHROPLASTY DEVICES AND SURGICAL TOOLS FACILITATING INCREASED ACCURACY, SPEED AND SIMPLICITY IN PERFORMING TOTAL AND PARTIAL JOINT ARTHROPLASTY," which is a continuation-in-part of U.S. Ser. No. 10/305,652 entitled "METHODS AND COMPOSITIONS FOR ARTICULAR REPAIR," filed Nov. 27, 2002, which is now U.S. Pat. No. 7,468,075, which is a continuation-in-part of U.S. Ser. No. 10/160,667, filed May 28, 2002, which in turn claims the benefit of U.S. Ser. No. 60/293,488 entitled "METHODS TO IMPROVE CARTILAGE REPAIR SYSTEMS", filed May 25, 2001, U.S. Ser. No. 60/363,527, entitled "NOVEL DEVICES FOR CARTILAGE REPAIR, filed Mar. 12, 2002 and U.S. Ser. Nos. 60/380,695 and 60/380, 692, entitled "METHODS AND COMPOSITIONS FOR CARTILAGE REPAIR," and "METHODS FOR JOINT REPAIR," filed May 14, 2002. The current application is also a continuation-in-part of U.S. application Ser. No. 10/681, 750 filed Oct. 7, 2003 entitled "MINIMALLY INVASIVE JOINT IMPLANT WITH 3-DIMENSIONAL GEOMETRY MATCHING THE ARTICULAR SURFACES," which claim the benefit of U.S. provisional patent application 60/467,686 filed May 2, 2003 entitled "JOINT IMPLANTS." Each of the above-referenced applications is incorporated herein by reference in its entirety. Application Ser. No. 10/681,750 also claims the benefit of U.S. provisional patent application 60/416,601 filed Oct. 7, 2002 entitled "MINIMALLY INVASIVE JOINT IMPLANT WITH 3-DIMENSIONAL GEOMETRY MATCHING THE ARTICULAR SURFACES." The current application is also a continuation-in-part of U.S. application Ser. No. 10/681,749 filed Oct. 7, 2003 entitled "MINIMALLY INVASIVE JOINT IMPLANT WITH 3-DIMENSIONAL GEOMETRY MATCHING THE ARTICULAR SURFACES." The current application is also a continuation-in-part of U.S. application Ser. No. 10/704,208 filed Nov. 7, 2003 entitled "METHODS FOR DETERMINING MENISCAL SIZE AND SHAPE AND FOR DEVISING TREATMENT," which in turn claims the benefit of U.S. provisional patent application 60/424,964 filed Nov. 7, 2002 entitled "METHODS FOR DETERMINING MENISCAL SIZE AND SHAPE AND FOR DEVISING TREATMENT."

TECHNICAL FIELD

The present invention relates to orthopedic methods, systems and prosthetic devices and more particularly relates to methods, systems and devices associated with treatment of facet joints.

BACKGROUND ART

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on the joint and the site within the joint.

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type 11 collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. One approach includes the use of matrices, tissue scaffolds or other carriers implanted with cells (e.g., chondrocytes, chondrocyte progenitors, stromal cells, mesenchymal stem cells, etc.). These solutions have been described as a potential treatment for cartilage and meniscal repair or replacement. See, also, International Publications WO 99/51719 to Fofonoff, published Oct. 14, 1999; WO01/91672 to Simon et al., published Dec. 6, 2001; and WO01/17463 to Mannsmann, published Mar. 15, 2001; U.S. Pat. No. 6,283,980 B1 to Vibe-Hansen et al., issued Sep. 4, 2001, U.S. Pat. No. 5,842,477 to Naughton issued Dec. 1, 1998, U.S. Pat. No. 5,769,899 to Schwartz et al. issued Jun. 23, 1998, U.S. Pat. No. 4,609,551 to Caplan et al. issued Sep. 2, 1986, U.S. Pat. No. 5,041,138 to Vacanti et al. issued Aug. 29, 1991, U.S. Pat. No. 5,197,985 to Caplan et al. issued Mar. 30, 1993, U.S. Pat. No. 5,226,914 to Caplan et al. issued Jul. 13, 1993, U.S. Pat. No. 6,328,765 to Hardwick et al. issued Dec. 11, 2001, U.S. Pat. No. 6,281,195 to Rueger et al. issued Aug. 28, 2001, and U.S. Pat. No. 4,846,835 to Grande issued Jul. 11, 1989. However, clinical outcomes with biologic replacement materials such as allograft and autograft systems and tissue scaffolds have been uncertain since most of these materials do not achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g., for cosmetic repairs, or metal alloys. See, e.g., U.S. Pat. No. 6,383,228 to Schmotzer, issued May 7, 2002; U.S. Pat. No. 6,203,576 to Afriat et al., issued Mar. 20, 2001; U.S. Pat. No. 6,126,690 to Ateshian, et al., issued Oct. 3, 2000. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

Further, joint arthroplasties are highly invasive and require surgical resection of the entire articular surface of one or more bones, or a majority thereof. With these procedures, the marrow space is often reamed to fit the stem of the prosthesis. The reaming results in a loss of the patient's bone stock. U.S. Pat. No. 5,593,450 to Scott et al. issued Jan. 14, 1997 discloses an oval domed shaped patella prosthesis. The prosthesis has a femoral component that includes two condyles as articulating surfaces. The two condyles meet to form a second trochlear groove and ride on a tibial component that articulates with respect to the femoral component. A patella component is provided to engage the trochlear groove. U.S. Pat. No. 6,090,144 to Letot et al. issued Jul. 18, 2000 discloses a knee prosthesis that includes a tibial component and a meniscal component that is adapted to be engaged with the tibial component through an asymmetrical engagement.

A variety of materials can be used in replacing a joint with a prosthetic, for example, silicone, e.g. for cosmetic repairs, or suitable metal alloys are appropriate. See, e.g., U.S. Pat. No. 6,443,991 B1 to Running issued Sep. 3, 2002, U.S. Pat. No. 6,387,131 B1 to Miehike et al. issued May 14, 2002; U.S. Pat. No. 6,383,228 to Schmotzer issued May 7, 2002; U.S. Pat. No. 6,344,059 B1 to Krakovits et al. issued Feb. 5, 2002; U.S. Pat. No. 6,203,576 to Afriat et al. issued Mar. 20, 2001; U.S. Pat. No. 6,126,690 to Ateshian et al. issued Oct. 3, 2000; U.S. Pat. No. 6,013,103 to Kaufman et al. issued Jan. 11, 2000. Implantation of these prosthetic devices is usually associated with loss of underlying tissue and bone without recovery of the full function allowed by the original cartilage and, with some devices, serious long-term complications associated with the loss of significant amounts of tissue and bone can cause loosening of the implant. One such complication is osteolysis. Once the prosthesis becomes loosened from the joint, regardless of the cause, the prosthesis will then need to be replaced. Since the patient's bone stock is limited, the number of possible replacement surgeries is also limited for joint arthroplasty.

As can be appreciated, joint arthroplasties are highly invasive and require surgical resection of the entire, or a majority of, the articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, nonfunctional joint.

U.S. Pat. No. 6,206,927 to Fell, et al., issued Mar. 27, 2001, and U.S. Pat. No. 6,558,421 to Fell, et al., issued May 6, 2003, disclose a surgically implantable knee prosthesis that does not require bone resection. This prosthesis is described as substantially elliptical in shape with one or more straight edges. Accordingly, these devices are not designed to substantially conform to the actual shape (contour) of the remaining cartilage in vivo and/or the underlying bone. Thus, integration of the implant can be extremely difficult due to differences in thickness and curvature between the patient's surrounding cartilage and/or the underlying subchondral bone and the prosthesis. U.S. Pat. No. 6,554,866 to Aicher, et al. issued Apr. 29, 2003 describes a mono-condylar knee joint prosthesis.

Interpositional knee devices that are not attached to both the tibia and femur have been described. For example, Platt et al. (1969) "Mould Arthroplasty of the Knee," Journal of Bone and Joint Surgery 51B(1):76-87, describes a hemi-arthroplasty with a convex undersurface that was not rigidly attached to the tibia. Devices that are attached to the bone have also been described. Two attachment designs are commonly used. The McKeever design is a cross-bar member, shaped like a "t" from a top perspective view, that extends from the bone mating surface of the device such that the "t" portion penetrates the bone surface while the surrounding surface from which the "t" extends abuts the bone surface. See McKeever, "Tibial Plateau Prosthesis," Chapter 7, p. 86. An alternative attachment design is the Macintosh design, which replaces the "t" shaped fin for a series of multiple flat serrations or teeth. See Potter, "Arthroplasty of the Knee with Tibial Metallic Implants of the McKeever and Macintosh Design," Surg. Clins. Of North Am. 49(4): 903-915 (1969).

U.S. Pat. No. 4,502,161 to Wall issued Mar. 5, 1985, describes a prosthetic meniscus constructed from materials such as silicone rubber or Teflon with reinforcing materials of stainless steel or nylon strands. U.S. Pat. No. 4,085,466 to Goodfellow et al. issued Mar. 25, 1978, describes a meniscal component made from plastic materials. Reconstruction of meniscal lesions has also been attempted with carbon-fiber-polyurethane-poly (L-lactide). Leeslag, et al., Biological and Biomechanical Performance of Biomaterials (Christel et al., eds.) Elsevier Science Publishers B.V., Amsterdam. 1986. pp. 347-352. Reconstruction of meniscal lesions is also possible with bioresorbable materials and tissue scaffolds.

However, currently available devices do not always provide ideal alignment with the articular surfaces and the resultant joint congruity. Poor alignment and poor joint congruity can, for example, lead to instability of the joint.

Thus, there remains a need for compositions for repair of facet joints, uncovertebral joints, and costovertebral joints, among others. Further, there is a need for an implant or implant system that improves the anatomic result of the joint correction procedure by providing surfaces that more closely resemble the joint anatomy of a patient. Additionally, what is needed is an implant or implant system that provides an improved functional facet, uncovertebral, and costovertebral joint.

SUMMARY

The embodiments described herein provide novel devices and methods for replacing a portion (e.g., diseased area and/or area slightly larger than the diseased area) of a facet joint, uncovertebral joint, or costovertebral joint (e.g., cartilage, and/or bone) with one or more implants. In some embodiments, the implant(s) achieve an anatomic or near anatomic fit with the surrounding structures and tissues.

One embodiment is an interpositional device for use in a facet joint. The device includes a body that is configured to be inserted between the articular surfaces of the facet joint. The body has first and second articular surfaces and first and second ends. The first articular surface has contours configured to resist motion relative to an opposing articular surface when the device is inserted between articular surfaces of the facet joint. The second articular surface is configured to facilitate motion relative to another opposing articular surface when the device is inserted between articular surfaces of a facet joint.

Alternate embodiments may include one or more of the following features. The first end can be enlarged relative to a middle portion of the device. The first end can form a lip configured to engage at least one surface of the facet joint and thereby resist motion of the device relative to the facet joint. The first end can be configured to be located in an inter-articular position when the interpositional device is implanted in the facet joint, or, alternatively, the first end can be configured to be located in an extra-articular position when the interpositional device is implanted in the facet joint.

The contours of at least a portion of the first articular surface substantially can be made to conform to corresponding contours of the opposing articular surface. At least a portion of the first articular surface substantially can form a negative of a corresponding portion of the opposing articular surface. The first articular surface can be configured to secure the device when implanted in the facet joint. At least a portion of the first articular surface can be configured to interdigitate with a corresponding portion of the opposing articular surface when the device is implanted in the facet joint.

The second articular surface can be substantially smooth.

The second end can be enlarged relative to a middle portion of the device such that is enlarges a space between first and second surfaces of the facet joint.

The device can also include an attachment mechanism to secure the device in a facet join, for example, without limitation, a pin, fin, screw or suture.

Another embodiment is a patient-specific implant for use in a facet joint. The implant includes a body configured to be inserted between articular surfaces of the facet joint and that has first and second articular surfaces. At least a portion of the first articular surface substantially conforms to a corresponding portion of a first articular surface of the facet joint. The second articular surface has a substantially smooth portion configured to engage and move relative to a second articular surface of the facet joint when the implant is placed between the first and second articular surfaces of the facet joint.

Alternate embodiments may include one or more of the following features. The implant may include a first end that is enlarged relative to a middle portion of the device. The first end may form a cap configured to engage part of the facet joint and thereby resist motion of the device relative to the facet joint. The first end can be configured to be located in an inter-articular position when the interpositional device is implanted in the facet joint. The first end can alternatively be configured to be located in an extra-articular position when the interpositional device is implanted in the facet joint.

The first articular surface can be used to secure the device when implanted in the facet joint.

The device can further include first and second ends that are enlarged relative to a middle portion of the device.

The device can also include an attachment mechanism to secure the device in a facet joint, such as, without limitation, a pin, fin, or screw.

Another embodiment is an interpositional device for use in decompressing a portion of a spine. The device includes a body that can be inserted between articular surfaces of a facet joint. The body has first and second articular surfaces, a first end portion and a middle portion. The first articular surface is configured to move relative to an opposing articular surface when the device is in place. The first end portion has a thickness measured in a direction between the first and second articular surfaces that is larger than a corresponding thickness of the middle portion. The first end portion is configured to resist motion of the body relative to the facet joint in at least one direction when the interpositional device is implanted.

Alternate embodiments may include one or more of the following features. At least a portion of the second articular surface can include contours that substantially conform to corresponding contours of a second articular surface. At least a portion of the second articular surface can substantially form a negative of a corresponding portion of a second articular surface. The second articular surface can be configured to secure the device when implanted in the facet joint. At least a portion of the second articular surface can be configured to interdigitate with a corresponding portion of a second articular surface when the device is implanted in the facet joint.

The first articular surface can be substantially smooth.

Another embodiment is a device for use in relieving pressure on a portion of a spine. The device has a body configured to be inserted between articular surfaces of a facet joint. The body has first and second articular surfaces and an end portion. The first articular surface is configured to engage a corresponding first surface of the facet joint when the device is implanted. The second articular surface is configured to engage a corresponding second surface of the facet joint when the device is implanted. The end portion is relatively thicker in a direction between the first and second surfaces than an adjacent portion of the device, and thereby increases the spacing between the first and second surfaces of the facet joint when the device is implanted in the facet joint.

Another embodiment is a method for decompressing a portion of a spine. The method includes inserting an implant between first and second articular surfaces of a facet joint to expand a space between the articular surfaces; and stabilizing the implant in the facet joint such that the first and second surfaces remain in an expanded position for a period of time. As a result, the portion of the spine decompresses.

Alternate embodiments may include one or more of the following features. The pressure on an adjacent interstitial space of the spine can be reduced. Pain associated with pressure on the spine can be subsequently reduced.

BRIEF DESCRIPTION OF THE DRAWINGS

The FIG. 1A is a block diagram of a method for assessing a joint in need of repair according to embodiments of the invention wherein the existing joint surface is unaltered, or substantially unaltered, prior to receiving the selected implant.

FIG. 2C is a cross-sectional view of the implant of FIG. 2A along the lines 2C-2C shown in FIG. 2B.

FIG. 2D is a cross-sectional view along the lines 2D-2D shown in FIG. 2B.

FIG. 2E is a cross-sectional view along the lines 2E-2E shown in FIG. 2B.

FIG. 2P illustrates a variety of cross-bars.

FIGS. 2Q-R illustrate the device implanted within a joint.

FIG. 2T(1-8) illustrate an alternate embodiment of the tibial implant wherein the surface of the joint is altered to create a flat or angled surface for the implant to mate with.

FIG. 3A is an example of a cross-section of a vertebra demonstrating one normal and one degenerated facet joint.

FIG. 3B is an expanded view of the degenerated facet joint shown in FIG. 3A.

FIG. 11 shows a facet device for implantation into a facet joint, in accordance with one embodiment of the invention.

FIG. 12 shows a facet device having a dumbbell shape, in accordance with one embodiment of the invention.

FIG. 13 shows a facet device having a dumbbell shape, in accordance with one embodiment of the invention.

DETAILED DESCRIPTION

Figure 1A:
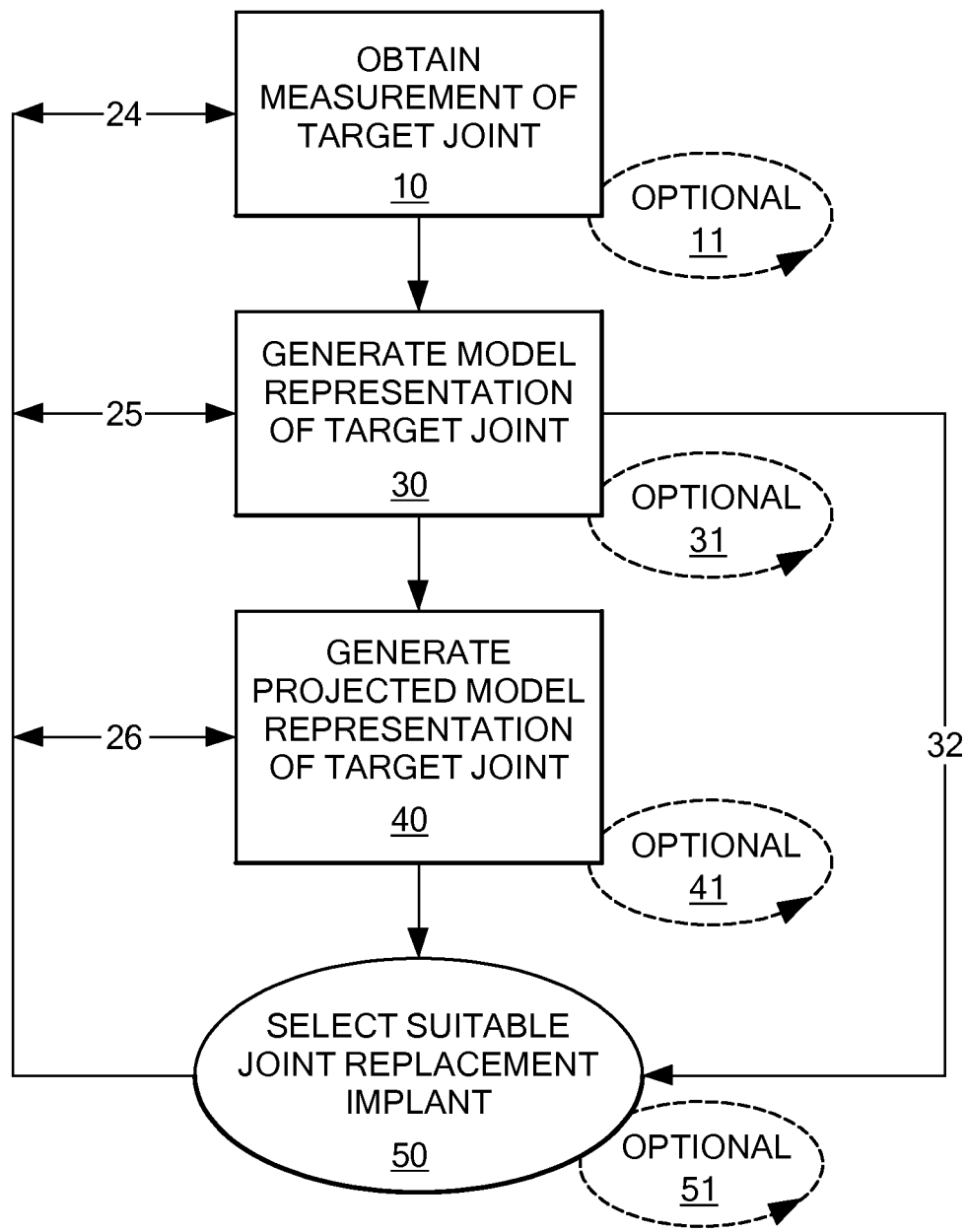
FIG. 1B is a block diagram of a method for assessing a joint in need of repair according to embodiments of the invention wherein the existing joint surface is unaltered, or substantially unaltered, prior to designing an implant suitable to achieve the repair.
FIG. 1C is a block diagram of a method for developing an implant and using the implant in a patient.
FIGS. 2N1-O1 and 2N2-O2 are alternative embodiments of the implant showing the lower surface have a trough for receiving a cross-bar.

The following description is presented to enable any person skilled in the art to make and use embodiments of the invention. Various modifications to the embodiments described will be readily apparent to those skilled in the art, and the generic principles defined herein can be applied to other embodiments and applications without departing from the spirit and scope of the present invention as defined by the appended claims. Thus, embodiments of the present invention are not intended to be limited to the embodiments shown, but are to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference in their entirety.

As will be appreciated by those of skill in the art, methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within embodiments of the invention. Also, it is contemplated that any optional feature of the inventive variations described may be set forth and claimed independently, or in combination with any one or more of the features described herein.

The practice of embodiments of the present invention can employ, unless otherwise indicated, conventional and digital methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging (2.sup.nd Ed.), Jerrold T. Bushberg, et al.

The present invention provides methods and compositions for repairing joints, particularly for repairing articular cartilage and subchondral bone and for facilitating the integration of a wide variety of cartilage and subchondral bone repair materials into a subject. Among other things, the techniques described herein allow for the customization of cartilage or subchondral bone repair material to suit a particular subject, for example in terms of size, cartilage thickness and/or curvature including subchondral bone curvature. When the shape (e.g., size, thickness and/or curvature) of the articular cartilage surface is an exact or near anatomic fit with the non-damaged cartilage or with the subject's original cartilage, the success of repair is enhanced. The repair material can be shaped prior to implantation and such shaping can be based, for example, on electronic images that provide information regarding curvature or thickness of any "normal" cartilage surrounding the defect and/or on curvature of the bone underlying the defect. Thus, embodiments of the invention provide, among other things, for minimally invasive methods for partial or complete joint replacement with attached and interpositional designs. The methods require only minimal or, in some instances, no loss in bone stock. Additionally, unlike with current techniques, the methods described herein will help to restore the integrity of the articular surface by achieving an exact or near anatomic match between the implant and the surrounding or adjacent cartilage and/or subchondral bone.

Advantages of embodiments of the present invention can include, but are not limited to, (i) optional customization of joint repair, thereby enhancing the efficacy and comfort level for the patient following the repair procedure; (ii) optional eliminating the need for a surgeon to measure the defect to be repaired intraoperatively in some embodiments; (iii) optional eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; (vi) improving postoperative joint congruity; (vii) improving the postoperative patient recovery in some embodiments and (viii) improving postoperative function, such as range of motion.

Thus, the methods described herein allow for the design and use of joint repair material that more precisely fits the defect (e.g. site of implantation) or the articular surface(s) and, accordingly, provides improved repair of the joint.

Assessment of Joints and Alignment

The methods and compositions described herein can be used to treat defects resulting from disease of the cartilage (e.g., osteoarthritis), bone damage, cartilage damage, trauma, and/or degeneration due to overuse or age. Embodiments of the invention allow, among other things, a health practitioner to evaluate and treat such defects. The size, volume and shape of the area of interest can include only the region of cartilage that has the defect, but preferably will also include contiguous parts of the cartilage surrounding the cartilage defect.

As will be appreciated by those of skill in the art, size, curvature and/or thickness measurements can be obtained using any suitable technique. For example, one-dimensional, two-dimensional, and/or three-dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated by those of skill in the art, the thickness of the repair device can vary at any given point depending upon patient's anatomy and/or the depth of the damage to the cartilage and/or bone to be corrected at any particular location on an articular surface.

FIG. 1A is a flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. It can include a physical model. More than one model can be created 31, if desired. Either the original model, or a subsequently created model, or both can be used. After the model representation of the joint is generated 30, the practitioner can optionally generate a projected model representation of the target joint in a corrected condition 40, e.g., from the existing cartilage on the joint surface, by providing a mirror of the opposing joint surface, or a combination thereof. Again, this step can be repeated 41, as necessary or desired. Using the difference between the topographical condition of the joint and the projected image of the joint, the practitioner can then select a joint implant 50 that is suitable to achieve the corrected joint anatomy. As will be appreciated by those of skill in the art, the selection process 50 can be repeated 51 as often as desired to achieve the desired result. Additionally, it is contemplated that a practitioner can obtain a measurement of a target joint 10 by obtaining, for example, an x-ray, and then select a suitable joint replacement implant 50.

As will be appreciated by those of skill in the art, the practitioner can proceed directly from the step of generating a model representation of the target joint 30 to the step of selecting a suitable joint replacement implant 50 as shown by the arrow 32. Additionally, following selection of suitable joint replacement implant 50, the steps of obtaining measurement of target joint 10, generating model representation of target joint 30 and generating projected model 40, can be repeated in series or parallel as shown by the flow 24, 25, 26.

Figure 1B:
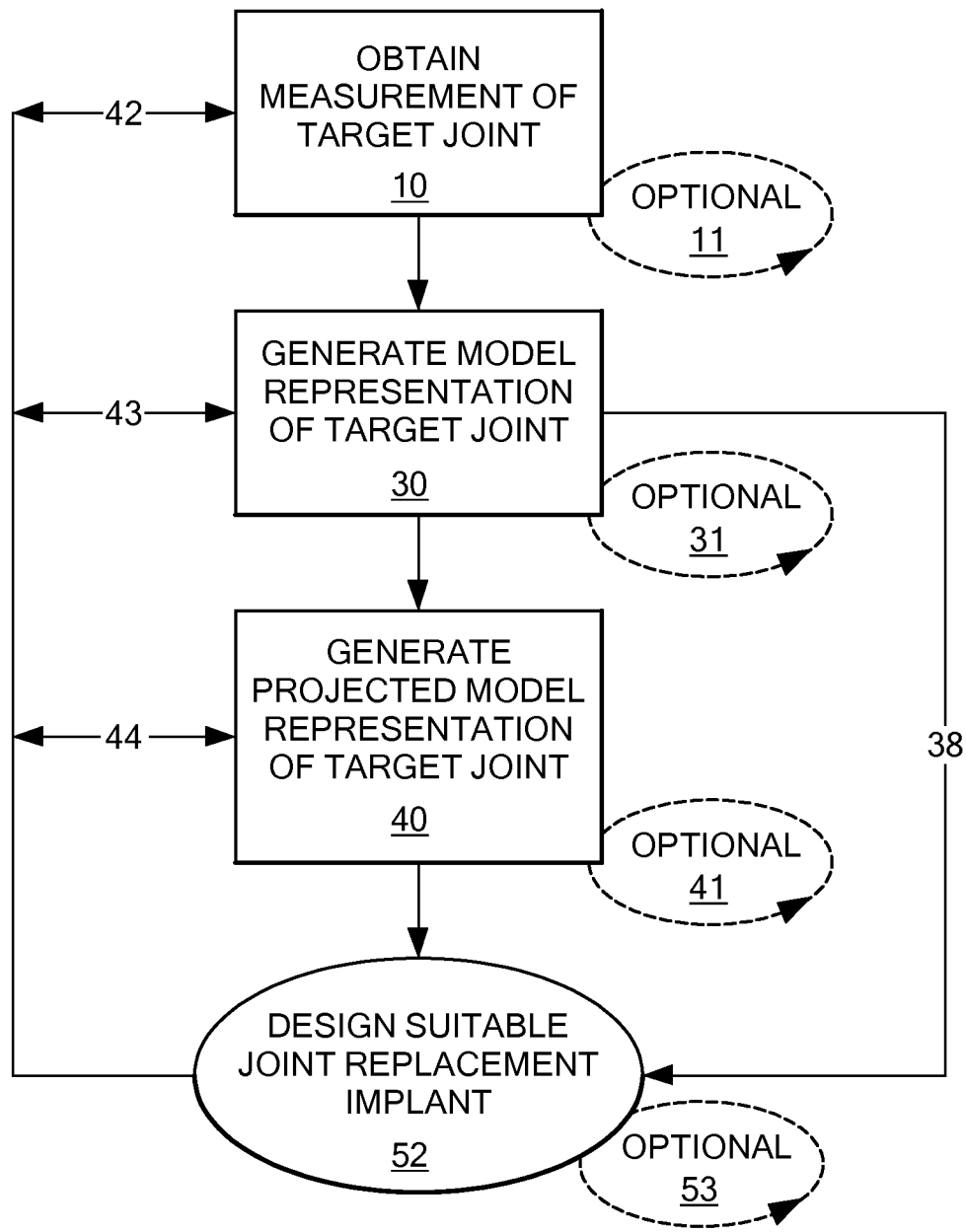

FIG. 1B is an alternate flow chart showing steps taken by a practitioner in assessing a joint. First, a practitioner obtains a measurement of a target joint 10. The step of obtaining a measurement can be accomplished by taking an image of the joint. This step can be repeated, as necessary, 11 to obtain a plurality of images in order to further refine the joint assessment process. Once the practitioner has obtained the necessary measurements, the information is used to generate a model representation of the target joint being assessed 30. This model representation can be in the form of a topographical map or image. The model representation of the joint can be in one, two, or three dimensions. The process can be repeated 31 as necessary or desired. It can include a physical model. After the model representation of the joint is assessed 30, the practitioner can optionally generate a projected model representation of the target joint in a corrected condition 40. This step can be repeated 41 as necessary or desired. Using the difference between the topographical condition of the joint and the projected image of the joint, the practitioner can then design a joint implant 52 that is suitable to achieve the corrected joint anatomy, repeating the design process 53 as often as necessary to achieve the desired implant design. The practitioner can also assess whether providing additional features, such as rails, keels, lips, pegs, cruciate stems, or anchors, cross-bars, etc. will enhance the implants' performance in the target joint.

As will be appreciated by those of skill in the art, the practitioner can proceed directly from the step of generating a model representation of the target joint 30 to the step of designing a suitable joint replacement implant 52 as shown by the arrow 38. Similar to the flow shown above, following the design of a suitable joint replacement implant 52, the steps of obtaining measurement of target joint 10, generating model representation of target joint 30 and generating projected model 40, can be repeated in series or parallel as shown by the flow 42, 43, 44.

Figure 1C:
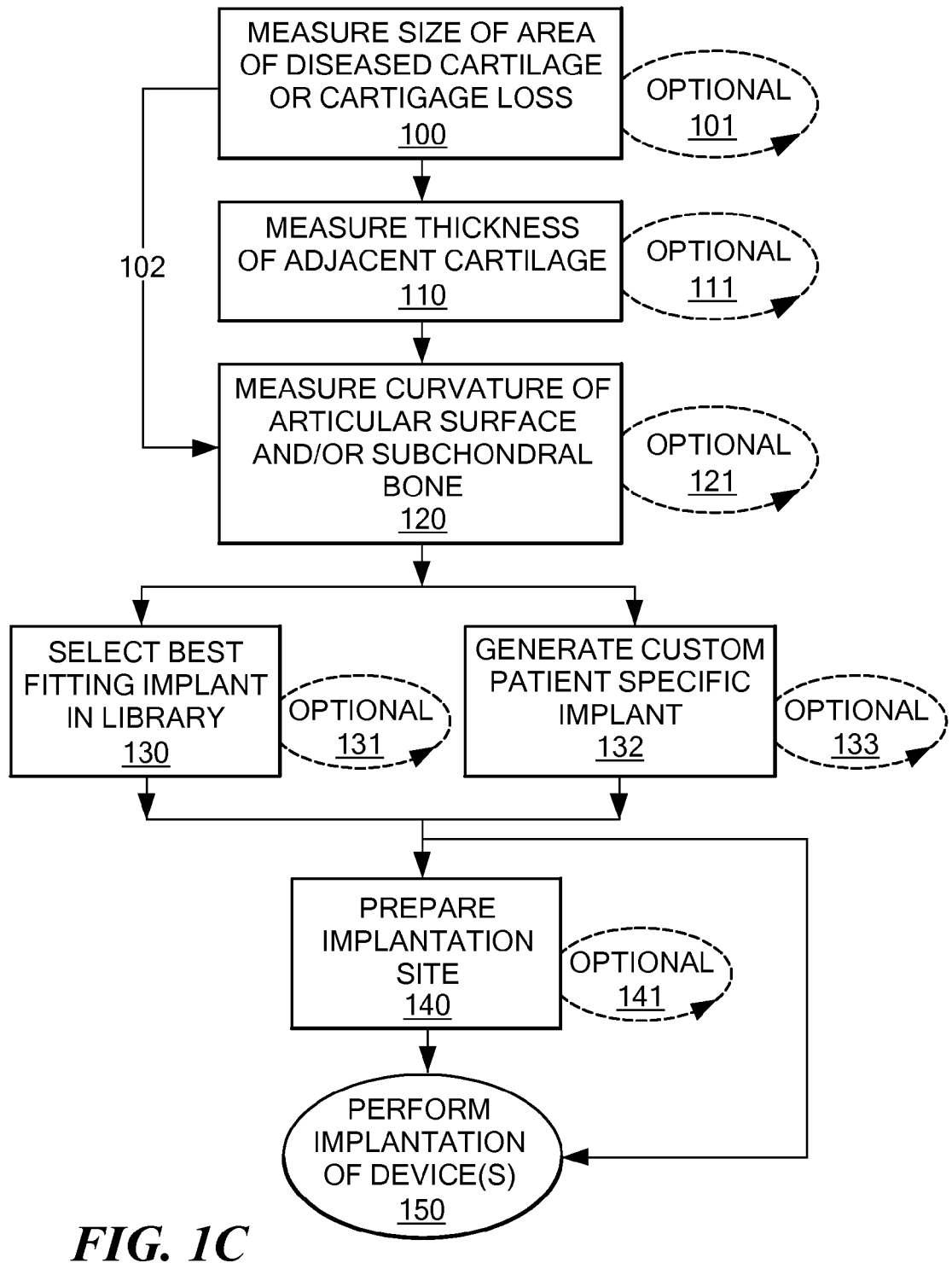

FIG. 1C is a flow chart illustrating the process of selecting an implant for a patient. First, using the techniques described above or those suitable and known in the art at the time embodiments of the invention are practiced, the size of area of diseased cartilage or cartilage loss is measured 100. This step can be repeated multiple times 101, as desired. Once the size of the cartilage defect is measured, the thickness of adjacent cartilage can optionally be measured 110. This process can also be repeated as desired 111. Either after measuring the cartilage loss or measuring the thickness of adjacent cartilage, the curvature of the articular surface is then measured 120. Alternatively, the subchondral bone can be measured. As will be appreciated measurements can be taken of the surface of the joint being repaired, or of the mating surface in order to facilitate development of the best design for the implant surface.

Once the surfaces have been measured, the user either selects the best fitting implant contained in a library of implants 130 or generates a patient-specific implant 132. These steps can be repeated as desired or necessary to achieve the best fitting implant for a patient, 131, 133. As will be appreciated by those of skill in the art, the process of selecting or designing an implant can be tested against the information contained in the MRI or x-ray of the patient to ensure that the surfaces of the device achieves a good fit relative to the patient's joint surface. Testing can be accomplished by, for example, superimposing the implant image over the image for the patient's joint. Once it has been determined that a suitable implant has been selected or designed, the implant site can be prepared 140, for example by removing cartilage or bone from the joint surface, or the implant can be placed into the joint 150.

The joint implant selected or designed achieves anatomic or near anatomic fit with the existing surface of the joint while presenting a mating surface for the opposing joint surface that replicates the natural joint anatomy. In this instance, both the existing surface of the joint can be assessed as well as the desired resulting surface of the joint. This technique is particularly useful for implants that are not anchored into the bone.

As will be appreciated by those of skill in the art, the physician, or other person practicing embodiments of the invention, can obtain a measurement of a target joint 10 and then either design 52 or select 50 a suitable joint replacement implant.

Repair Materials

A wide variety of materials find use in the practice of the present invention, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage or bone replacement or regenerating material having a curvature that will fit into a particular cartilage defect or onto a particular bone surface, will follow the contour and shape of the articular surface, and will optionally match the thickness of the surrounding cartilage. The repair material can include any combination of materials, and typically includes at least one non-pliable material, for example materials that are not easily bent or changed.

A. Metal and Polymeric Repair Materials

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat, et al. issued Mar. 20, 2001 and U.S. Pat. No. 6,322,588 to Ogle, et al. issued Nov. 27, 2001, and references cited therein. A wide-variety of metals are useful in the practice of embodiments of the present invention, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-nickel, iron alloys, cobalt alloys, such as Elgiloy®, a cobalt-chromium-nickel alloy, and MP35N, a nickel-cobalt-chromium-molybdenum alloy, and Nitinol®, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly (hydroxy butyrate), and similar copolymers can also be used.

Other materials would also be appropriate, for example, the polyketone known as polyetheretherketone (PEEK®). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of embodiments of the invention. The implant can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift U.S. Pat. No. 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

B. Biological Repair Material

Repair materials can also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. No. 5,478,739 to Slivka et al. issued Dec. 26, 1995; U.S. Pat. No. 5,842,477 to Naughton et al. issued Dec. 1, 1998; U.S. Pat. No. 6,283,980 to Vibe-Hansen et al., issued Sep. 4, 2001, and U.S. Pat. No. 6,365,405 to Salzmann et al. issued Apr. 2, 2002. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers can be bioresorbable.

Biological materials used in the methods described herein can be autografts (from the same subject); allografts (from another individual of the same species) and/or xenografts (from another species). See, also, International Patent Publications WO 02/22014 to Alexander et al. published Mar. 21, 2002 and WO 97/27885 to Lee published Aug. 7, 1997. In certain embodiments autologous materials are preferred, as they can carry a reduced risk of immunological complications to the host, including re-absorption of the materials, inflammation and/or scarring of the tissues surrounding the implant site.

In one embodiment of the invention, a probe is used to harvest tissue from a donor site and to prepare a recipient site. The donor site can be located in a xenograft, an allograft or an autograft. The probe is used to achieve a good anatomic match between the donor tissue sample and the recipient site. The probe is specifically designed to achieve a seamless or near seamless match between the donor tissue sample and the recipient site. The probe can, for example, be cylindrical. The distal end of the probe is typically sharp in order to facilitate tissue penetration. Additionally, the distal end of the probe is typically hollow in order to accept the tissue. The probe can have an edge at a defined distance from its distal end, e.g., at 1 cm distance from the distal end and the edge can be used to achieve a defined depth of tissue penetration for harvesting. The edge can be external or can be inside the hollow portion of the probe. For example, an orthopedic surgeon can take the probe and advance it with physical pressure into the cartilage, the subchondral bone and the underlying marrow in the case of a joint such as a knee joint. The surgeon can advance the probe until the external or internal edge reaches the cartilage surface. At that point, the edge will prevent further tissue penetration thereby achieving a constant and reproducible tissue penetration. The distal end of the probe can include one or more blades, saw-like structures, or tissue cutting mechanism. For example, the distal end of the probe can include an iris-like mechanism consisting of several small blades. The blade or blades can be moved using a manual, motorized or electrical mechanism thereby cutting through the tissue and separating the tissue sample from the underlying tissue. Typically, this will be repeated in the donor and the recipient. In the case of an iris-shaped blade mechanism, the individual blades can be moved so as to close the iris thereby separating the tissue sample from the donor site.

In another embodiment of the invention, a laser device or a radiofrequency device can be integrated inside the distal end of the probe. The laser device or the radiofrequency device can be used to cut through the tissue and to separate the tissue sample from the underlying tissue.

In one embodiment of the invention, the same probe can be used in the donor and in the recipient. In another embodiment, similarly shaped probes of slightly different physical dimensions can be used. For example, the probe used in the recipient can be slightly smaller than that used in the donor thereby achieving a tight fit between the tissue sample or tissue transplant and the recipient site. The probe used in the recipient can also be slightly shorter than that used in the donor thereby correcting for any tissue lost during the separation or cutting of the tissue sample from the underlying tissue in the donor material.

Any biological repair material can be sterilized to inactivate biological contaminants such as bacteria, viruses, yeasts, molds, mycoplasmas and parasites. Sterilization can be performed using any suitable technique, for example radiation, such as gamma radiation.

Any of the biological materials described herein can be harvested with use of a robotic device. The robotic device can use information from an electronic image for tissue harvesting.

In certain embodiments, the cartilage replacement material has a particular biochemical composition. For instance, the biochemical composition of the cartilage surrounding a defect can be assessed by taking tissue samples and chemical analysis or by imaging techniques. For example, WO 02/22014 to Alexander describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations. Biochemical composition of the cartilage replacement or regenerating material can, for example, be influenced by controlling concentrations and exposure times of certain nutrients and growth factors.

Device Design

A. Cartilage and Bone Models

Using information on thickness and curvature of the cartilage or underlying bone, a physical model of the surfaces of the articular cartilage and of the underlying bone can be created. This physical model can be representative of a limited area within the joint or it can encompass the entire joint. This model can also take into consideration the presence or absence of a meniscus as well as the presence or absence of some or all of the cartilage. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. This process takes into account that, for example, roughly 80% of patients have a healthy lateral component. As will be apparent, some, but not all, defects will include less than the entire cartilage. Thus, in one embodiment of the invention, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy (e.g., articular repair system) can be selected such that as much as possible of the healthy, surrounding tissue is preserved.

In other embodiments, the curvature of the articular surface or subchondral bone can be measured to design and/or shape the repair material. Further, both the thickness of the remaining cartilage and the curvature of the articular surface including bone can be measured to design and/or shape the repair material. Alternatively, the curvature of the subchondral bone can be measured and the resultant measurement(s) can be used to either select or shape a cartilage replacement material. For example, the contour of the subchondral bone can be used to re-create a virtual cartilage surface: the margins of an area of diseased cartilage can be identified. The subchondral bone shape in the diseased areas can be measured. A virtual contour can then be created by copying the subchondral bone surface into the cartilage surface, whereby the copy of the subchondral bone surface connects the margins of the area of diseased cartilage. In shaping the device, the contours can be configured to mate with existing cartilage or to account for the removal of some or all of the cartilage.

Figure 2A:
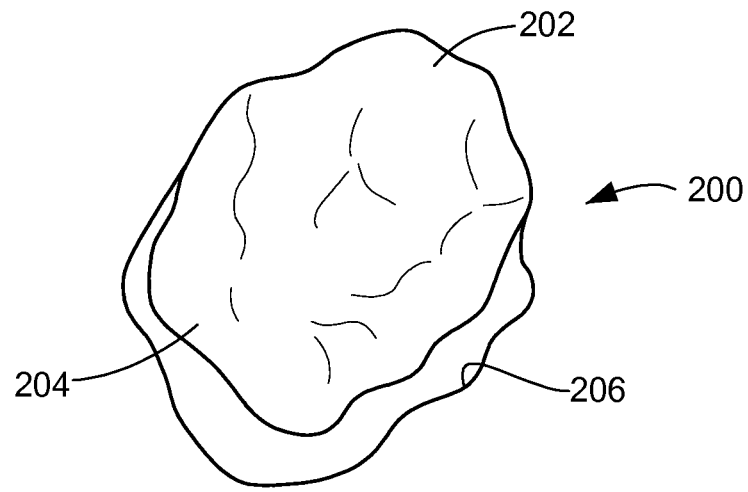
FIG. 2A is a perspective view of a joint implant of embodiments of the invention suitable for implantation in a joint.

FIG. 2A shows a slightly perspective top view of a joint implant 200 of one embodiment of the invention suitable for implantation in a joint such as a facet joint, an uncovertebral joint of a costovertebral joint. As shown in FIG. 2A, the implant can be generated using, for example, a dual surface assessment, as described above with respect to FIGS. 1A and B.

The implant 200 has an upper or frontal surface 202, a lower or posterior surface 204 and, optionally, a peripheral edge 206. The upper or frontal surface 202 is formed so that it forms a mating surface for receiving the opposing joint surface; in this instance partially concave to receive a femur, although other joints such as a facet joint, an uncovertebral joint or a costovertebral joint are possible. The concave surface can be variably concave such that it presents a surface to the opposing joint surface, e.g. a negative surface of the mating surface of the femur it communicates with. As will be appreciated by those of skill in the art, the negative impression need not be a perfect one.

The upper or frontal surface 202 of the implant 200 can be shaped by any of a variety of means. For example, the upper or frontal surface 202 can be shaped by projecting the surface from the existing cartilage and/or bone surfaces on the articular surface such as a tibial plateau or the surface of a facet joint, or it can be shaped to mirror the femoral condyle in order to optimize the complimentary surface of the implant when it engages the femoral condyle. Alternatively, the superior surface 202 can be configured to mate with an inferior surface of an implant configured for the opposing femoral condyle.

The lower or posterior surface 204 has optionally a convex surface that matches, or nearly matches, the surface of the joint, e.g. a tibial plateau or a facet or uncovertebral or costovertebral joint, such that it creates an anatomic or near anatomic fit with the tibial plateau or other relevant or applicable articular surface. Depending on the shape of the tibial plateau or applicable articular surface, the lower or posterior surface can be partially convex as well. Thus, the lower or posterior surface 204 presents a surface to the tibial plateau or applicable articular surface that fits within the existing surface. It can be formed to match the existing surface or to match the surface after articular resurfacing.

As will be appreciated by those of skill in the art, the convex surface of the lower or posterior surface 204 need not be perfectly convex. Rather, the lower or posterior surface 204 is more likely consist of convex and concave portions that fit within the existing surface of the tibial plateau or the re-surfaced plateau or re-surfaced applicable articular surface. Thus, the surface is essentially variably convex and concave.

Figure 2B:
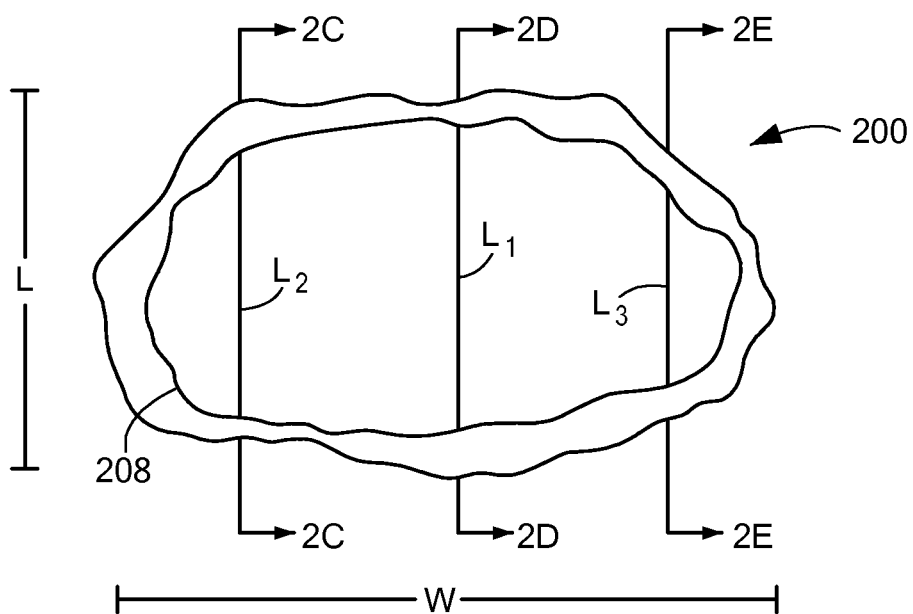
FIG. 2B is a top view of the implant of FIG. 2A.

FIG. 2B shows a top view of the joint implant of FIG. 2A. As shown in FIG. 2B the exterior shape 208 of the implant can be elongated. The elongated form can take a variety of shapes including elliptical, quasi-elliptical, race-track, etc. However, as will be appreciated the exterior dimension can be irregular thus not forming a true geometric shape, e.g., ellipse. As will be appreciated by those of skill in the art, the actual exterior shape of an implant can vary depending on the nature of the joint defect to be corrected. Thus, the ratio of the length L to the width W can vary from, for example, between about 0.25 to about 2.0, and more specifically from about 0.5 to about 1.5. As further shown in FIG. 2B, the length across an axis of the implant 200 varies when taken at points along the width of the implant. For example, as shown in FIG. 2B, $L_1 \neq L_2 \neq L_3$.

Turning now to FIGS. 2C-E, cross-sections of the implant shown in FIG. 2B are depicted along the lines of 2C-2C, 2D-2D, and 2E-2E. The implant has a thickness t1, t2 and t3 respectively. As illustrated by the cross-sections, the thickness of the implant varies along both its length L and width W. The actual thickness at a particular location of the implant 200 is a function of the thickness of the cartilage and/or bone to be replaced and the joint mating surface to be replicated. Further, the profile of the implant 200 at any location along its length L or width W is a function of the cartilage and/or bone to be replaced.

Figure 2F:
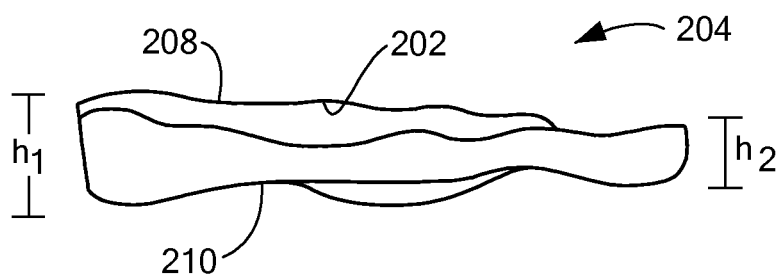
FIG. 2F is a side view of the implant of FIG. 2A.

FIG. 2F is a lateral view of the implant 200 of FIG. 2A. In this instance, the height of the implant 200 at a first end $h_1$ is different than the height of the implant at a second end $h_2$. Further the upper edge 208 can have an overall slope in a downward direction. However, as illustrated the actual slope of the upper edge 208 varies along its length and can, in some instances, be a positive slope. Further the lower edge 210 can have an overall slope in a downward direction. As illustrated the actual slope of the lower edge 210 varies along its length and can, in some instances, be a positive slope. As will be appreciated by those of skill in the art, depending on the anatomy of an individual patient, an implant can be created wherein $h_1$ and $h_2$ are equivalent, or substantially equivalent without departing from the scope of the invention.

Figure 2G:
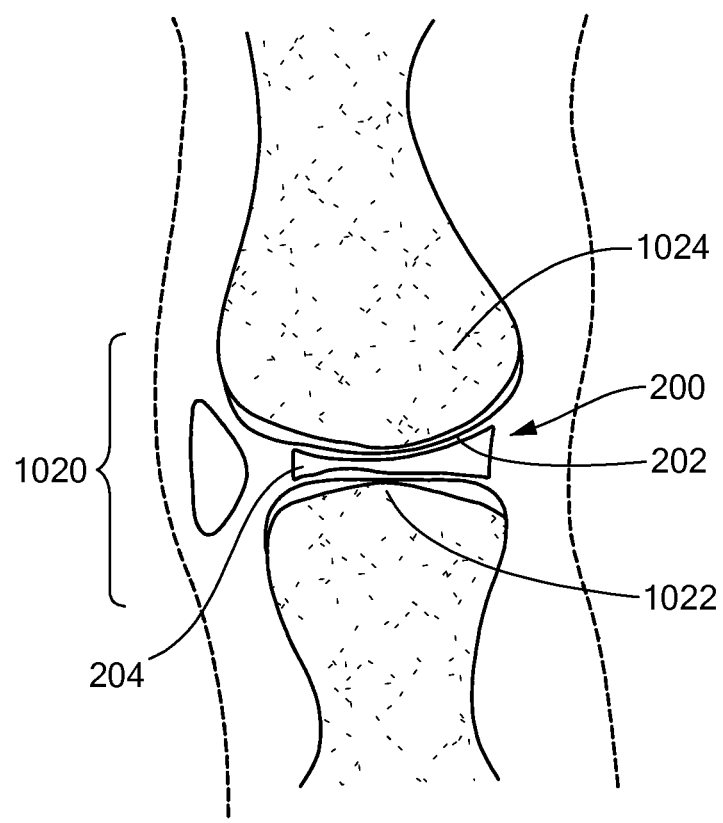
FIG. 2G is a cross-sectional view of the implant of FIG. 2A shown implanted taken along a plane parallel to the sagittal plane.
Figure 2H:
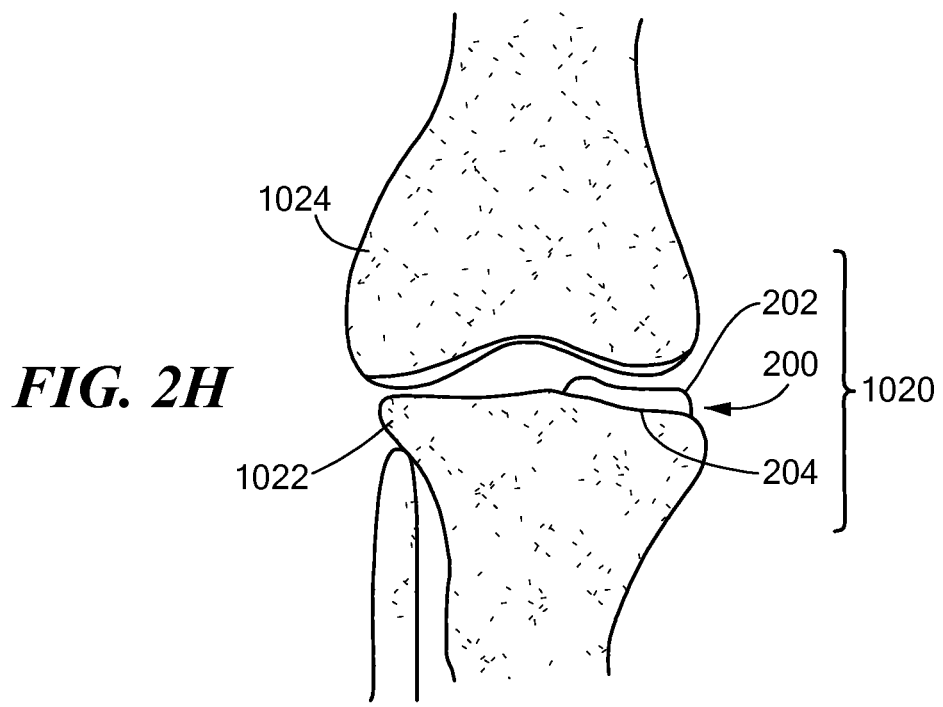
FIG. 2H is a cross-sectional view of the implant of FIG. 2A shown implanted taken along a plane parallel to the coronal plane.

FIG. 2G is a cross-section taken along a sagittal plane in a body showing the implant 200 implanted within a knee joint 1020 such that the lower surface 204 of the implant 200 lies on the tibial plateau 1022 and the femur 1024 rests on the upper surface 202 of the implant 200. FIG. 2H is a cross-section taken along a coronal plane in a body showing the implant 200 implanted within a knee joint 1020. As is apparent from this view, the implant 200 is positioned so that it fits within a superior articular surface 224. As will be appreciated by those of skill in the art, the articular surface could be the medial or lateral facet, as needed.

Figure 2I:
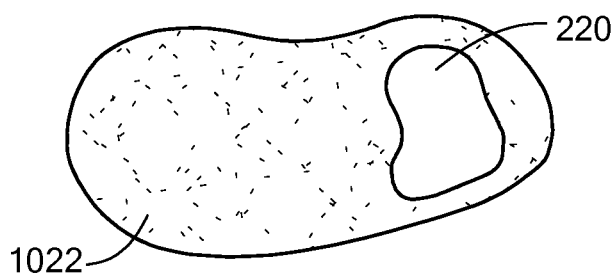
FIG. 2I is a cross-sectional view of the implant of FIG. 2A shown implanted taken along a plane parallel to the axial plane.
Figure 2J:
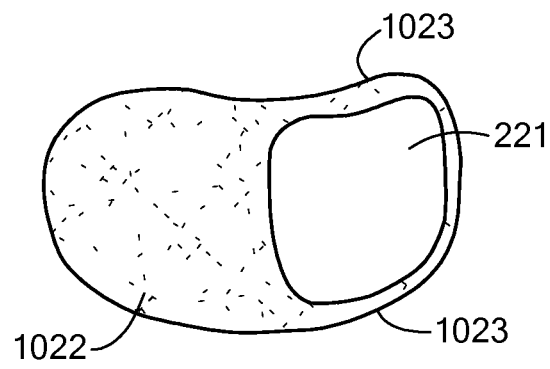
FIG. 2J shows a slightly larger implant that extends closer to the bone medially (towards the edge of the tibial plateau) and anteriorly and posteriorly.

FIG. 2I is a view along an axial plane of the body showing the implant 200 implanted within a knee joint 1020 showing the view taken from an aerial, or upper, view. FIG. 2J is a view of an alternate embodiment where the implant is a bit larger such that it extends closer to the bone medially, i.e., towards the edge 1023 of the tibial plateau, as well as extending anteriorly and posteriorly.

Figure 2K:
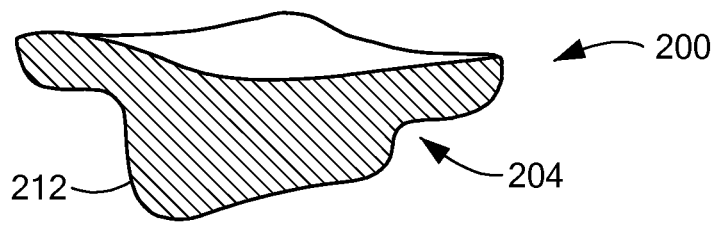
FIG. 2K is a side view of an alternate embodiment of the joint implant of FIG. 2A showing an anchor in the form of a keel.

FIG. 2K is a cross-section of an implant 200 of one embodiment of the invention, e.g., for a facet joint, an uncovertebral or a costovertebral joint, according to an alternate embodiment. In this embodiment, the lower surface 204 further includes a joint anchor 212. As illustrated in this embodiment, the joint anchor 212 forms a protrusion, keel or vertical member that extends from the lower surface 204 of the implant 200 and projects into, for example, the bone of the joint. As will be appreciated by those of skill in the art, the keel can be perpendicular or lie within a plane of the body.

Figure 2L:
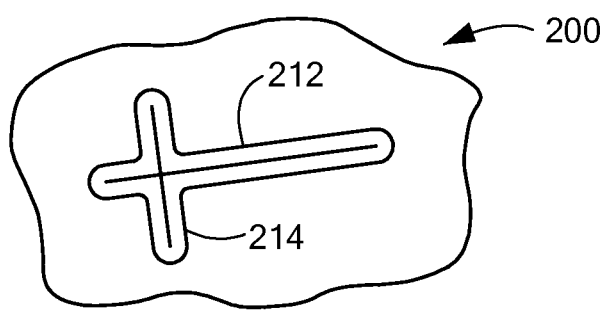
FIG. 2L is a bottom view of an alternate embodiment of the joint implant of FIG. 2A showing an anchor.
Figure 2M:
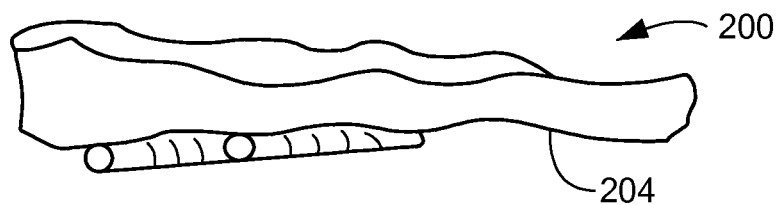
FIG. 2M shows an anchor in the form of a cross-member.

Additionally, as shown in FIG. 2L, the joint anchor 212 can have a cross-member 214 so that from a bottom perspective, the joint anchor 212 has the appearance of a cross or an "x." As will be appreciated by those of skill in the art, the joint anchor 212 could take on a variety of other forms while still accomplishing the same objective of providing increased stability of the implant 200 in the joint. These forms include, but are not limited to, pins, bulbs, balls, teeth, etc. Additionally, one or more joint anchors 212 can be provided as desired. FIGS. 2M and N illustrate cross-sections of alternate embodiments of a dual component implant from a side view and a front view.

Figure 2N:
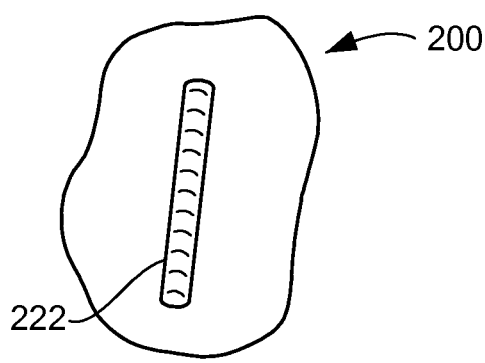
Figure 2O:
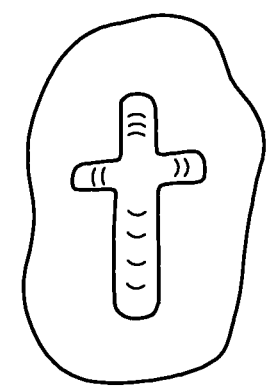
Figures 1, 2S:
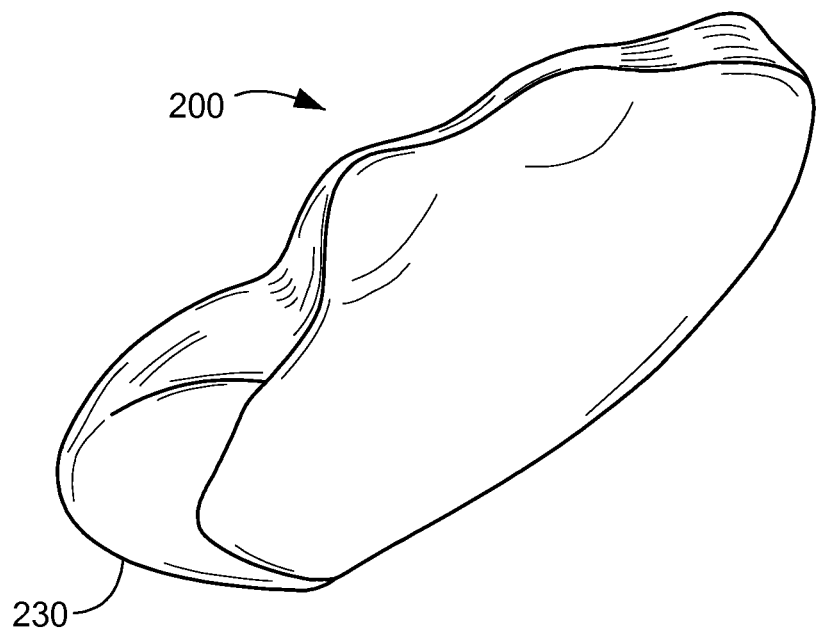
FIGS. 2S(1-9) illustrate another implant suitable for the tibial plateau further having a chamfer cut along one edge.
Figures 2, 2S:
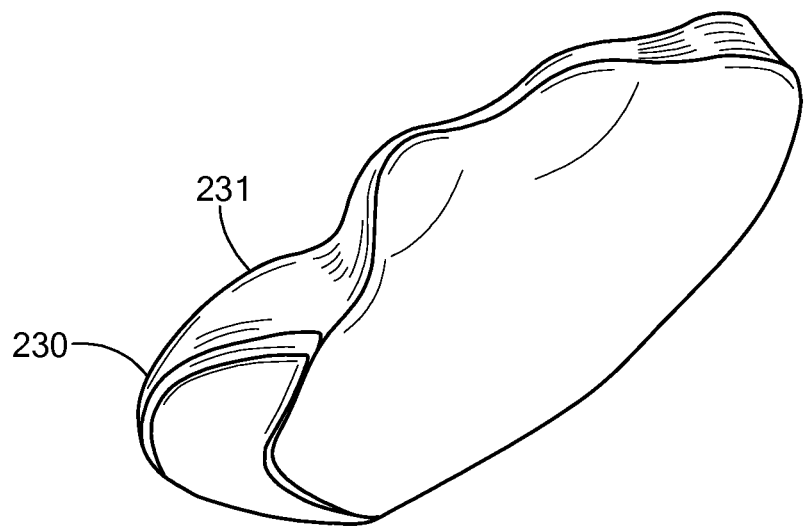

In an alternate embodiment shown in FIG. 2M, it may be desirable to provide one or more cross-members 220 on the lower surface 204 in order to provide a bit of translation movement of the implant relative to the surface of the femur or applicable articular surface, or femur implant. In that event, the cross-member can be formed integral to the surface of the implant or can be one or more separate pieces that fit within a groove 222 on the lower surface 204 of the implant 200. The groove can form a single channel as shown in FIG. 2N1, or can have more than one channel as shown in FIG. 2O1. In either event, the cross-bar then fits within the channel as shown in FIGS. 2N2-O2. The cross-bar members 220 can form a solid or hollow tube or pipe structure as shown in FIG. 2P. Where two, or more, tubes 220 communicate to provide translation, a groove 221 can be provided along the surface of one or both cross-members to interlock the tubes into a cross-bar member further stabilizing the motion of the cross-bar relative to the implant 200. As will be appreciated by those of skill in the art, the cross-bar member 220 can be formed integrally with the implant without departing from the scope of the invention.

As shown in FIGS. 2Q-R, it is anticipated that the surface of the tibial plateau will be prepared by forming channels thereon to receive the cross-bar members. Thus facilitating the ability of the implant to seat securely within the joint while still providing movement about an axis when the knee joint is in motion.

FIG. 2S(1-9) illustrate an alternate embodiment of implant 200. As illustrated in FIG. 2S the edges are beveled to relax a sharp corner. FIG. 2S(1) illustrates an implant having a single fillet or bevel 230. As shown in FIG. 2S(2) two fillets 230, 231 are provided and used for the posterior chamfer. In FIG. 2S(3) a third fillet 234 is provided to create two cut surfaces for the posterior chamfer. The chamfer can assist with insertion of the implant: as the implant is advanced into the joint, the chamfer will assist with distracting the joint until the implant is successfully seated in situ.

Turning now to FIG. 2S(4), a tangent of the implant is deselected, leaving three posterior curves. FIG. 2S(5) shows the result of tangent propagation. FIG. 2S(6) illustrates the effect on the design when the bottom curve is selected without tangent propagation. The result of tangent propagation and selection is shown in FIG. 2S(7). As can be seen in FIG. 2S(8-9), the resulting corner has a softer edge but sacrifices less than 0.5 mm of joint space. As will be appreciated by those of skill in the art, additional cutting planes can be added without departing from the scope of the invention.

FIGS. 2T(1-8) illustrate an alternate embodiment of an implant 200 wherein the surface of the tibial plateau 250 is altered to accommodate the implant. As illustrated in FIG. 2T(1-2), the tibial plateau can be altered for only half of the joint surface 251 or for the full surface 252. As illustrate in FIG. 2T(3-4) the posterior-anterior surface can be flat 260 or graded 262. Grading can be either positive or negative relative to the anterior surface. Grading can also be used with respect to the implants of FIG. 2T where the grading either lies within a plane or a body or is angled relative to a plane of the body. Additionally, attachment mechanisms can be provided to anchor the implant to the altered surface. As shown in FIG. 2T(5-7) keels 264 can be provided. The keels 264 can either sit within a plane, e.g. sagittal or coronal plane, or not sit within a plane (as shown in FIG. 2T(7)). FIG. 2T(8) illustrates an implant which covers the entire tibial plateau. The upper surface of these implants are designed to conform to the projected shape of the joint as determined under the steps described with respect to FIG. 1, while the lower surface is designed to be flat, or substantially flat to correspond to the modified surface of the joint.

Embodiments of the current invention provide for multiple devices including implants for treating facet joints, uncovertebral joints and costovertebral joints and methods enabling or facilitating this treatment.

An implant can be any device or repair system for treating a facet joint, uncovertebral joint and costovertebral or any other joint.

Distraction Device

In another embodiment of the invention, a distraction device can be used to facilitate insertion of an implant into a facet joint. A distraction device can be particularly useful for placement of a balloon or an interpositional implant into the facet joint.

Figure 8A:
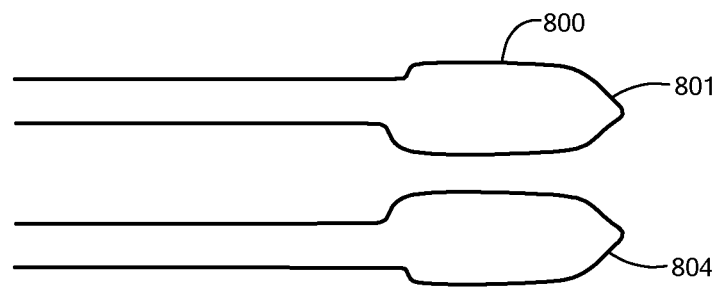
FIGS. 8A-C are examples of various embodiments of a distraction device for preparing a joint for implant insertion.
Figure 8B:
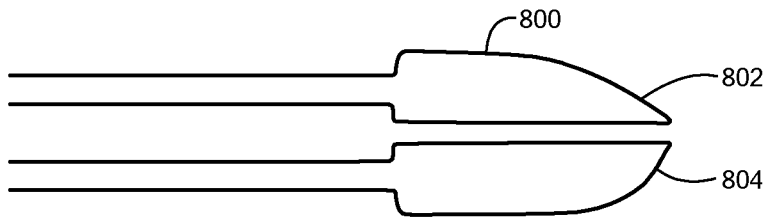
Figure 8C:
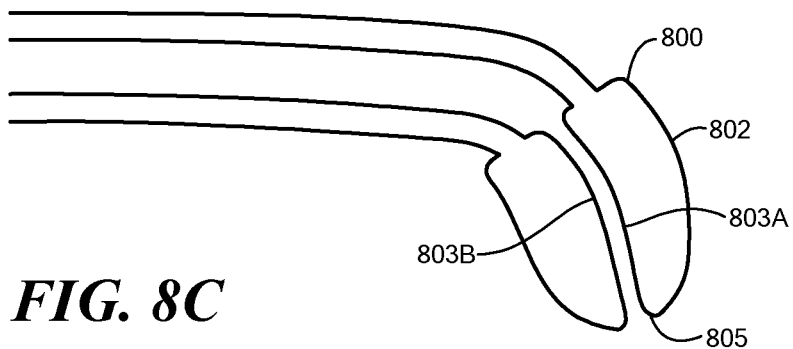

In FIGS. 8A-C, for example, the distraction device can include two or more prongs 800. One or more prongs can be straight 801 (FIG. 8A) or curved 802 (FIG. 8B) in one or more dimensions (FIG. 8C). It can be concave 803A with a mating concave surface 803B. The curvature can be adapted for a facet joint. It can be tapered in the front 804. It can also be round at the tip 805. Preferably, the curvature will be similar to or substantially match that of a facet joint. One or more prongs can be straight or curved, or partially straight and partially curved. Concave and convex shapes are possible can be present at the same time. Irregular shapes can be used.

Figure 9A:
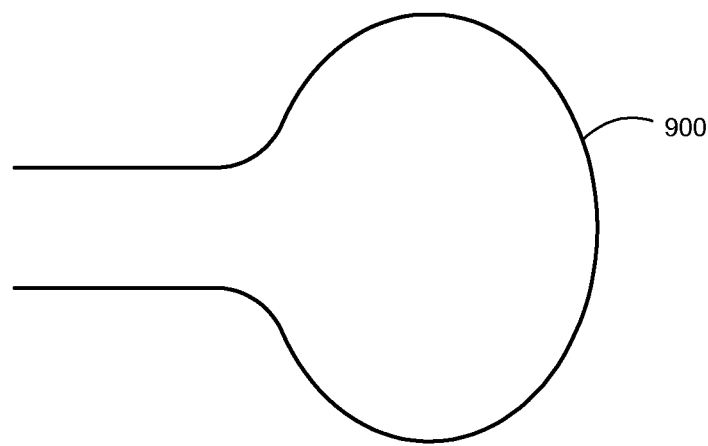
FIGS. 9A-D show various embodiments for distracting the joint and facilitating implant insertion.
Figure 9B:
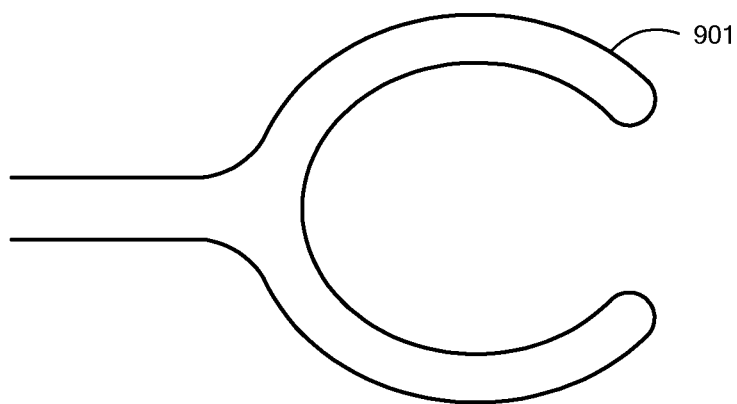
Figure 9C:
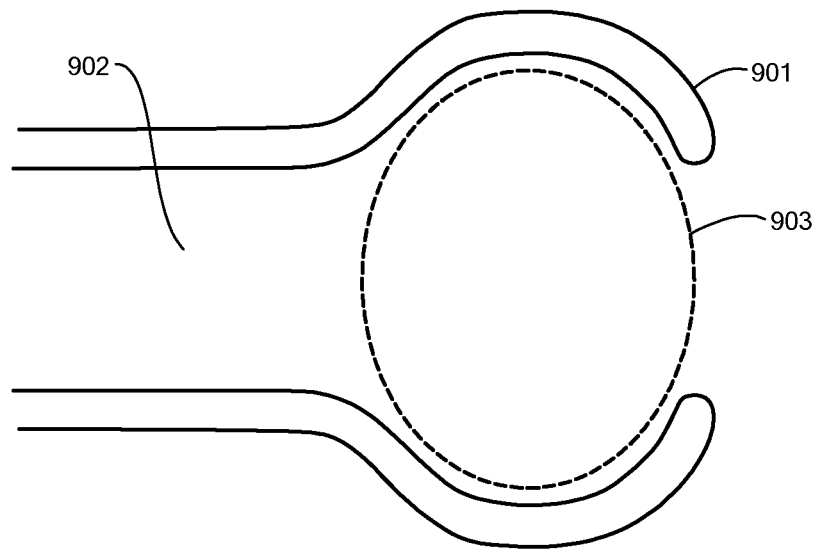
Figure 9D:
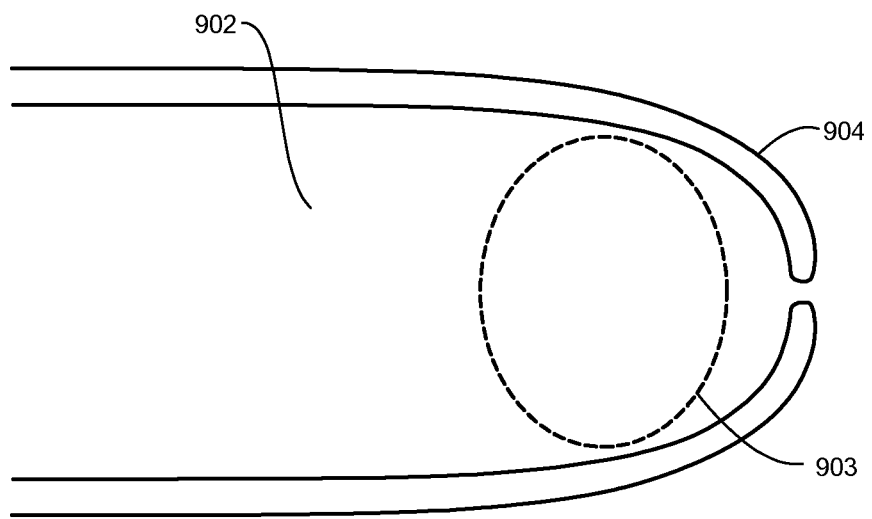

The distraction device can include two plates at the distal tip. In FIG. 9A, the plates can be substantially solid 900. The plates can also be open on one or more sides 901 (FIG. 9B). The distraction device can have an opening 902 that allows for insertion or placement of an implant 903 after distraction of the joint (FIG. 9C). Various shapes of the distraction device 904 are possible (FIG. 9D). The distance between the plates can be substantially zero at the outset. This facilitates insertion into the joint. Once inserted, the distance between the plates can be increased, for example, using a telescoping or jack or ratchet like mechanism. The distracting mechanism can be located within the joint, preferably between the two plates, or external to the joint, for example near the grip of the device. The two plates can be flat or curved, or partially flat and partially curved. Preferably, the curvature will be similar to or substantially match that of a facet joint. Concave and convex shapes are possible can be present at the same time. Irregular shapes can be used.

The area of the distraction device can be slightly smaller than a facet joint, the same as the facet joint or slightly larger than a facet joint.

The distraction device can be hollow in the center or, alternatively, create a hollow, open space to accept a balloon or an implant.

The distraction device can have an opening in the rear at the side pointing dorsally or externally to allow insertion of the balloon or implant while the distraction device is inside the joint.

The distal portion of the distraction device can be wider, typically between two prongs, than the widest width of the implant in the same dimension, typically supero-inferior, to facilitate removal of the distraction device with the implant remaining in situ.

Instrument to Remove or Reduce Bone Growth

Degenerated facet joints, uncovertebral joints or costovertebral joints can demonstrate new bone formation, bone remodeling, hypertrophy, bony overgrowth and/or bone spurs. Facet joints, uncovertebral joints or costovertebral joints can enlarge due to new bone formation, bone remodeling, hypertrophy, bony overgrowth and/or bone spurs formation and spur formation. These conditions will be summarized in the term bone growth in the following.

Figures 2, 2S, 3:
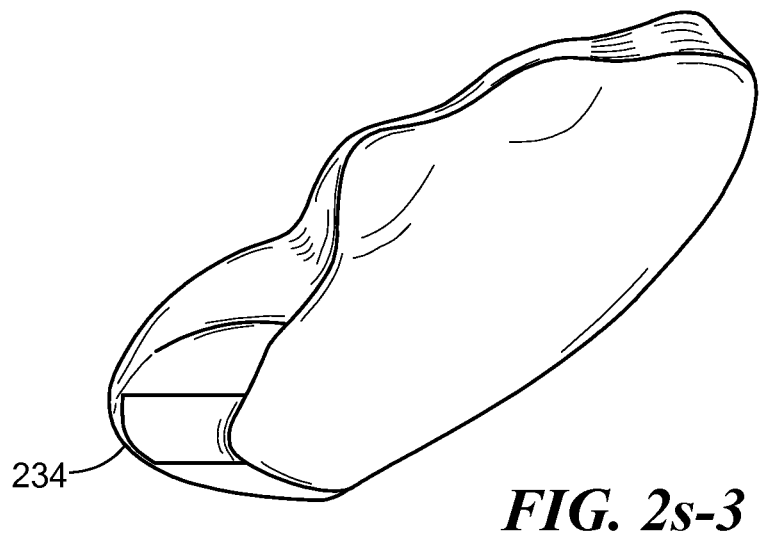

FIGS. 3A and B demonstrate a vertebral body 300, a thecal sac 301, which is deformed on the right side by a bone spur 308, which arises from a facet joint 303. The facet joint on the right side 303 is degenerated, while the facet joint on the left side 302 is relatively normal in shape still. A spinous process is seen posteriorly 304. The degenerated facet joint 303 demonstrates multiple peripheral bone spurs 306 which can lead to an enlargement of the joint. There are also irregularities of the articular surface with some deep marks or tracks 305 and ridges or spurs on the articular surface 307.

Bone growth can cause difficulties during insertion of an implant or balloon. Moreover, bone growth can cause spinal stenosis, including foraminal stenosis, lateral recess stenosis and central stenosis. Thus, while an implant or balloon device designed to alleviate pain originating from the affected joint, i.e., a facet joint, uncovertebral joint or costovertebral joint, the patient may still suffer from back pain and even sciatica after the procedure. The surgeon can optionally consider reshaping the joint and/or removing one or more bone growths.

Figures 2, 2S, 3, 4:
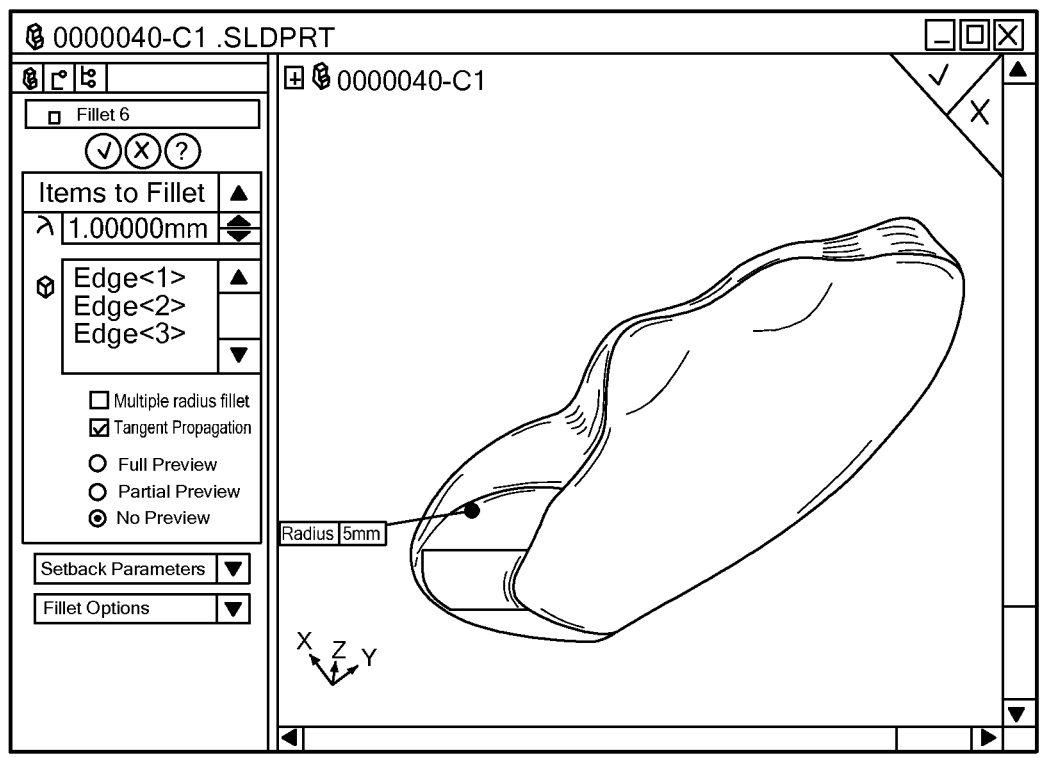
FIG. 4 is an example of a surgical instrument for removal of bone overgrowth and spurs.
Figures 2, 2S, 3, 4, 5:
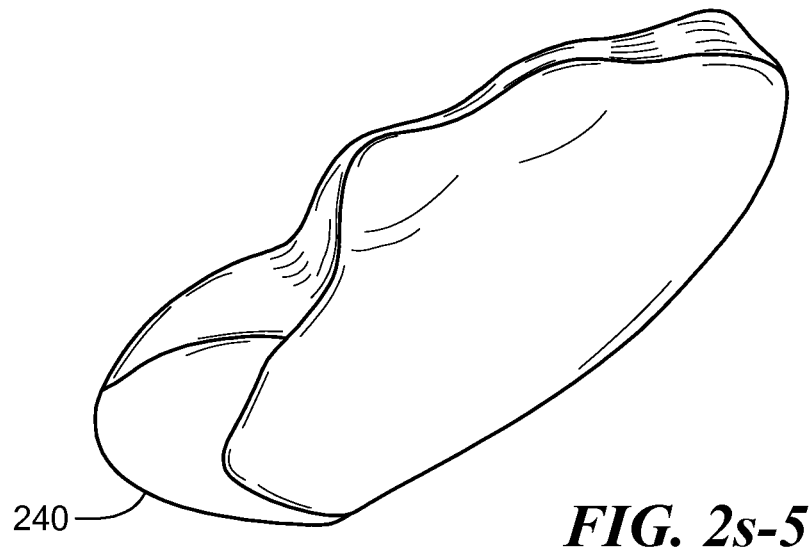
Figures 2, 2S, 3, 4, 5, 6:
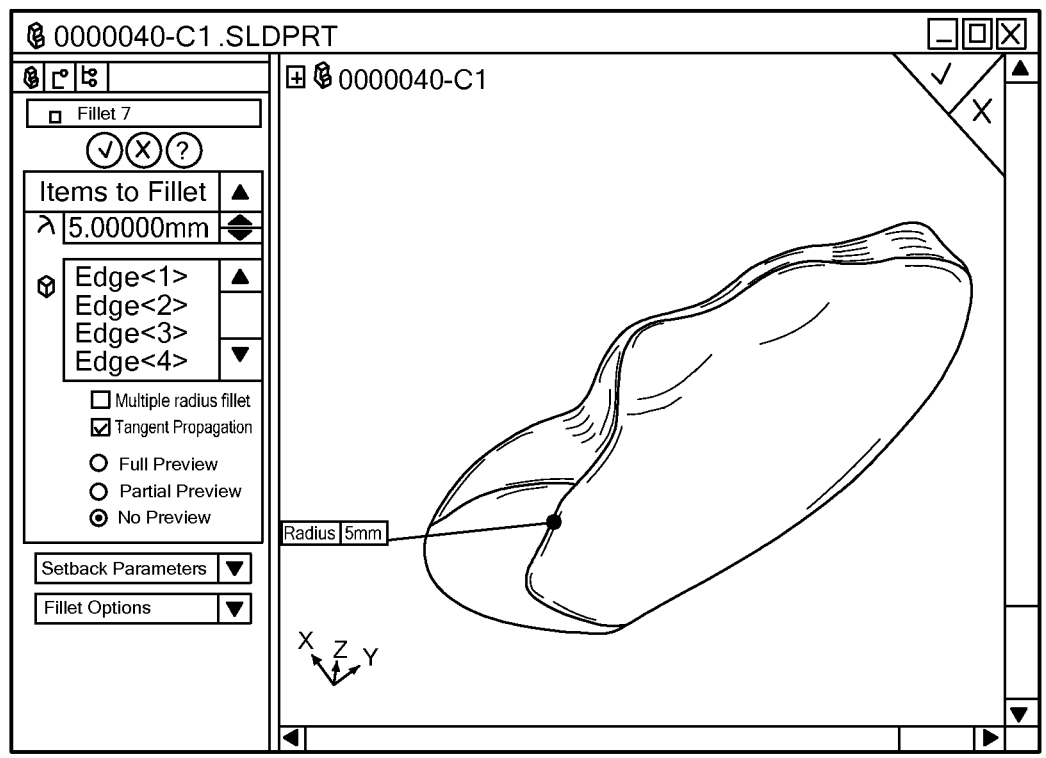

In one embodiment, an instrument (see 400 in FIG. 4) is used for the reshaping of the joint or the removal of one or more bone growths.

The instrument can, for example, have a ring shape at the tip 401. The external aspect of the ring can be blunt 401 in order to minimize potential damage to the thecal sac or the nerve roots. The internal portion 402 of the ring can be sharp. All or part of the external portion can be blunt. All or part of the internal portion can be sharp.

The opening of the ring can then be placed over the bone growth and the instrument can be pulled back, thereby removing all or part of the bone growth.

Figure 5A:
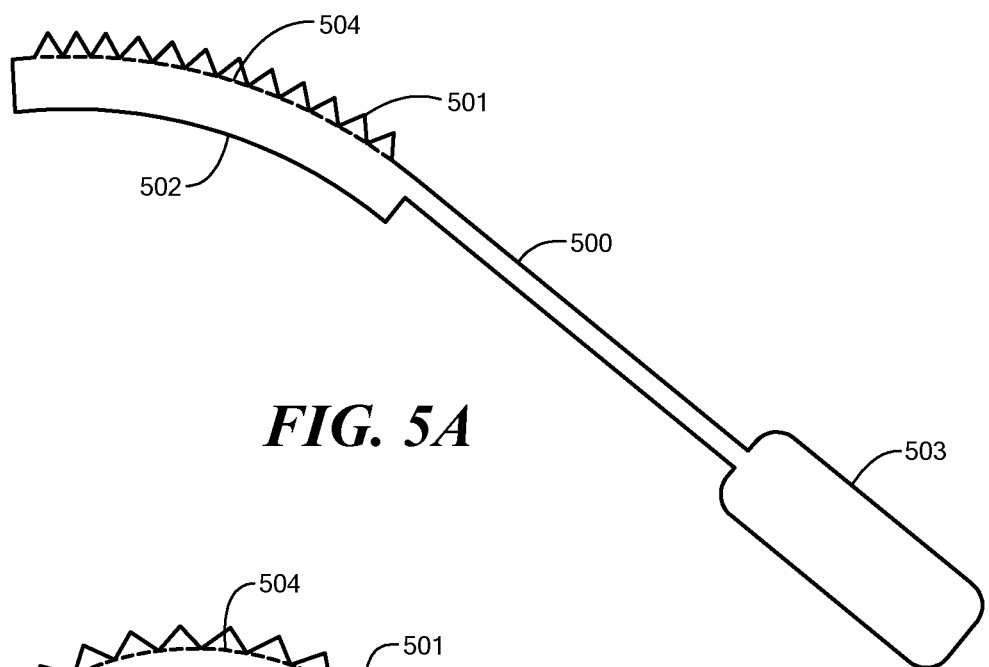
FIGS. 5A-C are examples of various embodiments of a surgical instrument for shaping and smoothing the articular surface.
Figure 5B:
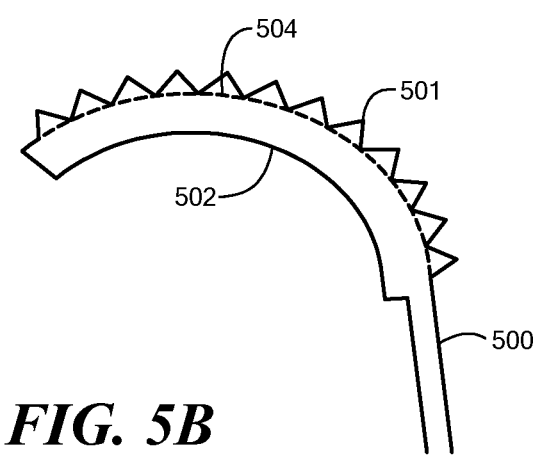
Figure 5C:
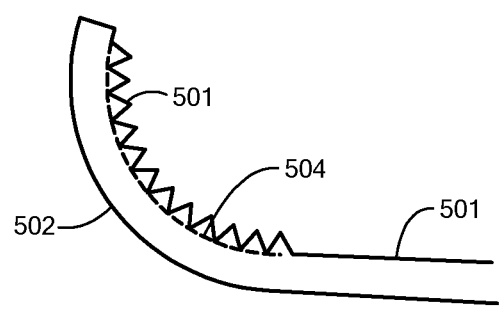

The instrument can include a rough surface creating a rasp-like instrument. In FIGS. 5A-C, various embodiments of an instrument 500 with a rough, rasp-like surface 501 are seen. The portion of the implant that inserted into the joint 502 can have different shapes, e.g., convex or concave in one or more planes (FIGS. 5A-5C). The instrument can have an optional handle 503. The rough surface 501 can be moved over one or two of the articular surfaces of the joint to remove any surface irregularities and to create a new, smooth bearing surface on at least one or, optionally both sides of the joint. The underlying curvature 504 of the rough surface will determine the shape of the articular surface after smoothing it.

Figure 7:
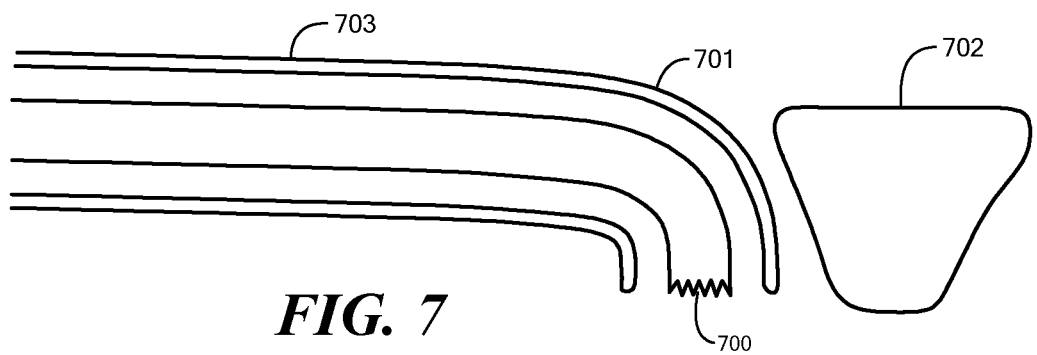
FIG. 7 is an example of an instrument with a shaver 700.

Any mechanical device or electrical mechanism capable of removing bone can be utilized in combination with one or more of the embodiments above and below. For example, in FIG. 7, an instrument with a rotating mill or an oscillating saw or a shaver 700 can be utilized. This instrument can be curved at the tip 701, thereby protecting the thecal sac 702. The instrument can be in a protective cover 703. The instrument is typically inserted via a hole in the ligamentum flavum, although it can also be inserted through the joint or both.

The distal portion of the instrument can be tapered, preferably with a rounded tip. The tapered design can facilitate insertion into the joint if the instrument has to be passed through the joint. The rounded or blunt tip can help avoid injury to a nerve root or the thecal sac.

The instrument can be curved in one or more dimensions. One or more convex portions can be included. One or more concave portions can be included. Convex and concave portions can be present in the same device.

Figure 6A:
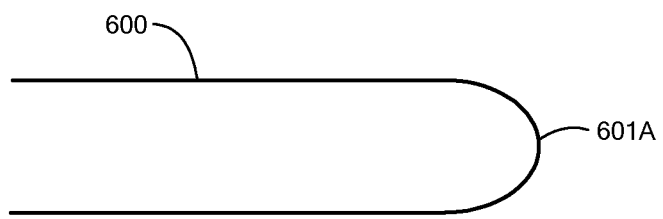
FIGS. 6A-D are examples of various embodiments of an instrument for shaping a facet or other joint and for inserting an implant. The instrument may have a round 601A or tapered tip 601B.
Figure 6B:
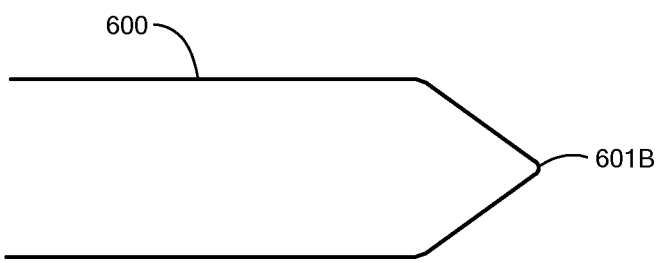
Figure 6C:
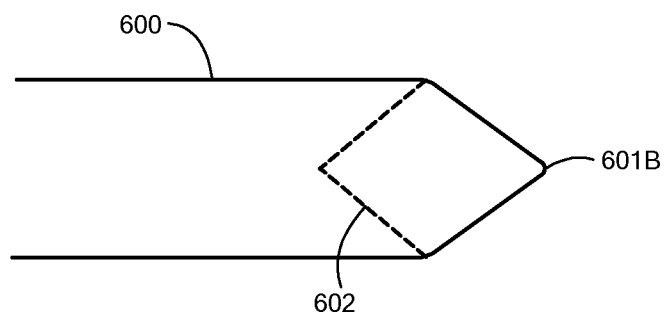
Figure 6D:
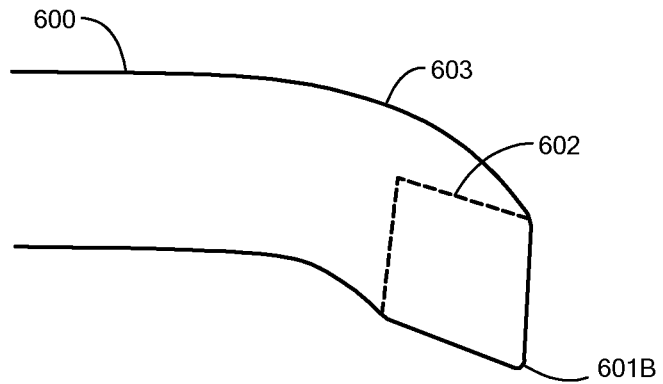

In FIGS. 6A-D, an instrument 600 is seen that has a tapered front portion 601. The tapered front portion can be rounded 601A (FIG. 6A), or triangular 601B (FIG. 6B). While the front of the instrument can be tapered, its side portion can optionally have a sharp recess 602 (FIGS. 6C and D). The sharp recess can assist in removing some bone overgrowth on or adjacent to the articular surface. The instrument can also be curved 603 near or at its tip 601 (FIG. 6D).

In a preferred embodiment, the instrument shape mirrors the shape of the articular surface.

The instrument can be available in various sizes, thicknesses, lengths and shapes.

In another embodiment, the instrument can have a tip that can be bent backward in an angle equal to or greater than 90 degrees. In this setting, the implant is passed past the bone growth. The tip is then brought in contact with the bone growth and the bone growth is removed.

The instrument can include one or more tubes for suction. Optionally, suction can be performed, also using standard suction devices.

The instrument to remove or reduce bone growth can be used in conjunction with the distraction device. Optionally, both can be integrated.

Oversized Implant or Repair Device

Degenerated facet joints, uncovertebral joints or costovertebral joints can demonstrate new bone formation, bone remodeling, hypertrophy, bony overgrowth and/or bone spurs. Facet joints, uncovertebral joints or costovertebral joints can enlarge due to new bone formation, bone remodeling, hypertrophy, bony overgrowth and/or bone spurs formation and spur formation. These conditions will be summarized in the term bone growth in the following. Bone growth can lead to an enlargement of the load bearing surface beyond the dimensions of the articular surface, i.e., portion of the joint that is covered by cartilage prior to the onset of the degenerative and arthritic changes.

Thus, an implant or a repair device including an injectable material sized only to the articular surface, i.e., portion of the joint that is covered by cartilage prior to the onset of the degenerative and arthritic changes, would not cover all of the load bearing surface.

In one embodiment, an implant or a repair device including a balloon or an injectable material can be oversized to account for the enlargement of the joint and the greater dimension of the load bearing surface in patients with degenerative or arthritic changes of the facet joints, uncovertebral joints or costovertebral joints. The dimensions of the implant or a repair device including a balloon or an injectable material can be increased in one or more dimensions. In addition, the shape of the implant can be adjusted to account for the bone growth and for irregularities in joint shape as a result of the bone growth.

In another embodiment, the implant size can be selected or adjusted to account for a reduction in size of the joint after removal of a bone growth or to account for a reduction in size of the joint after partial resection of the joint or the articular process.

These adjustments can be made intraoperatively, for example using measuring or sizing devices (see below). Alternatively, these adjustments can be made using imaging software. For example, using CT or MRI data the severity of a spinal stenosis can be estimated. In a second step, resection of a bone growth or partial resection of a joint or articular process can be simulated and it can be determined what the optimal implant size or shape is following these adjustments.

Implant Manufacturing

The implant can be patient specific with each implant custom manufactured, for example using CAD/CAM and rapid prototyping and/or casting techniques. Alternatively, the implant can be selected from a pre-existing library or assortment of implants. The library of implants will typically cover a range of sizes and shapes applicable to most patients and also allowing for oversizing consistent with the embodiment above.

Pre-Existing Repair Systems

As described herein, repair systems of various sizes, curvatures and thicknesses can be obtained. These repair systems can be catalogued and stored to create a library of systems from which an appropriate system for an individual patient can then be selected. In other words, a defect, or an articular surface, is assessed in a particular subject and a pre-existing repair system having a suitable shape and size is selected from the library for further manipulation (e.g., shaping) and implantation.

Image Guidance

In various embodiments, imaging techniques can be used for delivering a device. The imaging techniques can include the use of x-rays, CT scans, fluoroscopy, C-arms, CT fluoroscopy, C-arms with CT like cross-sectional reconstruction and MRI. In addition to that, surgical navigation systems, for example using radiofrequency or optical object location and reference means, can be used.

Sizing Tool

In another embodiment of the invention, a sizing tool is used to determine the optimal shape of the implant. The sizing tool can be applied at a first procedure, for example using percutaneous need guidance. Preferably, the sizing tool is used at the time of the procedure for insertion of the therapeutic device into the facet joint, uncovertebral joint or costovertebral joint.

The sizing tool can include various tools for measuring implant dimensions. For example, a ruler or a caliper can be part of the sizing tool. The sizing tool can be used to measure and estimate preferred dimensions of the device, e.g., in superoinferior or mediolateral dimension. It can be used to estimate implant thickness, in one or more locations. The sizing tool can also be used to measure implant curvature.

In one embodiment, the sizing tool can be partially or completely deformable. The sizing tool is inserted into the joint, thereby taking the natural shape of the joint. The sizing tool is then withdrawn from the joint. The resultant shape of the sizing tool is then compared against a library or assortment of premanufactured implants and the best fitting implant with the best match relative to the sizing tool is selected.

In another embodiment, the sizing tool can include a gauge to measure implant dimensions in antero-posterior or superoinferior or medio-lateral direction or combinations thereof. This gauge can, for example, be a ruler integrated into the sizing tool. The sizing tool is inserted into the joint. The area where the dorsal portion of the articular surface aligns with the first visible tick mark on the ruler indicates typically the preferred implant length.

The sizing tool can also include a gauge in superoinferior or any other dimension.

One or more sizing tools can be used. The sizing tool can include one or more dimensions of one or more of the premanufactured implants in the implant library or assortment.

The sizing tool can be available in various shapes. For example, a T or t-shape can provide dimensions in two or more directions. The thickness of the sizing tool can be used to estimate the preferred thickness of the implant.

Sizing tools can be made with various different curvatures and radii, typically resembling the radii of the implant. By inserting sizing tools of different radii, the optimal radius for the implant can be determined.

Alternatively, the implant shape and its radii can be determined using an imaging test.

Alternatively, a trial implant can be used. Trial implants can substantially match the size and shape of the implants in the pre-manufactured library of implants or assortment of implants.

The sizing tool can be malleable and/or deformable.

Preparing the Joint

In some circumstances, it may be desirable to alter the articular surface. For example, the surgeon may elect to flatten the articular surface, to shape it, to increase its curvature or to roughen the articular surface or to remove the cartilage.

The shaping can be advantageous for improving the fit between the implant and the articular surface. Roughening of the articular surface can improve the conformance of the implant to the articular surface and can help reduce the risk of implant dislocation.

Facet joints are frequently rather deformed as a result of progressive degenerative changes with deep marks and tracks distorting the articular surface. When an interpositional implant is used, the marks and tracks can be used for stabilizing the implant on one side. The implant is then typically made to mate with the marks and tracks on one side of the joint thereby achieving a highly conforming surface, and, effectively, a significant constraint to assist with reducing possible implant motion on this side of the joint. The opposing articular surface, however, needs to be minimally constraining in order to enable movement between the implant surface and the opposing articular surface. Thus, the opposing surface can therefore be treated and shaped to remove any marks and tracks and to re-establish a smooth gliding surface. Preferably, the opposing surface will be made to match the smooth surface of the implant on this side.

An instrument for preparing the articular surface can be slightly smaller than a facet, uncovertebral or costovertebral joint, similarly sized or larger in size than the respective joint.

The instrument can be curved or flat. The implant can be curved in more than one dimension.

The instrument can be a rasp or mill-like device. It can be mechanical or electrical in nature.

Improving Implant Stability

In most embodiments, the device shape and size is substantially matched to one or more articular surface. The implant can fill the space between two opposing articular surfaces partially or completely.

The implant can have extenders outside the articular surface for stabilizing implant position and for minimizing the risk of implant dislocation. Such an extender can be intra- or extra-articular in location. If it is extra-articular, it will typically extend outside the joint capsule.

In one embodiment, the extender can be plate or disc or umbrella shaped, covering at least a portion of the bone outside the articular surface. The extender can be only partially plate or disc or umbrella shaped. The plate or disc or umbrella shaped extender will typically be oriented at an angle to the intra-articular portion of the implant, whereby said angle is substantially different from 180 degrees, more preferred less than 150 degrees, more preferred less than 120 degrees, more preferred less than 100 degrees. In some embodiments, the angle may be equal or less than 90 degrees.

The extender can have a constant or variable radii in one or more dimensions. The extender can be adapted to the patient's anatomy.

If a balloon is used and a self-hardening substance is injected into the balloon, the balloon can have a second, separate portion or a second balloon can be attached, whereby the resultant cavity that will be filled with the self-hardening material can be located outside the articular surface area and can be even external to the joint capsule. Once the self-hardening material is injected, the material has hardened and the balloon has been removed, a lip or ridge or extender can be created in this manner that can help stabilize the resultant repair device against the adjacent bone or soft-tissues.

Protecting Neural and Other Structures

In another embodiment of the invention, the device or implant can be shaped to protect the neural structures. For example, the ventral portion of the implant can be rounded to avoid any damage to the neural structures in the event the implant moves or subluxes or dislocates anteriorly.

The dorsal and superior and inferior margins can also be rounded in order to avoid damage to neural structures in the event of a subluxation or dislocation into the epidural space. Moreover, a round margin can help minimize chronic wear due to pressure onto the joint capsule.

The margin of the implant can be round along the entire implant perimeter or along a portion of the perimeter.

The implant sidewall can be straight or alternatively, it can be slanted with an angle other than 90 degrees. The implant thickness can vary along the perimeter.

The thickness of the implant can be thinner at the margin than in the center, along the entire implant margin or in portions of the implant margin. The thickness of the implant can be thicker at the margin than in the center, along the entire implant margin or in portions of the implant margin.

Implant Shape for Easy Insertion

Figure 10A:
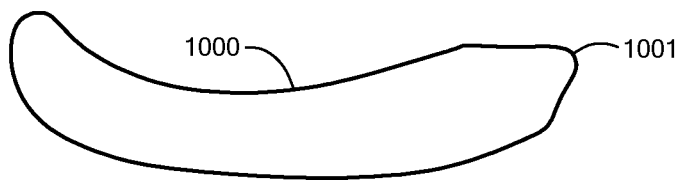
FIGS. 10A-F show various embodiments describing various types of implant margin, including tapered designs 1001 and round designs 1002.
Figure 10B:

The implant shape can be adapted to facilitate insertion into the joint. For example, in FIG. 10A, the portion of the implant 1000 that will face forward, first entering the joint, can be tapered 1001 relative to portions or all of the implant, thereby facilitating insertion. The tapered tip can be pointed 1001 or round 1002 (FIG. 10B). In most embodiments, a round tip is preferably since it can help reduce the risk of damage to adjacent structures.

Figure 10C:
Figure 10D:
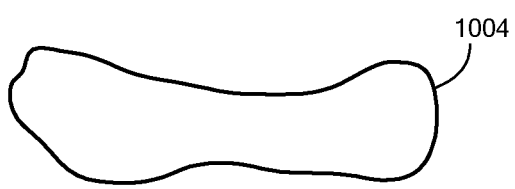
Figure 10E:
Figure 10F:

The implant can have a sharp edge 1003 (FIG. 10C) or a rounded edge 1004 (FIG. 10D). A rounded edge is typically preferred. The implant can have a substantially straight margin 1005 (FIG. 10E) or a substantially tapered margin 1006 (FIG. 10F).

The arthroplasty can have two or more components, one essentially mating with the tibial surface and the other substantially articulating with the femoral component. The two components can have a flat opposing surface. Alternatively, the opposing surface can be curved. The curvature can be a reflection of the tibial shape, the femoral shape including during joint motion, and the meniscal shape and combinations thereof.

Examples of single-component systems include, but are not limited to, a plastic, a polymer, a metal, a metal alloy, crystal free metals, a biologic material or combinations thereof. In certain embodiments, the surface of the repair system facing the underlying bone can be smooth. In other embodiments, the surface of the repair system facing the underlying bone can be porous or porous-coated. In another aspect, the surface of the repair system facing the underlying bone is designed with one or more grooves, for example to facilitate the in-growth of the surrounding tissue. The external surface of the device can have a step-like design, which can be advantageous for altering biomechanical stresses. Optionally, flanges can also be added at one or more positions on the device (e.g., to prevent the repair system from rotating, to control toggle and/or prevent settling into the marrow cavity). The flanges can be part of a conical or a cylindrical design. A portion or all of the repair system facing the underlying bone can also be flat which can help to control depth of the implant and to prevent toggle.

Non-limiting examples of multiple-component systems include combinations of metal, plastic, metal alloys, crystal free metals, and one or more biological materials. One or more components of the articular surface repair system can be composed of a biologic material (e.g., a tissue scaffold with cells such as cartilage cells or stem cells alone or seeded within a substrate such as a bioresorable material or a tissue scaffold, allograft, autograft or combinations thereof) and/or a non-biological material (e.g., polyethylene or a chromium alloy such as chromium cobalt).

Thus, the repair system can include one or more areas of a single material or a combination of materials, for example, the articular surface repair system can have a first and a second component. The first component is typically designed to have size, thickness and curvature similar to that of the cartilage tissue lost while the second component is typically designed to have a curvature similar to the subchondral bone. In addition, the first component can have biomechanical properties similar to articular cartilage, including but not limited to similar elasticity and resistance to axial loading or shear forces. The first and the second component can consist of two different metals or metal alloys. One or more components of the system (e.g., the second portion) can be composed of a biologic material including, but not limited to bone, or a non-biologic material including, but not limited to hydroxyapatite, tantalum, a chromium alloy, chromium cobalt or other metal alloys.

One or more regions of the articular surface repair system (e.g., the outer margin of the first portion and/or the second portion) can be bioresorbable, for example to allow the interface between the articular surface repair system and the patient's normal cartilage, over time, to be filled in with hyaline or fibrocartilage. Similarly, one or more regions (e.g., the outer margin of the first portion of the articular surface repair system and/or the second portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

The repair system (e.g., the second component in multiple component systems) can be attached to the patient's bone with use of a cement-like material such as methylmethacrylate, injectable hydroxy- or calcium-apatite materials and the like.

In certain embodiments, one or more portions of the articular surface repair system can be pliable or liquid or deformable at the time of implantation and can harden later. Hardening can occur, for example, within 1 second to 2 hours (or any time period therebetween), preferably with in 1 second to 30 minutes (or any time period therebetween), more preferably between 1 second and 10 minutes (or any time period therebetween).

FIG. 11 shows an implant device 1100 for implantation into a facet joint in accordance with one embodiment of the invention. As shown, the facet joint includes opposing articular surfaces 1107 and 1108. In the present embodiment, device 1100 is an interpositional device that is configured to be inserted between opposing articular surfaces 1107 and 1108. In various embodiments, one side 1103 of the device 1100 forms an articular surface in the present embodiment that is substantially smooth and that is configured to oppose facet joint surface 1107 when implanted. Articular surface 1103 can include convex and concave shapes and combinations thereof. Surface 1103 need not be smooth, but, preferably, the surface is configured to provide a suitable bearing surface on which the articular surface 1103 can glide, thereby moving relative to the surface of the opposing articular surface 1107. Preferably, this reduces friction between the opposing surfaces of the joint and the device and thereby reduces wear both on the device and the joint surface as well as facilitates improved articulation of the joint surface with the device.

The opposite side 1105 of device 1100 also forms an articular surface. However, the surface 1105 substantially conforms to the corresponding joint surface 1108. This allows surface 1105 to resist motion relative to the opposing surface 1108, The surface 1105 incorporates the general shape of the joint as a negative such that the surface 1105 and joint surface 1108 couple together. By making one side of the device 1100 conform with at least one articular side, the device 1100 can advantageously be stabilized against said articular surface.

Other embodiments are possible to stabilize the device. For example, the surface 1105 may also optionally account for irregularities caused by the arthritis. Such an irregularity may include, without limitation, ridges, crescents, spurs, osteophytes, cysts and the like. In other embodiments, the surface may not be specific to the joint, but may instead include predefined patterns of ridges, points, cones, and/or other shapes or contours, either alone or in combination, to provide a surface that resists motion. In still other embodiments, patient specific features can be included with standardized feature. For example, without limitation, the articular surface of the device can generally match the opposing articular surface of the joint to include general contours of the joint without providing a specific match or mating to the articular surface, and the standardized contours can be included on the surface such that the surface has a close but not perfect fit sufficient to engage the standardized resistive surface against the opposing articular surface. In another embodiment, the device can have a portion of the articular surface that is conforming and a portion that is not. Either or both portions can also optionally include non-patient specific elements that further assist in providing stability to the device. In still other embodiments, the device can include an anchoring device such as a pin or fin that can be engaged with a portion of the facet joint.

Either side 1103 or 1105 can include various combinations of one or more convexities and/or concavities, for example, to provide a conforming surface or generally conforming surface. Embodiments of the device may have a first shape, and a second side of the implant can, optionally be, at least in part, a mirror image of said first side or said first shape.

The device 1100 may be sized to incorporate marginal and other osteophytes. The device may also be sized and shaped to exclude such osteophytes. The latter approach is typically preferred when these osteophytes or spurs are removed intraoperatively. On one side the device can include osteophytes or bone spurs. On another side, the device can be shaped to exclude osteophytes.

In operation, the articular surface 1107 is able to move smoothly relative to surface 1103 of the device 1100. The shape of the smooth surface 1100 as well as the opposite surface may be obtained with use of an imaging test. The imaging test may be, without limitation, a CT or MRI, a digital tomosynthesis or methods using injection of imaging contrast media, intra-articular or intravenous, ultrasound, or any other imaging modality known in the art. The bony or cartilaginous landmarks may be measured on the scan. The image may be manipulated to remove overhanging osteophytes or other articular abnormalities virtually. A smoothing function may be applied to the measured or derived articular surface, for example by obtaining an image, e.g., a CT or MRI images, deriving the articular surface shape, e.g. cartilage or bone, and then applying a smoothing function. Alternatively, the best fitting pre-manufactured device may be selected from a library of implants. These pre-manufactured implants may already include at least one smooth bearing surface. Alternatively, the dimensions of the joint may be derived from an image, and a virtual model of an implant can be fitted to match that shape by deforming said virtual 3D model.

The device 1100 can be used unilaterally, e.g., in a left or right facet joint, or bilaterally. The device can be used at a single spinal level or multiple spinal levels. The device can be used in a cervical, a thoracic and/or a lumbar spine.

The device 1100 may be designed to be substantially a mirror image of the two articular surfaces or to reflect the shape of at least one articular surface. In various embodiments, the device 1100 may include at least one or more convexity, concavity and/or variation in thickness, diameter and/or general shape. Said at least one or more convexity, concavity and/or variation in thickness, diameter and/or general shape may be designed or selected to change the spatial relationship between the two opposing articular surfaces of the facet joint.

In other embodiments, methods and devices for repairing facet and other joints allow for the customization of implants to suit a particular subject, for example in terms of size, thickness and/or curvature. When the shape (e.g., size, thickness and/or curvature) of the articular cartilage surface is an exact or near anatomic fit with the non-damaged cartilage or with the subject's original cartilage, the success of repair is enhanced. The repair material may be shaped prior to implantation and such shaping can be based, for example, on electronic images that provide information regarding curvature or thickness of any "normal" cartilage surrounding the defect and/or on curvature of the bone underlying the defect. Alternatively, an implant can include various combinations of both patient-specific and non-patient-specific features.

Various methods may be used to manufacture both entirely patient-specific implants as well as implants that include both patient-specific and non-patient specific features. For example, implants can be generated using machining, metal casting, rapid-prototyping, digital printing or other digital manufacturing methods. Alternatively, generic implants or blanks can be manufactured to a particular specification, and one or more patient-specific dimensions or other characteristics can be included by, for example, machining the blank to include the desired dimension or other characteristic or to create and entirely patient specific implant.

Thus, for example, and without limitation, a device could have a standardized smooth articular surface and a customized opposite surface for stabilizing the implant that is machined into the implant during the manufacturing process. Similarly, a blank implant can include standard surfaces and be sized and/or shaped about a perimeter of the device to match the dimensions of the facet joints. Other embodiments may be sized to a specific length or thickness. In still other embodiments, a set of patient-specific implants of varying thicknesses can be provided, for example, in a kit or package, to allow a surgeon to select the desired thickness during surgery to provide appropriate spacing and/or to adequately relieve pressure on the interstitial space adjacent the implant (as discussed below).

Additionally, the implants may be manufactured using a series of two-dimensional (2D) and/or three-dimensional (3D) images. For example, a 3D model of the joint can be created using a set of 2D images built up in slices to provide a 3D image. In addition, to cross-sectional or volumetric imaging technologies including CT, spiral CT, and MRI, stereoscopic imaging modalities may be utilized. Stereoscopic imaging is any technique capable of recording three-dimensional information from two two-dimensional, projectional imaging. Traditional stereoscopic imaging includes creating a 3D visualization or representation starting from a pair of 2D images. The projection path of the 2D images is offset. The offset is, for example, designed to create an impression of object depth for the eyes of the viewer. The offset or minor deviation between the two images is similar to the prospectors that both eyes naturally receive in binocular vision. Using two or more images with an offset or minor deviation in perspective, it is possible to generate a point cloud or 3D surface or 3D visualization of a joint or an articular surface, which can then be input into a manufacturing system such as a rapid prototyping or milling machine. Dual or more light path, as well as single light path, systems also can be employed Software may be used to allow automatic, semi-automatic or manual identification of relevant anatomic points to calculate the anatomic and biomechanical parameters, in accordance with various embodiments of the invention. Optionally, this can be done in 3D rather than only in 2D. Alternatively, the relevant anatomic points can be selected manually and the axes can be calculated.

Identification and preparation of the implant site and insertion of the implant also can be supported by a surgical navigation system. In such a system, the position or orientation of a surgical instrument with respect to the patient's anatomy can be tracked in real-time in one or more 2D or 3D images. These 2D or 3D images can be calculated from images that were acquired preoperatively, such as MR or CT images. Non-image based surgical navigation systems that find axes or anatomical structures, for example with use of joint motion, can also be used. The position and orientation of the surgical instrument as well as the mold including alignment guides, surgical instrument guides, reaming guides, drill guides, saw guides, etc. can be determined from markers attached to these devices. These markers can be located by a detector using, for example, optical, acoustical or electromagnetic signals.

Referring again to FIG. 11, during an implantation procedure, the surgeon may optionally elect intraoperatively to further smoother the articular surface 1107. For example, a rasp or a sharp curette or any other device known in the art may be used to modify the articular surface.

Referring additionally to FIGS. 12-13, various embodiments are shown that include additional features and combinations of features that further stabilize the device and/or provide other benefits. For example, implant 1100 includes an anchor 1106 that serves as an anchor, stopper, cap and/or lip that engages the outer surface(s) of the facet joint to prevent the implant from sliding or otherwise moving through the joint space or dislodging in the direction opposite anchor 1106. In a preferred embodiment, the anchor 1106 may be designed to prevent forward subluxation into the epidural space or into neural foramina, and reduces the chance of or prevents potential nerve root or cord injury.

The anchor 1106 will typically be placed at the posterior facing portion of the device. The anchor 1106 may be intraarticular in location, i.e. contained within the synovial lining of the joint, or may extend external to the joint. The anchor may optionally be attached to the joint capsule, e.g., with a suture or clip. The anchor 1106 may extend beyond a joint margin or an articular surface. The anchor 1106 may be anchored against a bone spur, and/or attached to a fascia.

The anchor 1106 may be symmetrical or asymmetrical in shape. It can include at least one convex and/or one concave portion. The anchor 1106 may be modeled to a particular patient and spinal level, for example using data from a CT scan or MRI scan. All or portions of the anchor 1106 can be pre-shaped or pre-manufactured to the patient's specific anatomy.

Additionally, a device 1200 may have a dumbbell-shaped or drumstick-shaped end 1215 with a thicker portion relative to a middle portion 1216 of device 1200. (Other shapes and configurations are possible.) As shown in FIGS. 12 and 13, in accordance with various embodiments of the invention, the thicker portions 1215 and 1315 may be located, without limitation, anteriorly or posteriorly, inferiorly or superiorly, medially or laterally. For example, thicker portion 1215 may be about 1.5 mm, with the thinner portion 1216 being approximately 1 mm. With this device shape one articular facet, for example the inferior facet of the superior vertebral body, may be moved anteriorly or posteriorly. For example, by moving the inferior facet of the superior vertebral body posteriorly, the spinal canal can be decompressed. Alternatively, by moving the superior facet of the inferior vertebral body anteriorly, the spinal canal may be decompressed. The change in dimensions of the spinal canal can be beneficial for treating stenosis involving at least one of a central canal, a lateral recess, a neural foraminal space or an extraforaminal space.

The device shape may be chosen to alter the spatial relationship of the different components of the facet joints favorably in order to help move individual portions of the facet joints and to reduce spinal stenosis caused or aggravated by facet joint arthritis. This movement of one or more articular surface of the facet joint may take into account bone spurs or osteophytes and help move them further away from the epidural space or nerve roots. Preoperative image simulation can be used to simulate the effect of device insertion. This simulation can be performed by simulating various types of motion, eg flexion, extension, bending, lateral bending or rotation or by simulating various types of loading including axial loading of the spine or facet joints. In this manner, dimensional changes on the spinal canal invoked by device insertion can be assessed for different positions or different conditions. Ultimately, this analysis can assist in identifying a device shape most suitable for a patient, including a device shape that is least likely to sublux or most beneficial for changing spinal canal or foraminal dimensions.

In alternative embodiments, implants of various lengths and or thicknesses can be provided to allow a surgeon to select a device that provides the desired positioning of the bones of the facet joints. In still other embodiments, an adjustable device may be provided.

Various combinations of features are possible. For example, comparing FIGS. 11 and 12, a device 1100 includes a standard end 1115 with an anchor 1106, while device 1200 includes a dumbbell-shaped end 1215 and an anchor 1206. Comparing FIGS. 12 and 13, two devices 1200 and 1300 each include anchors 1206 and 1306 and dumbbell-shaped ends 1215 and 1315 that are thicker relative to middle portions 1216 and 1316 respectively. However, device 1200 includes two smooth articular surfaces 1203 and 1217, while device 1300 includes one smooth articular surface 1303 and a conforming articular surface 1317.

Figure 15:
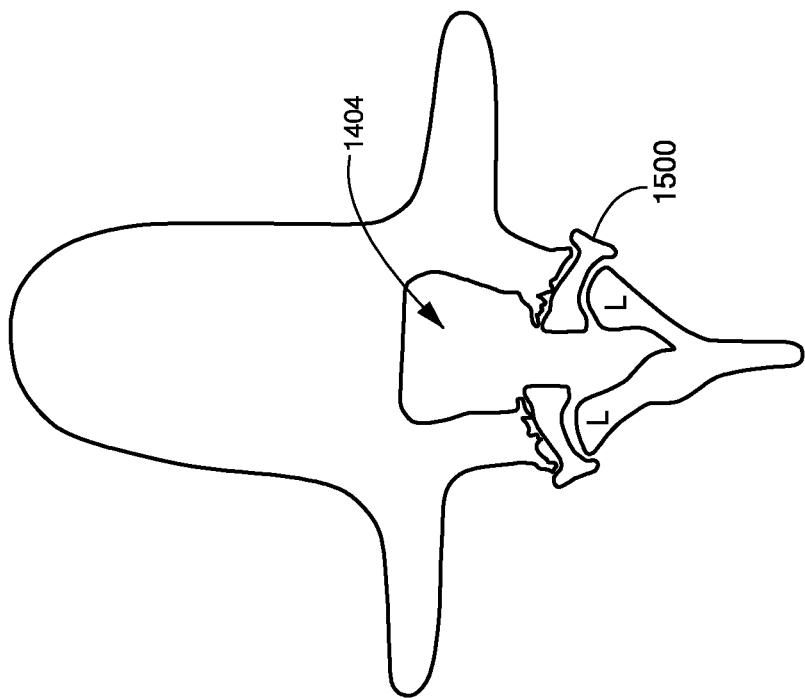
FIG. 15 shows a facet device capable of changing position or orientation of one or two facet joints, optionally by moving bone spurs or bony excrescences, thereby reducing spinal stenosis, in accordance with one embodiment of the invention.
Figure 14:
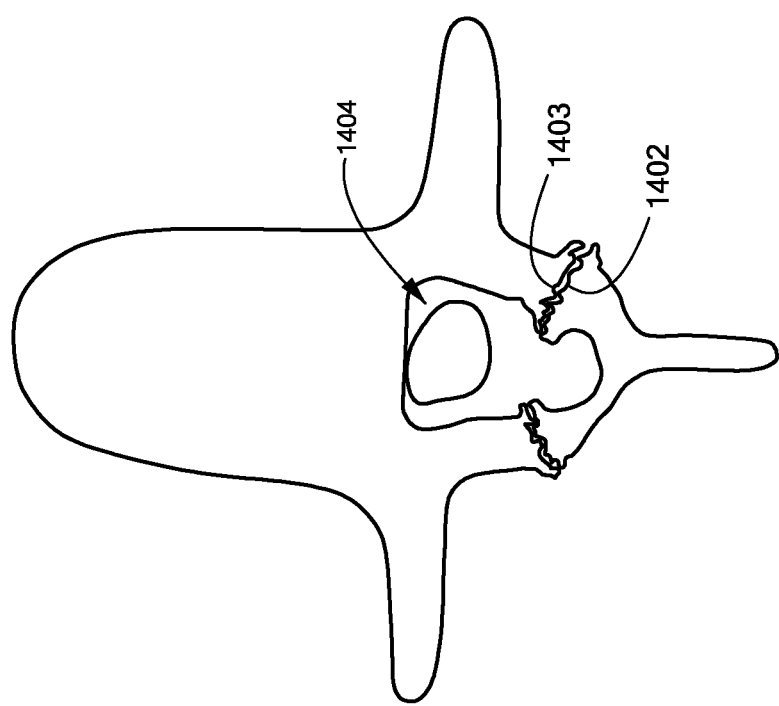
FIG. 14 shows a bone spur on a surface associated with a facet joint.

FIG. 14 shows a bone spur 1402 on a surface associated with a facet joint. FIG. 15 shows a device 1500 that changes the alignment and/or position of a facet joint, changes the dimension of the spinal canal and, optionally, pushes the spur away, in accordance with one embodiment of the invention.

The desired movement may be determined intraoperatively. Alternatively, the desired movement may be simulated preoperatively in a virtual environment by manipulating 2D or 3D images and objects derived from such images.

Optionally, the surgeon may also elect to resect bone spurs arising from a facet joint. Preferably, the surgeon will access such bone spurs through the facet joint without opening the anterior capsule of the facet joint. In this manner, the epidural space remains untouched and the possibility for bleeding and postoperative fibrosis is greatly reduced. Spacers may also be employed in this and other embodiments. Such spacers may optionally be attached to the device and they can help change the spatial position of different components of the facet joints as well.

In one embodiment of the invention, a ratchet or jack-like device can be inserted into the facet joint, optionally with a tapered tip. The ratchet or jack-like device is then used for opening the facet joint for insertion of the device.

In a preferred embodiment, referring again to FIG. 11, the device 1100 may be designed so that it can be inserted without breaching the anterior capsule of the facet joint(s) leaving the epidural space untouched. This approach has the benefit of avoiding or reducing intraoperative or epidural bleeding, thereby potentially reducing the incidence of postoperative scar, fibrosis and arachnoiditis, all dreaded complications of spinal surgery.

If the surgeon desires to remove any bone spurs, or to smooth one or more articular surfaces, or to resect one or more portions of the joint, she may advantageously approach the joint through a posterior approach, entering through the posterior capsule and performing these steps without breaching the anterior joint capsule.

Instruments may be designed for this purpose. The instruments may have sizes and shapes that substantially match the shape of the facet joints. The instruments may optionally be made individually for each patient, for example, by obtaining a preoperative scan and then machining or rapid prototyping the instrument with a shape adapted to the joint(s) of a particular patient. Alternatively, the instruments and/or instrument shape can be selected based on the articular shape determined on the imaging test.

All materials known in the art can be used with the devices described in this invention. For example, the device may be made of a metal, ceramic, and/or polymer. Non-limiting examples of metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Nitinol can be advantageous if the device is inserted through a minimally invasive port including an endoscope. The device can then "unfold" intraoperatively and adapt to the patient's shape.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers can also be used.

Other materials would also be appropriate, for example, the polyketone known as polyetheretherketone (PEEK™). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). Additionally, pyrolytic carbon can be used.

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. The implant can also be comprised of polyetherketoneketone (PEKK). Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials, each of which is incorporated herein by reference in its entirety.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal, ceramic and/or polymer can be used in combination. For example, one or more metal-containing substrates can be coated with polymers in one or more regions or, alternatively, one or more polymer-containing substrate can be coated in one or more regions with one or more metals.

When polyethylene or other plastics are used, cross-linking techniques known in the art can be applied. Mild, moderate or high cross-linking can be used.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof) or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

Such materials include, without limitation, PEEK, pyrolytic carbone, bioresorbables (e.g., polylactic acid), metals, liquid metals, ceramics, polymers, alloys or combinations thereof.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand various embodiments of the invention and various modifications that are suited to the particular use contemplated.

What is claimed is:

1. An implant for use in a vertebral facet joint of a patient, said implant consisting of: a body at least partially configured to be inserted between first and second opposing articular joint surfaces of the vertebral facet joint, the body of the implant including an interpositional body portion extending along a first longitudinal axis between a first end and a second opposing end of the body of the implant, said implant interpositional body portion including a first articular surface and a second opposing articular surface extending between the first and second ends of the body of the implant and spaced from one another by a thickness of the interpositional body portion of the implant, the first articular surface of the body of the implant configured to engage the first articular joint surface of the vertebral facet joint, and the second articular surface of the body of the implant configured to engage the second opposing articular joint surface of the vertebral facet joint when the interpositional body portion of the implant is inserted between the first and second articular joint surfaces of the vertebral facet joint, at least a portion of the first articular surface of the interpositional body portion of the implant having a concave shape, and at least a portion of the first articular surface of the interpositional body portion of the implant is formed of a non-pliable material and having a three dimensional shape that conforms with a three dimensional shape of the first articular joint surface of the vertebral facet joint of the patient, wherein information used for forming the three dimensional shape of the first articular surface of the body of the implant is derived from electronic image data of the vertebral facet joint of the patient, wherein at least one of the first and second ends of the body of the implant is enlarged relative to the interpositional body portion of the implant, that includes the first and the second articular surfaces of the body of the implant, and defining an implant extrapositional body portion extending along a second longitudinal axis traversing the first longitudinal axis, such that the body of the implant forms a T-shape anchor for further engaging an outer surface of the vertebral facet joint with bone facing surfaces of the implant extrapositional body portion to prevent the body of the implant from sliding or dislodging through the facet joint, such that the implant extrapositional body portion is configured to be located in an extra-articular position when the implant interpositional body portion is implanted in the vertebral facet joint, and wherein the body of the implant, including the interpositional and the extrapositional body portions of the implant, is free of through holes for receiving an attachment mechanism.

2. The implant of claim 1, wherein contours of at least a portion of the second articular surface of the body of the implant substantially conform to corresponding contours of the second articular joint surface of the vertebral facet joint.

3. The implant of claim 1, wherein at least a portion of the second articular surface of the body of the implant substantially forms a negative of a corresponding portion of the second articular joint surface of the vertebral facet joint.

4. The implant of claim 1, wherein the first articular surface of the body of the implant is configured to secure the body of the implant relative to the first articular joint surface when the implant interpositional body portion is implanted in the vertebral facet joint.

5. The implant of claim 1, wherein at least a portion of the first articular surface of the body of the implant is configured to interdigitate with a corresponding portion of the first articular joint surface of the vertebral facet joint when the implant interpositional body portion is implanted in the vertebral facet joint.

6. The implant of claim 1, wherein the second articular surface of the body of the implant is substantially smooth.

7. The implant of claim 1, wherein the other one of the first and second ends of the body of the implant is enlarged relative to a middle portion of the interpositional body portion of the implant and is configured to enlarge a space between the first and second articular joint surfaces of the vertebral facet joint.

8. The implant of claim 1, the body of the implant includes an attachment mechanism configured to secure the body of the implant in the vertebral facet joint.

9. The implant of claim 8, wherein the attachment mechanism is a protrusion selected from the group consisting of a pin and a fin projecting from the second articular surface of the body of the implant.

* * * * *